(12) United States Patent
Kimura

(10) Patent No.: US 8,743,250 B2
(45) Date of Patent: *Jun. 3, 2014

(54) SEMICONDUCTOR DEVICE AND METHOD OF DRIVING THE SAME

(71) Applicant: Semiconductor Energy Laboratory Co., Ltd., Kanagawa-ken (JP)

(72) Inventor: Hajime Kimura, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/737,112

(22) Filed: Jan. 9, 2013

(65) Prior Publication Data

US 2013/0129050 A1 May 23, 2013

Related U.S. Application Data

(60) Continuation of application No. 13/525,653, filed on Jun. 18, 2012, now Pat. No. 8,355,065, which is a continuation of application No. 12/895,022, filed on Sep. 30, 2010, now Pat. No. 8,203,636, which is a continuation of application No. 11/650,671, filed on Jan. 8, 2007, now Pat. No. 7,808,535, which is a division of application No. 09/829,114, filed on Apr. 9, 2001, now abandoned.

(30) Foreign Application Priority Data

Apr. 12, 2000 (JP) .................................. 2000-111424

(51) Int. Cl.
*H04N 3/14* (2006.01)
*H04N 5/335* (2011.01)

(52) U.S. Cl.
USPC ............ 348/294; 348/298; 348/302; 348/308

(58) Field of Classification Search
USPC .............. 348/222.1, 294, 298, 302, 308, 312; 250/208.1; 257/290–292
See application file for complete search history.

(56) References Cited

U.S. PATENT DOCUMENTS 4,937,674 A 6/1990 Mizoguchi et al.
4,974,239 A 11/1990 Miwada
(Continued)

FOREIGN PATENT DOCUMENTS

CN 1224511 A 7/1999
DE 199 17 863 C1 1/2001
(Continued)

OTHER PUBLICATIONS

Fossum, E.R., "CMOS Image Sensors: Electronic Camera on a Chip," IDEM 95: Technical Digest of International Electron Devices Meeting, 1995, pp. 17-25.

(Continued)

*Primary Examiner* — Yogesh Aggarwal
(74) *Attorney, Agent, or Firm* — Husch Blackwell LLP

(57) ABSTRACT

To provide a semiconductor device and a driving method of the same that is capable of enlarging a signal amplitude value as well as increasing a range in which a linear input/output relationship operates while preventing a signal writing-in time from becoming long. The semiconductor device having an amplifying transistor and a biasing transistor and the driving method thereof, wherein an electric discharging transistor is provided and pre-discharge is performed.

27 Claims, 30 Drawing Sheets

(56) References Cited

U.S. PATENT DOCUMENTS

| | | | |
|---|---|---|---|
| 5,192,990 A | 3/1993 | Stevens | |
| 5,808,677 A | 9/1998 | Yonemoto | |
| 5,835,554 A * | 11/1998 | Suzuki et al. | 378/98 |
| 5,880,460 A | 3/1999 | Merrill | |
| 5,898,168 A | 4/1999 | Gowda et al. | |
| 5,917,365 A | 6/1999 | Houston | |
| 5,917,547 A | 6/1999 | Merrill et al. | |
| 5,998,779 A | 12/1999 | Kozuka | |
| 6,002,432 A | 12/1999 | Merrill et al. | |
| 6,031,248 A | 2/2000 | Mei et al. | |
| 6,037,979 A | 3/2000 | Yonemoto | |
| 6,043,525 A | 3/2000 | Chen | |
| 6,091,449 A | 7/2000 | Matsunaga et al. | |
| 6,147,556 A | 11/2000 | Nakano | |
| 6,157,016 A | 12/2000 | Clark et al. | |
| 6,166,767 A | 12/2000 | Watanabe | |
| 6,236,063 B1 | 5/2001 | Yamazaki et al. | |
| 6,239,839 B1 | 5/2001 | Matsunaga et al. | |
| 6,243,069 B1 | 6/2001 | Ogawa et al. | |
| 6,300,978 B1 | 10/2001 | Matsunaga et al. | |
| 6,366,321 B1 | 4/2002 | Yonemoto | |
| 6,445,371 B1 | 9/2002 | Miyazawa et al. | |
| 6,512,544 B1 | 1/2003 | Merrill et al. | |
| 6,556,244 B1 | 4/2003 | So et al. | |
| 6,583,439 B2 | 6/2003 | Yamazaki et al. | |
| 6,690,842 B1 | 2/2004 | Silver et al. | |
| 6,713,748 B1 | 3/2004 | Tsutsumi et al. | |
| 6,734,907 B1 | 5/2004 | Hagihara et al. | |
| 6,795,121 B2 | 9/2004 | Matsunaga et al. | |
| 6,801,256 B1 | 10/2004 | Egawa et al. | |
| 6,836,291 B1 | 12/2004 | Nakamura et al. | |
| 6,873,362 B1 | 3/2005 | Yonemoto | |
| 6,950,132 B1 | 9/2005 | Kozuka | |
| 6,963,372 B1 | 11/2005 | Hiyama et al. | |
| 6,967,682 B1 | 11/2005 | Hagihara | |
| 6,999,122 B1 | 2/2006 | Hagihara et al. | |
| 7,113,213 B2 | 9/2006 | Matsunaga et al. | |
| 7,164,443 B1 | 1/2007 | Hagihara | |
| 7,180,092 B2 | 2/2007 | Yamazaki et al. | |
| 7,292,276 B2 | 11/2007 | Egawa et al. | |
| 7,295,236 B1 | 11/2007 | Bellingrath et al. | |
| 7,362,366 B2 | 4/2008 | Egawa et al. | |
| 7,369,169 B2 | 5/2008 | Matsunaga et al. | |
| 2001/0013901 A1 | 8/2001 | Matsunaga et al. | |
| 2002/0167601 A1 | 11/2002 | Ohzu et al. | |
| 2005/0068432 A1 | 3/2005 | Kozuka | |
| 2008/0055447 A1 | 3/2008 | Bellingrath et al. | |

FOREIGN PATENT DOCUMENTS

| | | |
|---|---|---|
| EP | 0 324 456 A2 | 7/1989 |
| EP | 0 665 685 A2 | 8/1995 |
| EP | 0 845 900 A1 | 6/1998 |
| EP | 0 851 673 A2 | 7/1998 |
| EP | 0 909 086 A2 | 4/1999 |
| EP | 0 915 367 A1 | 5/1999 |
| EP | 0 952 730 A2 | 10/1999 |
| JP | 1-135274 | 5/1989 |
| JP | 1-181564 | 7/1989 |
| JP | 1-184954 A | 7/1989 |
| JP | 1-502634 | 9/1989 |
| JP | 2-107075 | 4/1990 |
| JP | 4-71271 A | 3/1992 |
| JP | 5-227487 | 9/1993 |
| JP | 6-105068 | 4/1994 |
| JP | 6-177377 A | 6/1994 |
| JP | 7-255013 | 10/1995 |
| JP | 8-88369 | 4/1996 |
| JP | 8-153866 | 6/1996 |
| JP | 8-265065 | 10/1996 |
| JP | 9-45930 A | 2/1997 |
| JP | 9-247538 | 9/1997 |
| JP | 9-252434 | 9/1997 |
| JP | 10-173997 | 6/1998 |
| JP | 10-191173 | 7/1998 |
| JP | 11-112728 | 4/1999 |
| JP | 11-136582 | 5/1999 |
| JP | 11-164208 | 6/1999 |
| JP | 11-205683 | 7/1999 |
| JP | 11-205693 | 7/1999 |
| JP | 11-326954 | 11/1999 |
| JP | 2000-4399 | 1/2000 |
| JP | 2000-12866 | 1/2000 |
| JP | 2000-31453 A | 1/2000 |
| JP | 2000-106651 | 4/2000 |
| KR | 2000-0005777 | 1/2000 |
| WO | WO 88/02186 A1 | 3/1988 |
| WO | WO 97/07628 A1 | 2/1997 |
| WO | WO 99/66560 A1 | 12/1999 |

OTHER PUBLICATIONS

Wong, H.S.P., "CMOS Image Sensors—Recent Advances and Device Scaling Considerations," IDEM 97: Technical Digest of International Electron Devices Meeting, 1997, pp. 201-204.

Oba, E. et al, "FA 11.1: a 3 Inch 330K Square Pixel Progressive Scan CMOS Active Pixel Image Sensor," ISSCC 97 (Digest of Technical Papers. IEEE International Solid State Circuits Conference), Feb. 6-8, 1997, IEEE, vol. 40, 1997, pp. 180-181.

Oba, E. et al, "FA 11.1: A 1/4 Inch 330K Square Pixel Progressive Scan CMOS Active Pixel Image Sensor," ISSCC 97 (Digest of Technical Papers. IEEE International Solid State Circuits Conference), Feb. 6-8, 1997, IEEE, vol. 40, 1997, pp. 180-181.

Fossum, E.R., "CMOS Image Sensors: Electronic Camera on a Chip," IDEM 95, 1995, pp. 17-25.

Wong, H.S.P., "CMOS Image Sensors—Recent Advances and Device Scaling Considerations," IDEM 97, 1997, pp. 201-204.

Oba, E. et al, "FA 11.1: A 3 Inch 330K Square Pixel Progressive Scan CMOS Active Pixel Image Sensor," 1997 IEEE International Solid State Circuits Conference, Feb. 6-8, 1997, IEEE, vol. 40, 1997, pp. 180-181.

"Development Prospects of the CMOS Camera," JIEC Seminar, 1998, Fig. 11, p. 9.

Weisfield, R.L., "Amorphous Silicon TFT X-Ray Image Sensors," IEDM 98, 1998, pp. 21-24.

Moy, J.P et al, "X-Ray Detectors Based on Amorphous Silicon Active Matrix," EURODISPLAY '99, Proceedings of the 19th International Display Research Conference, Berlin, Germany, Sep. 6-9, 1999, pp. 203-207.

Ikeda, M. et al, "Real-Time Imaging Flat Panel X-Ray Detector," AM-LCD '99, 1999, pp. 45-48.

European Search Report re application No. EP 01109073.5, dated Nov. 3, 2009.

* cited by examiner

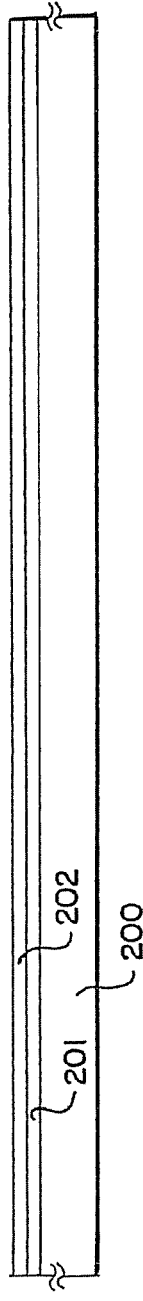
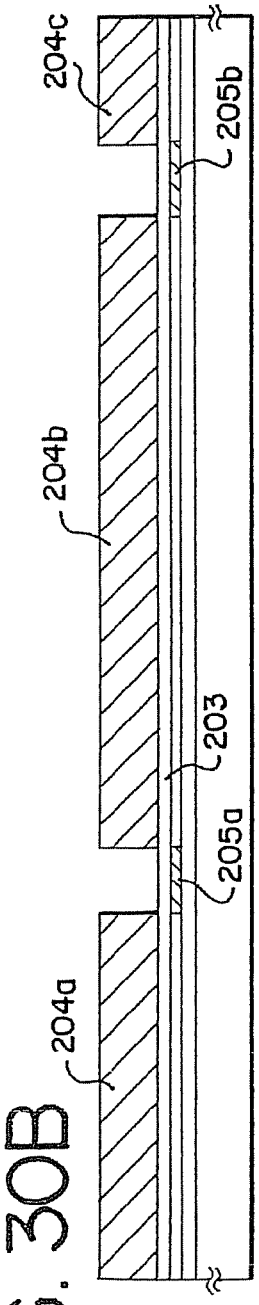
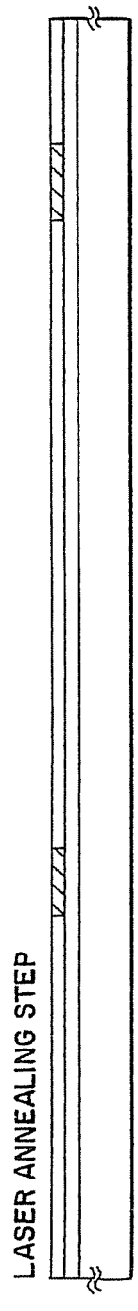
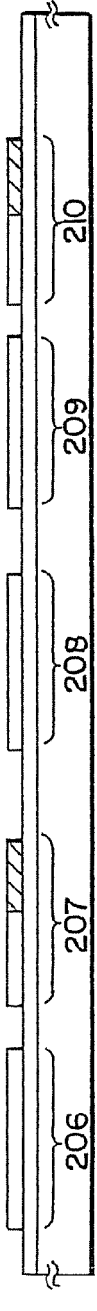
FIG. 30A CRYSTALLIZATION STEP
FIG. 30B
FIG. 30C LASER ANNEALING STEP
FIG. 30D

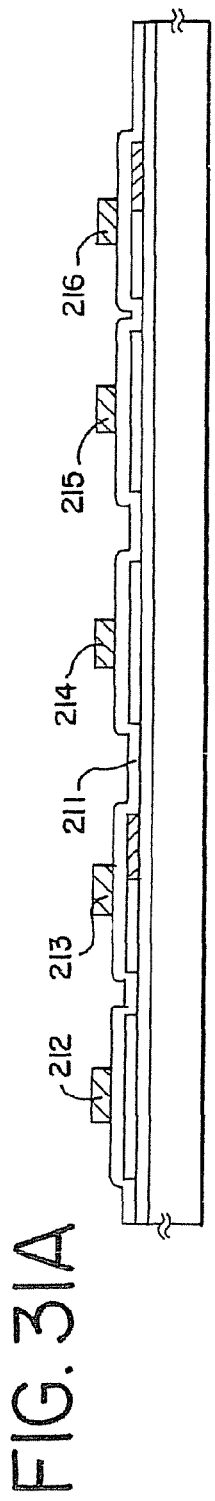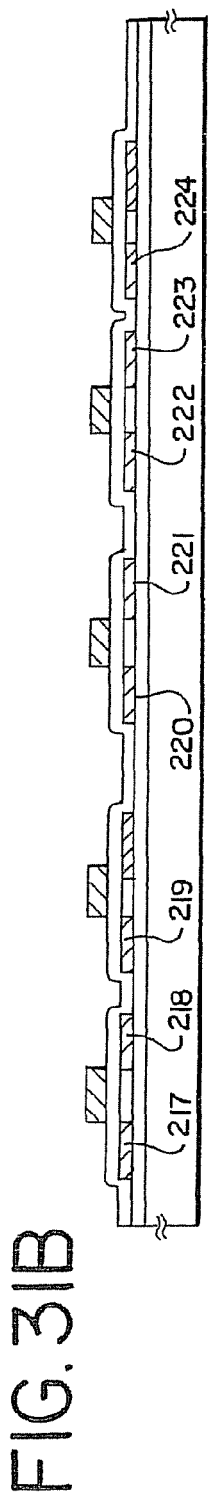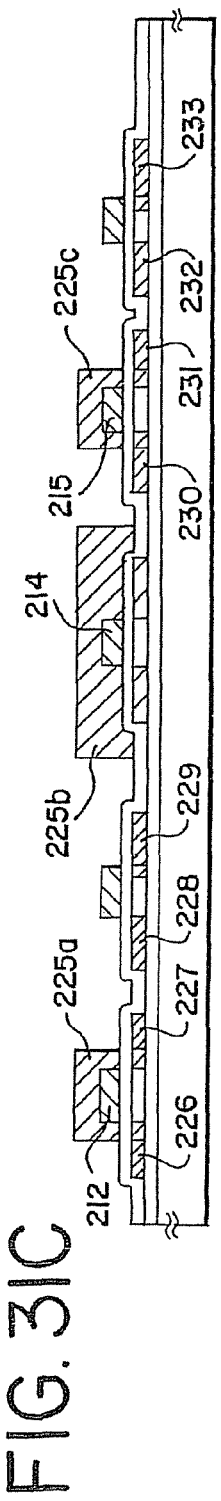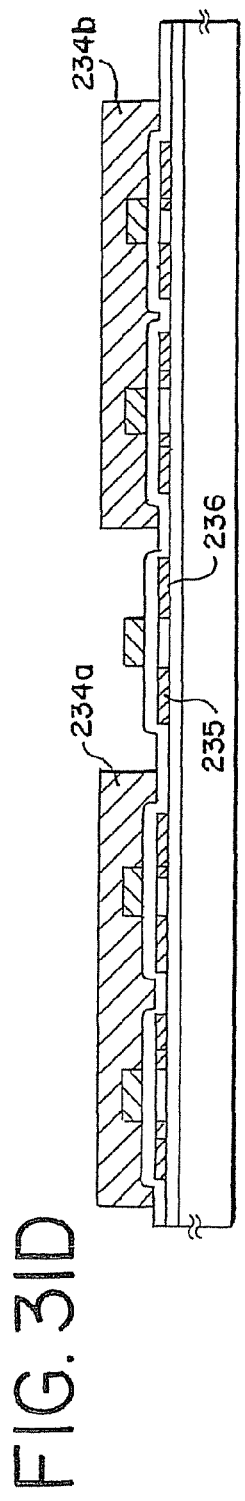

SEMICONDUCTOR DEVICE AND METHOD OF DRIVING THE SAME

This application is a divisional of copending U.S. application Ser. No. 09/829,114 filed on Apr. 9, 2001.

BACKGROUND OF THE INVENTION

1. Field of the Invention

The present invention relates to a semiconductor device and a driving method thereof. Specifically, the present invention relates to an MOS sensor device that has an image sensor function and to a driving method of the same.

2. Description of the Related Art

In recent years, the use of information equipment such as a personal computer has spread widely, and hence the demand to read (store) various information in the personal computer, etc. as electronic information is rising. Therefore, replacing the conventional silver salt camera, a digital still camera or a scanner, which is used as a means of reading information printed on paper, are in the spotlight.

An area sensor in which the pixels are arranged in a two-dimensional way is used in the digital still camera. In the scanner, a copier machine, etc., a line sensor in which the pixels are arranged in a one-dimensional way is used. In the case of using the line sensor to read a two-dimensional image, signals are read while moving the line sensor.

A CCD type sensor is mainly used as the image sensor in these types of image reading equipments. In the CCD type sensor, a photoelectric conversion is carried out in a photo diode of each of the pixels and then the CCD is used to read those signals. However, an MOS type sensor that is formed by using a single crystal silicon substrate is showing signs of popularization in a part of the technical field thereof by using factors such as the incorporation of a peripheral circuit, manufacturing it into one chip, its suitability for a real time signal process, and its low consumption power as weapons. Further, the manufacture of an MOS type sensor by using a TFT that is formed on a glass substrate is being developed at the research level. In the MOS type sensor, the photoelectric conversion is carried out in the photo diode of each of the pixels, whereby the signals of the respective pixels are read out by using a switch that is formed by an MOS transistor.

As a pixel structure of the MOS type sensor, various types are being developed. The various types of pixel structure of the MOS type sensor can be largely categorized into two types, that is, a passive sensor type and an active sensor type. The passive sensor is a sensor in which a signal amplitude element is not incorporated into the respective pixels whereas the active sensor is a sensor in which a signal amplitude element is incorporated into the respective pixels. The active sensor has an advantage over the passive sensor in that it is strong against noise because the signals are amplified in each of the pixels.

Shown in FIG. 2 is an example of a circuit of a pixel in the passive sensor. A pixel 10005 is composed of a switching transistor 10001 and a photo diode 10004. The photo diode is connected to a power source standard line 10006 and to a source terminal of the switching transistor 10001. A gate signal line 10002 is connected to a gate terminal of the switching transistor 10001, and a signal output line 10003 is connected to a drain terminal thereof. Photoelectric conversion takes place in the photo diode 10004. In other words, an electric charge is generated in response to the incidence of light, whereby the electric charges are accumulated therein. Then the switching transistor 10001 is made into conductive by controlling the gate signal line 10003 to thereby read out the electric charge of the photo diode 10004 through the signal output line 10003.

There are various kinds of pixel structure of the active sensor. Pixel structures such as a photo diode type and a photo gate type and their operations are introduced in IEDM95: p. 17: CMOS Image Sensors, Electric Camera On a Chip or in IEDM97: p. 201: CMOS Image Sensors—Recent Advances and Device Scaling Considerations. In the ISSCC97: p. 180: A ¼ Inch 330k Square Pixel Progressive Scan CMOS Active Pixel Image Sensor, the pixel structure is categorized from the perspective of a selecting method of the pixel. That is, a case of whether to use a transistor or a capacitance as a selecting element is described therein. Thus, there are various types of structures regarding the number of transistors for forming one pixel. A general description of the CMOS type sensor is broadly introduced in the JIEC Seminar: Development Prospects of the CMOS Camera: Feb. 20, 1998. In the description thereof, a logarithm conversion form, which outputs a signal of the logarithm of light density by connecting a gate electrode and a drain electrode of a resetting transistor, is also explained.

As shown in FIG. 3, a pixel structure of the active sensor that is mostly adopted is a type that is composed of three N channel transistors and one photo diode, thereby forming one pixel 308. A P channel side terminal of a photo diode 304 is connected to a power source standard line 312, and an N channel side terminal of the photo diode 304 is connected to a gate terminal of an amplifying transistor 306. A drain terminal and a source terminal of the amplifying transistor 306 are connected to a power source line 309 and to a drain terminal of a switching transistor 301, respectively. A gate terminal of the switching transistor 301 is connected to a gate signal line 302 while a source terminal thereof is connected to a signal output line 303. A gate terminal of a resetting transistor 307 is connected to a reset signal line 306. A source terminal and a drain terminal of the resetting transistor 307 are connected to the power source line 309 and a gate terminal of the amplifying transistor 306, respectively.

In the case of an area sensor, not only one pixel 308 is connected to one signal output line 303, but also a plurality of pixels are connected thereto. However, one biasing transistor 311 is connected per signal output line 303. A gate terminal of the biasing transistor 311 is connected to a bias signal line 310. A source terminal and a drain terminal of the biasing transistor 311 are connected to the signal output line 303 and to a biasing power source line 313.

Next, a basic operation of the pixel 308 will be explained.

The resetting transistor 307 is first made into a conductive state. Because the P channel side terminal of the photo diode 304 is connected to the power source standard line 312, whereby the photo diode 304 becomes a state in which the N channel side terminal is electrically connected to the power source line 309, an inverted bias voltage is applied to the photo diode 304. Hereinafter, the operation of charging the N channel side terminal of the photo diode 304 until its electric potential is equivalent to the electric potential of the power source line 309 will be referred as "reset". Thereafter, the resetting transistor 307 is made into a non-conductive state. When light is being irradiated to the photo diode 304, an electric charge is generated due to a photoelectric conversion. Therefore, as time elapses, the electric potential of the N channel side terminal of the photo diode 304, which has been charged up to the electric potential of the power source line 309, gradually becomes smaller because of an electric charge that was generated by the light. Then after a fixed period of time has passed, the switching transistor 301 is made into a conductive state, whereby a signal is output to the signal output line 303 through the amplifying transistor 306.

However, at the time the signal is being output, an electric potential is applied to the bias signal line 310 to cause a current to flow in the biasing transistor 311. Therefore, the amplifying transistor 306 and the biasing transistor 311 operate as the so-called source follower circuits.

An example of the most basic source follower circuit is shown in FIG. 4. In FIG. 4, the case of using the N channel transistor is described. Although a P channel transistor can be used to construct the source follower circuit, a case of using an N channel transistor is shown in FIG. 4. A power source electric potential Vdd is applied to an amplifier side power source line 403. A standard electric potential 0V is applied to a bias side power source line 404. A drain terminal of an amplifying transistor 401 is connected to the amplifier side power source line 403 while a source terminal thereof is connected to a drain terminal of a biasing transistor 402. A source terminal of the biasing transistor 402 is connected to the bias side power source line 404. A bias electric potential Vb is applied to a gate terminal of the biasing transistor 402. Therefore, a bias current Ib flows in the biasing transistor 402. The biasing transistor 402 basically operates as a fixed electric current source. A gate terminal of the amplifying transistor 401 serves as an input terminal 406. An input electric potential Vin is thus applied to the gate terminal of the amplifying transistor 401. A source terminal of the amplifying transistor 401 serves as an output terminal 407, and therefore an output electric potential Vout is applied to the source terminal of the amplifying transistor 401. At this point, the relationship of the input/output of the source follower circuit becomes Vout=Vin−Vb.

In the case of comparing the circuit configurations of FIG. 3 and FIG. 4, the amplifying transistor 306 corresponds to the amplifying transistor 401, and the biasing transistor 311 corresponds to the biasing transistor 402. Because it is assumed that the switching transistor 301 is in conductive, it can be observed that a switching transistor is omitted in FIG. 4. The electric potential of the N channel side terminal of the photo diode 304 corresponds to the input electric potential Vin (the gate electric potential of the amplifying transistor 401, that is, the electric potential of the input terminal 406). The electric potential of the signal output line 303 corresponds to the output electric potential Vout (the source electric potential of the amplifying transistor 401, that is, the electric potential of the output terminal 407).

Therefore, in FIG. 3, if the electric potential of the N channel side terminal of the photo diode 304 is Vpd, the electric potential of the bias signal line 310, that is, the bias electric potential is Vb, the electric potential of the signal output line 303 is Vout, and the electric potential of the power source standard line 312 and the bias side power source line 313 is 0V, then the relationship becomes Vout=Vpd−Vb. Accordingly, when the electric potential Vpd of the N channel side terminal of the photo diode 304 changes, then Vout also changes. As a result, the change of the Vpd can be output as a signal and the light intensity can thus be read.

The basic operation of the source follower circuit is one as described above. However, the operating principle of the source follower circuit will be explained next in detail because it is needed for explaining the operation of the present invention. For simplification, it is assumed that the sizes and characteristics of the amplifying transistor and the biasing transistor are the same in the explanation here. Further, an electric current characteristic of the transistors is an ideal one, that is, even if a voltage between the source and the drain changes, it is assumed that an electric current value in a saturated region does not change.

First, as shown in FIG. 4, the bias electric potential Vb is applied to the gate terminal of the biasing transistor 402. In the case the biasing transistor 402 operates in the saturated region, the electric current Ib flows therein as shown in FIG. 5. On the other hand, the same amount of electric current will flow in amplifying transistor 401 and the biasing transistor 402 under a fixed normal state because both transistors are connected in series. Therefore, when the electric current Ib is flowing in the biasing transistor 402, the electric current Ib is also flowing in the amplifying transistor 401. In order to cause the electric current Ib to flow in the amplifying transistor 401, it is necessary to make the voltage Vgs between the gate and the source of the amplifying transistor 401 equivalent to the bias electric potential Vb.

Thus, the output electric potential Vout in the source follower circuit is obtained. The amount of electric potential of the output electric potential Vout that is lower than the input electric potential Vin is equal to only that of the voltage Vgs between the gate and the source of the amplifying transistor 401. Therefore, the input/output relationship becomes Vout=Vin−Vgs. The voltage Vgs between the gate and the source of the amplifying transistor 401 is equal to the bias electric potential Vb, and hence the input/output relationship becomes Vout=Vin−Vb. However, as shown in FIG. 5, this equation is only valid when the biasing transistor 402 operates in the saturated region (corresponds to the case when Vin is large). In the case Vin is small and the biasing transistor 402 operates in a linear region, the equation Vout=Vin−Vb cannot become valid as shown in FIG. 6. When the biasing transistor operates in the linear region, the input/output relationship becomes Vout=Vin−Vb'. The Vb' here is the voltage between the gate and the source of the amplifying transistor 401 at that point. If the electric current flowing in the biasing transistor 402 is Ib' when the biasing transistor 402 is operating in the linear region, then Ib'<Ib. Consequently, the relationship between Vb and Vb' becomes Vb'<Vb. In other words, when Vin and Ib' becomes small, then Vb' also becomes small. As a result, the input/output relationship (relationship between Vin and Vout) becomes non-linear as shown in FIG. 7.

The following fact can be discerned from the above explanation.

First, to increase an amplitude value of the output electric potential Vout in the source follower circuit, it is appropriate to make the bias electric potential Vb small. Since Vout=Vin−Vb, when Vb is small, the Vout can be increased. However, it is necessary that the biasing transistor 402 be in conductive. Therefore, the value of the bias electric potential Vb must be made larger than that of a threshold voltage of the biasing transistor 402.

To the contrary, in the case the bias electric potential Vb is large, the biasing transistor 402 can readily operate in the linear region when the input electric potential Vin becomes small. As a result, the input/output relationship of the source follower circuit is likely to become non-linear. It is appropriate, in this respect, to make the bias electric potential Vb small.

The operation of the source follower circuit under a fixed normal state has been explained so far. Next, the operation of the source follower circuit under a transient state will be explained. As a circuit structure thereof, the circuit shown in FIG. 4 will be used with the addition of a load. In other words, the circuit structure here is a structure in which a load capacitance 805 is connected between output terminals, that is, a source terminal of an amplifying transistor 801 and a load capacitance power source line 806 as shown in FIG. 8. Therefore, the electric potential of the load capacitance 805 is the same as the output electric potential Vout of the source follower circuit.

First, a case where the output electric potential Vout is small in the initial state, that is, when Vout<Vin−Vb. FIG. 8A is a diagram showing a circuit configuration, and FIG. 8B is a diagram showing a timing chart. In that case, a value of a voltage Vgs between a gate and a source of an amplifying transistor 801 is larger than a value of a voltage Vgs between a gate and a source of a biasing transistor 802. Therefore, a large electric current flows in the amplifying transistor 801, and as a result, a load capacitance 805 is rapidly charged and the output electric potential Vout becomes large, whereby the voltage Vgs between the gate and the source of the amplifying transistor 801 becomes smaller. When the voltage Vgs between the gate and the source of the amplifying transistor 801 finally becomes equivalent to the bias electric potential Vb, the transient state is turned into a fixed normal state. The output electric potential Vout at that point is Vout=Vin−Vgs=Vin−Vb. Thus, as in the case where Vout<Vin−Vb, initially the voltage Vgs between the gate and the source of the amplifying transistor 801 is large under the transient state. Therefore, a large electric current, passing through the amplifying transistor 801, flows to the load capacitance 805. The writing-in time of a signal to the load capacitance 805 can thus be performed in a short time.

On the other hand, a case is discussed where the output electric potential Vout is large in the initial state, that is, when Vout>Vin−Vb. FIG. 9A is a diagram showing a circuit configuration thereof, and FIG. 9B is a diagram showing a timing chart thereof. In that case, because a value of a voltage Vgs between a gate and a source of an amplifying transistor 901 is small, the amplifying transistor 901 is in a non-conductive state. Then, the electric charges that have accumulated in a load capacitance 905 flow through a biasing transistor 902 to thereby be discharged. At that point, a voltage between a gate and a source of the biasing transistor 902 is the bias electric potential Vb, and therefore the electric current flowing in the biasing transistor 902 becomes Ib. As the output electric potential Vout gradually becomes smaller, the voltage Vgs between the gate and the source of the amplifying transistor 901 becomes larger. When the voltage Vgs between the gate and the source of the amplifying transistor 901 finally becomes equivalent to the bias electric potential Vb, the transient state is turned into the fixed normal state. Under the fixed normal state, the value of Vout is a fixed value, and hence an electric current will not flow in the load capacitance 905. The electric current Ib will continuously flow in the 2 transistors of the source follower circuit.

Thus, from the above explanation, it can be understood that when Vout>Vin−Vb, the electric discharging time of the load capacitance 905, that is, the signal writing-in time is determined by the electric current Ib flowing through the biasing transistor 902. The amount of the electric current Ib is determined by the size of the bias electric potential Vb. Therefore, to increase the electric current in order to shorten the signal writing-in time to the load capacitance 905, it is necessary to increase the bias electric potential Vb.

Next, a timing chart of a signal in a pixel 309 is shown in FIG. 10. First, the resetting transistor 307 is turned into a conductive state by controlling the reset signal line 305, whereby the electric potential of the N channel side terminal of the photo diode 304 is charged until the electric potential Vd of the power source line 309. In other words, the pixel is reset. Subsequently, the resetting transistor 307 is turned into a non-conductive state by controlling the reset signal line 305. Thereafter, when light is irradiated to the photo diode 304, an electric charge according to the light density is generated. Therefore, the electric charge that is charged due to the resetting operation is gradually being discharged. In short, the electric potential of the N channel side terminal of the photo diode 304 decreases. In the case a dark light is irradiated to the photo diode 304, the amount of electric discharge is small, and therefore the electric potential of the N channel side terminal of the photo diode 304 does not decrease much. Then, at a certain point, the switching transistor 301 is turned into a conductive state to thereby read-out the electric potential of the N channel side terminal of the photo diode 304 as a signal. This signal is proportional to the density of light. Then, the resetting transistor 307 is turned into the conductive state again to thereby reset the photo diode 304, and similar operations are repeated.

A transistor in the pixel 309 will be explained next. Regarding the polarity of the transistor thereof, all are N channel types most of the time. In rare cases, a P channel type may be used for the resetting transistor (JIEC Seminar: Development Prospects of the CMOS Camera: Feb. 20, 1998, refer to FIG. 11). Further, with regard to a method of lining up (arranging) the amplifying transistor and a selecting transistor, N channel types are used for both transistors and as shown in FIG. 3, often the structure is one in which the power source line 309 and the amplifying transistor 306 are connected, the amplifying transistor 306 and the switching transistor 301 are connected, and the switching transistor 301 and the signal output line 303 are connected. In rare cases N channel types are used for both transistors and the structure thereof is one in which the power source line 309 and the switching transistor 301 are connected, the switching transistor 301 and the amplifying transistor 306 are connected, and the amplifying transistor 306 and the signal output line 306 are connected (ISSCC97: p. 180, A ¼ Inch 330K Square Pixel Progressive Scan CMOS Active Pixel Image Sensor).

Next, a sensor portion for performing photoelectric conversion or the like will be explained. A PN type of photo diode is usually used to convert light into electricity. However, there are other types including a PIN type diode, an avalanche diode, an NPN incorporated diode, a Schottky diode, etc. There are also others such as a photo diode for X-rays and a sensor for infrared rays. These are described in "The Basics of Solid Imaging Elements: DENSHINO MENO SHIKUMI" written by Takao Ando and Hirohito Kobuchi: Nippon Riko Shuppan Kai.

Products suitable as sensors will be explained, next. Other than the digital still camera and scanner, a sensor may also be used in an X-ray camera. In that case, there is a case where the photo diode for directly converting an X-ray into an electric signal is used or a case where an X-ray is converted into light by using a fluorescent material or a scintillator and then the light is read. The case of converting an X-ray into light by using a scintillator and thereafter reading the light is described in "Euro Display 99: p. 203: X-ray Detectors base on Amorphous Silicon Active Matrix". In the "IEDM 98: p. 21: Amorphous Silicon TFT X-ray Image Sensors", a case of reading light by using an amorphous silicon is reported, and a case of reading light by using a photo conductor is reported in the "AM-LCD99: p. 45: Real-time Imaging Flat Panel X-ray Detector".

First, consideration is made on the item required in a source follower circuit 405. The most necessary item is to obtain a value as large as possible as an amplitude of the output electric potential Vout, that is, a value that is roughly equivalent to an amplitude of the input electric potential Vin. If the amplitude of the output electric potential Vout is large, signals having a large number of gradations can be obtained. As a result, the quality of the image read from an image sensor is enhanced. In addition, it is necessary that the input/output relationship is linear. In other words, it is crucial that the relationship of the input electric potential Vin and the output electric potential Vout in the source follower circuit operate linearly in a wide range. That is, the relationship of Vout=Vin−Vb is maintained even if the input electric potential Vin is small. In short, it is important that the biasing transistor 402 operate in the saturated region. Other items that are necessary include a short signal writing-in time of the output electric potential Vout to the load capacitance. If the signal writing-in time is long, the operation thereof will become slow.

Then, consideration is now made regarding a method to satisfy the above-mentioned items required in the source follower circuit.

First, because Vout=Vin−Vb, it is appropriate to make the bias electric potential Vb small in order to increase the amplitude of the output electric potential Vout. Similarly, the bias electric potential Vb may be made small in order to widen the operating region of a linear input/output relationship. The reason for this resides in that when the bias electric potential Vb is small, the biasing transistor 402 can easily operate in the saturated region even if the output electric potential has become small. However, when the bias electric potential Vb is small, the writing-in time of the output signal becomes long.

In other words, the amplitude of the output electric potential and the signal writing-in time have a trade-off relationship. It is impossible to shorten the writing-in time of the output electric potential while increasing the amplitude value of the output electric potential. In addition, it is also impossible to widen the operating region in which the input/output relationship is linear while increasing the amplitude value of the output electric potential.

SUMMARY OF THE INVENTION

The present invention has been made in view of the above problems, and therefore has an object to solve the above problems of the prior art.

According to the present invention, in a source follower circuit that employs an N channel transistor, prior to outputting a signal therefrom, an output electric potential (electric potential of a load capacitance) is lowered once (in the case of a source follower circuit employing a P channel transistor, the output electric potential is raised). Hereinafter, the process of lowering the output electric potential (electric potential of the load capacitance) of the source follower circuit (in the case where a P channel is employed, increasing the electric potential thereof) is referred to as "pre-discharge", and a period during which the pre-discharge is performed is referred to as "pre-discharge period". In the present invention, an actual signal is output after a pre-discharge.

Conventionally, in a source follower circuit employing an N channel transistor, an electric charge of the load capacitance was discharged through a biasing transistor when Vout>Vin−Vb in the initial state. However, in the present invention, the electric potential of the load capacitance is lowered once to thereby make the source follower circuit in a state where Vout<Vin−Vb. This operation is the pre-discharge. Thereafter, the actual signal is output. Since the follower circuit is already in the state where Vout<Vin−Vb at the time of outputting the actual signal, the signal is output to the load capacitance through an amplifying transistor. Therefore, the signal writing-in time does not become long.

An electric potential that is slightly higher than a threshold voltage of the biasing transistor, that is, an electric potential value as low as possible, is applied to a gate electric potential of the biasing transistor when outputting the actual signal, in other words, the bias electric potential Vb. The reasons for this resides in that considering the input/output relationship Vout=Vin−Vb of the source follower circuit, it is preferable to lower the bias electric potential Vb as much as possible in order to increase the output electric potential Vout. However, it is necessary that the biasing transistor be in conductive state. In short, it is necessary that the biasing transistor operate in the saturated region. Accordingly, the gate electric potential of the biasing transistor when outputting the actual signal, that is, the bias electric potential Vb is made slightly higher than the threshold voltage of the biasing transistor. In practice, the electric potential is made slightly higher than the highest threshold voltage in all the biasing transistors in a circuit.

Even if, the bias electric potential Vb is made small, and therefore the amount of electric current of the biasing transistor becomes small, the electric charge of the load capacitance is not discharged through the biasing transistor. Hence, the signal writing-in time does not become long. In addition, because the bias electric potential is small, the operating region in which the input/output relationship is linear is wide. Therefore, it is possible to prevent the signal writing-in time from becoming long, and enlarging the amplitude of the output electric potential and widening the operating region in which the input/output relationship is linear at the same time. The structure of the present invention will be described below.

According to the present invention, there is provided a semiconductor device having an amplifying transistor, a biasing transistor, an amplifying side power source line, a biasing side power source line, a bias signal line, an electric discharging transistor, and an electric discharging power source line, characterized in that:

a drain terminal of the amplifying transistor is connected to the amplifying side power source line, a source terminal of the biasing transistor is connected to the biasing side power source line, a source terminal of the amplifying transistor is connected to a drain terminal of the biasing transistor, a gate terminal of the biasing transistor is connected to the bias signal line, a gate terminal of the amplifying transistor serves as an input terminal, and a source terminal of the amplifying transistor serves as an output terminal, and one of the output terminal and the electric discharging power source line is connected to a source terminal of the electric discharging transistor while the other thereof is connected to a drain terminal of the electric discharging transistor.

According to the present invention, there is provided a semiconductor device having an amplifying transistor, a biasing transistor, an amplifying side power source line, a biasing side power source line, and a bias signal line, characterized in that:

a drain terminal of the amplifying transistor is connected to the amplifying side power source line, a source terminal of the biasing transistor is connected to the biasing side power source line, a source terminal of the amplifying transistor is connected to a drain terminal of the biasing transistor, a gate terminal of the biasing transistor is connected to the bias signal line, a gate terminal of the amplifying transistor serves as an input terminal, and a source terminal of the amplifying transistor serves as an output terminal, and a signal generating device is connected to the bias signal line for performing the operation of making the electric potential of the biasing side power source line close to the electric potential of the amplifying side power source line.

According to the present invention, there is provided a semiconductor device, characterized in that one terminal of a load capacitance is connected to the output terminal, and the other terminal of the load capacitance is connected to a load capacitance power source line.

According to the present invention, there is provided a semiconductor device, characterized in that the electric discharging power source line is connected to the biasing side power source line.

According to the present invention, there is provided a semiconductor device, characterized in that at least 2 lines from among the electric discharging power source line, the load capacitance power source line, and the biasing side power source line are connected together.

According to the present invention, there is provided a semiconductor device, characterized in that the load capacitance power source line is connected to the amplifying side power source line.

According to the present invention, there is provided a semiconductor device, characterized in that the semiconductor device has at least one selecting switch for controlling an electric current flowing to the load capacitance or the output terminal from the amplifying side power source line or from the biasing side power source line.

According to the present invention, there is provided a semiconductor device, characterized in that the semiconductor device has at least one selecting switch for controlling an electric current flowing to the output terminal from the amplifying side power source line or from the biasing side power source line.

According to the present invention, there is provided a semiconductor device, characterized in that the selecting switch has at least one of an N channel transistor or a P channel transistor.

According to the present invention, there is provided a semiconductor device, characterized in that an absolute value of a voltage between a gate and a source of the biasing transistor is equivalent to a minimum value of an absolute value of a voltage between a gate and a source that is necessary for making the biasing transistor into a conductive state.

According to the present invention, there is provided a semiconductor device, characterized in that a photoelectric conversion element is connected to the input terminal.

According to the present invention, there is provided a semiconductor device, characterized in that a signal generated by a photoelectric conversion element is fed to the input terminal.

According to the present invention, there is provided a semiconductor device, characterized in that the photoelectric conversion element is either an X-ray sensor or an infrared sensor.

According to the present invention, there is provided a semiconductor device, characterized in that the photoelectric conversion element is any one of a photo diode, a Schottky diode, an avalanche diode, or a photo conductor.

According to the present invention, there is provided a semiconductor device, characterized in that the photo diode is one of a type incorporating a PN type, a PIN type, or an NPN embedded type.

According to the present invention, there is provided a semiconductor device, characterized in that the semiconductor device has a resetting transistor, and a source terminal or a drain terminal of the resetting transistor is connected to the photoelectric conversion element.

According to the present invention, there is provided a semiconductor device, characterized in that when the semiconductor device has a plurality of biasing transistors, an absolute value of a voltage between a gate and a source of the plurality of biasing transistors is equivalent to a minimum value of an absolute value of a voltage between a gate and a source that is necessary for making the entire plurality of biasing transistors into a conductive state.

According to the present invention, there is provided a semiconductor device, characterized in that the amplifying transistor, the biasing transistor, and the electric discharging transistor are transistors having the same polarity.

According to the present invention, there is provided a driving method of a semiconductor device having an amplifying transistor, a biasing transistor, an amplifying side power source line, a biasing side power source line, and a bias signal line, characterized in that:

a drain terminal of the amplifying transistor is connected to the amplifying side power source line, a source terminal of the biasing transistor is connected to the biasing side power source line, a source terminal of the amplifying transistor is connected to a drain terminal of the biasing transistor, a gate terminal of the biasing transistor is connected to the bias signal line, a gate terminal of the amplifying transistor serves as an input terminal, and a source terminal of the amplifying transistor serves as an output terminal, and characterized in that the driving method outputs a signal after performing a pre-discharge.

According to the present invention, there is provided a driving method of a semiconductor device having an amplifying transistor, a biasing transistor, an amplifying side power source line, a biasing side power source line, and a bias signal line, characterized in that:

a drain terminal of the amplifying transistor is connected to the amplifying side power source line, a source terminal of the biasing transistor is connected to the biasing side power source line, a source terminal of the amplifying transistor is connected to a drain terminal of the biasing transistor, a gate terminal of the biasing transistor is connected to the bias signal line, a gate terminal of the amplifying transistor serves as an input terminal, and a source terminal of the amplifying transistor serves as an output terminal, and characterized in that the driving method outputs a signal after performing a pre-discharge by making an electric potential of the biasing side power source line close to an electric potential of the amplifying side power source line.

According to the present invention, there is provided a driving method of a semiconductor device having an amplifying transistor, a biasing transistor, an amplifying side power source line, a biasing side power source line, and a bias signal line, an electric discharging transistor, and an electric discharging power source line characterized in that:

a drain terminal of the amplifying transistor is connected to the amplifying side power source line, a source terminal of the biasing transistor is connected to the biasing side power source line, a source terminal of the amplifying transistor is connected to a drain terminal of the biasing transistor, a gate terminal of the biasing transistor is connected to the bias signal line, a gate terminal of the amplifying transistor serves as an input terminal, a source terminal of the amplifying transistor serves as an output terminal, one of the output terminal and the electric discharging power source line is connected to a source terminal of the electric discharging transistor while the other thereof is connected to a drain terminal of the electric discharging transistor, and characterized in that the driving method outputs a signal after performing a pre-discharge by making the electric discharging transistor into a conductive state.

According to the present invention, there is provided a driving method of a semiconductor device, characterized in that a value of an electric potential of the electric discharging power source line takes a value that is between an electric potential of the bias signal line and an electric potential of the biasing side power source line.

According to the present invention, there is provided a driving method of a semiconductor device, characterized in that one terminal of a load capacitance is connected to the output terminal, and the other terminal of the load capacitance is connected to a load capacitance power source line.

According to the present invention, there is provided a driving method of a semiconductor device, characterized in that the electric discharging power source line and the biasing side power source line are to be connected together.

According to the present invention, there is provided a driving method of a semiconductor device, characterized in that at least 2 lines from among the electric discharging power source line, the load capacitance power source line, and the biasing side power source line are to be connected together.

According to the present invention, there is provided a driving method of a semiconductor device, characterized in that the load capacitance power source line is connected to the amplifying side power source line.

According to the present invention, there is provided a driving method of a semiconductor device, characterized in that the driving method of a semiconductor device has at least one selecting switch for controlling an electric current flowing to the load capacitance or the output terminal from the amplifying side power source line or from the biasing side power source line.

According to the present invention, there is provided a driving method of a semiconductor device, characterized in that the driving method of a semiconductor device has at least one selecting switch for controlling an electric current flowing to the output terminal from the amplifying side power source line or from the biasing side power source line.

According to the present invention, there is provided a driving method of a semiconductor device, characterized in that the selecting switch has at least one of an N channel transistor or a P channel transistor.

According to the present invention, there is provided a driving method of a semiconductor device, characterized in that an absolute value of a voltage between a gate and a source of the biasing transistor is equivalent to a minimum value of an absolute value of a voltage between a gate and a source that is necessary for making the biasing transistor into a conductive state.

According to the present invention, there is provided a driving method of a semiconductor device, characterized in that a photoelectric conversion element is connected to the input terminal.

According to the present invention, there is provided a driving method of a semiconductor device, characterized in that a signal generated by a photoelectric conversion element is fed to the input terminal.

According to the present invention, there is provided a driving method of a semiconductor device, characterized in that the photoelectric conversion element is either an X-ray sensor or an infrared sensor.

According to the present invention, there is provided a driving method of a semiconductor device, characterized in that the photoelectric conversion element is any one of a photo diode, a Schottky diode, an avalanche diode, or a photo conductor.

According to the present invention, there is provided a driving method of a semiconductor device, characterized in that the photo diode is any one of a type incorporating a PN type, a PIN type, or an NPN embedded type.

According to the present invention, there is provided a driving method of a semiconductor device, characterized in that the driving method of a semiconductor device has a resetting transistor, and the resetting transistor resets the photoelectric conversion element.

According to the present invention, there is provided a driving method of a semiconductor device, characterized in that when the driving method of a semiconductor device has a plurality of biasing transistors, an absolute value of a voltage between a gate and a source of the plurality of biasing transistor is equivalent to a minimum value of an absolute value of a voltage between a gate and a source that is necessary for making the entire plurality of biasing transistors into a conductive state.

According to the present invention, there is provided a driving method of a semiconductor device, characterized in that the amplifying transistor, the biasing transistor, and the electric discharging transistor are transistors having the same polarity.

BRIEF DESCRIPTION OF THE DRAWINGS

The above and other objects and features of the present invention will be more apparent from the following description taken in conjunction with the accompanying drawings:

FIGS. 30A to 30D are diagrams showing manufacturing processes of an image sensor of the present invention;

FIGS. 31A to 31D are diagrams showing manufacturing processes of an image sensor of the present invention;

DETAILED DESCRIPTION OF THE PREFERRED EMBODIMENTS

Embodiment Mode 1

A typical embodiment mode of the present invention is shown in the following.

Figure 11A:
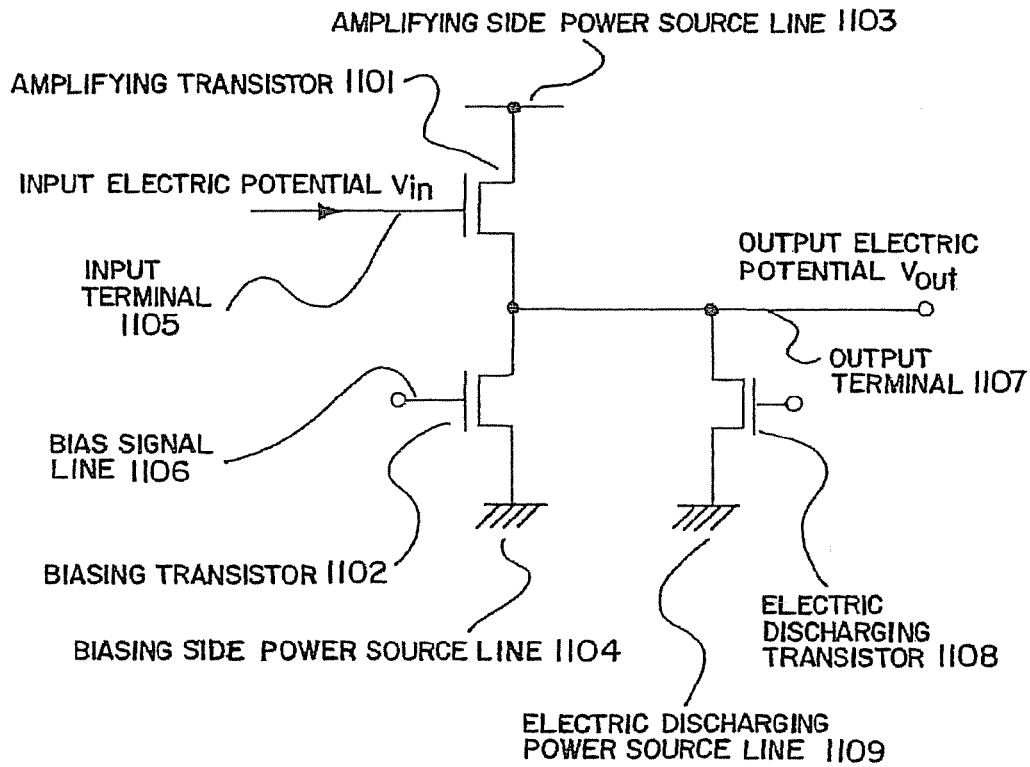
FIGS. 11A and 11B are diagrams showing a circuit configuration and a timing chart, respectively, of a source follower circuit of the present invention.
Figure 11B:
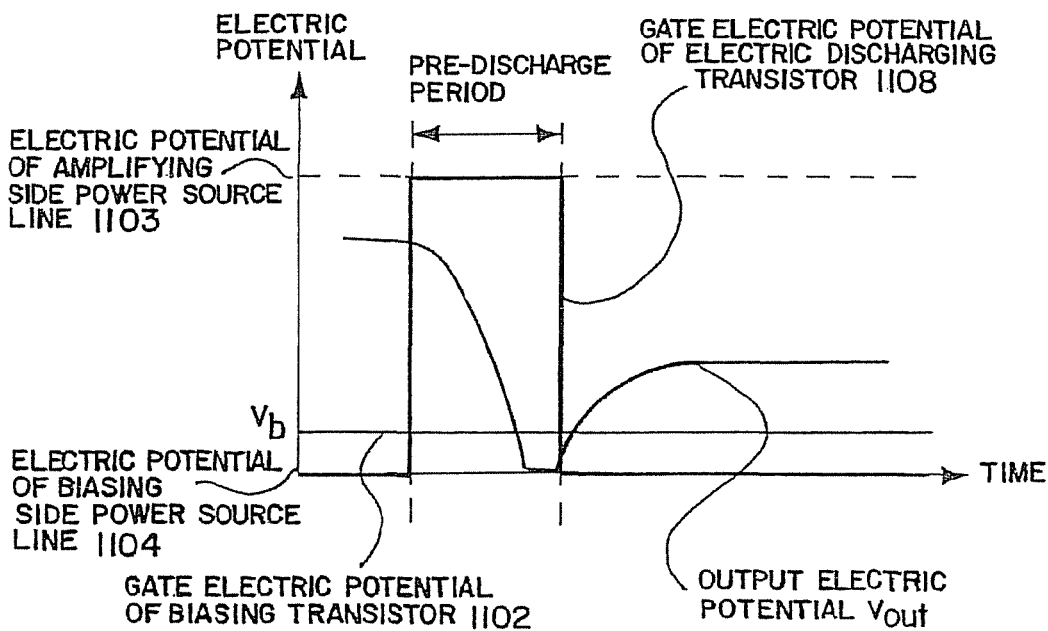

Shown in FIGS. 11A and 11B is an example of a pre-discharge implementation method. FIG. 11A is a diagram showing a circuit configuration of the pre-discharge implementation method, and FIG. 11B is a diagram showing a signal timing chart thereof. In FIGS. 11A and 11B, pre-discharge is performed by arranging an exclusive electric discharging transistor 1108. FIGS. 11A and 11B are diagrams illustrating an example of a case in which an N channel transistor is used to construct the source follower circuit.

An electric potential of a gate terminal of an amplifying transistor 1101 (input terminal 1105) becomes an input electric potential Vin. This input electric potential Vin corresponds to an electric potential of an N channel side terminal of a photo diode. A drain terminal of the amplifying transistor 1101 is connected to an amplifying side power source line 1103, and a source terminal thereof is connected to a drain terminal of a biasing transistor 1102. The source terminal of the amplifying transistor 1101 serves as an output terminal 1107 and an electric potential thereof becomes an output electric potential Vout. A bias electric potential Vb is applied to a gate terminal of the biasing transistor 1102. A source terminal of the biasing transistor 1102 is connected to a biasing side power source line 1104. A source terminal and a drain terminal of the electric discharging transistor 1108 are connected to the output terminal 1107 of the source follower circuit (source terminal of the amplifying transistor 1101) and an electric discharging power source line 1109.

As shown in FIG. 11B, when the electric discharging transistor 1108 is in conductive, the electric potential of the output terminal 1107 becomes the electric potential of the electric discharging power source line 1109 to thereby carry out pre-discharge. During a pre-discharge period, a large electric current can be caused to flow to the electric discharging transistor 1108 because the gate electric potential of the electric discharging transistor 1108 is large. As a result, the output electric potential Vout can be rapidly lowered, whereby the pre-discharge period is shortened. In this method, the bias electric potential Vb may be equivalent to that of the prior art, or may be large.

An actual signal is output after the pre-discharge. In that case, since the source follower circuit is in the Vout<Vin−Vb state, a large electric current flows to the amplifying transistor 1101 as the voltage between the gate and the source thereof is large. Consequently, a signal writing-in can be done in a short time.

Taking the input/output relationship of Vout=Vin−Vb into consideration, it is appropriate to make the bias electric potential Vb as low as possible when outputting the output electric potential Vout in order to increase the output electric potential Vout. However, the biasing transistor 1102 must be in conductive. In other words, the biasing transistor 1102 must be operable in the saturated region and a value in which a fixed electric current can flow therein. Therefore, other than during the pre-discharge period, an optimum value of an absolute value of a bias signal electric potential (voltage between the gate and the source of the biasing transistor) is an electric potential that is slightly higher than an absolute value of a threshold voltage of the biasing transistor 1102.

Further, when the bias electric potential Vb is low, the operating region in which the input/output relationship is linear can be widened because the biasing transistor 1102 can readily operate in the saturated region.

Thus, from the above consequences, it is possible to prevent the signal writing-in time from becoming long, and enlarging the amplitude of the output electric potential and widening the operating region in which the input/output relationship is linear can be realized at the same time.

With regard to the polarity of the electric discharging transistor 1108, the polarity thereof may be similar to those of the amplifying transistor 1101 and the biasing transistor 1102, that is, in FIGS. 11A and 11B, an N channel type. The reason for this resides in that when making the electric discharging transistor 1108 into a conductive, if an N channel type is used to form the electric discharging transistor 1108, then the voltage between the gate and the source thereof can large because the electric potential of the electric discharging power source line 1109 is low. If the polarity of the electric discharging transistor 1108 is different from that of the amplifying transistor 1101 and that of the biasing transistor 1102, that is, in FIGS. 11A and 11B, if a P channel type is used to form the electric discharging transistor 1108, it is necessary to apply an extremely low electric potential to the gate terminal of the electric discharging transistor 1108. In other words, it is necessary to apply an electric potential that is lower than the electric potential of the biasing side power source line 1104. Therefore, from the above explanation, it is desirable to make the polarity of the electric discharging transistor 1108 similar to that of the amplifying transistor 1101 and that of the biasing transistor 1102.

Note that in FIGS. 11A and 11B, a plurality of electric discharging transistors 1108N may be used, in which case transistors of both polarities may be used.

Next, the electric potential of the electric discharging power source line 1109 will be explained. To perform pre-discharge is to set the state of the circuit to Vout<Vin−Vb. Therefore, the electric potential of the electric discharging power source line 1109 has to be set to a low electric potential. The electric potential thereof may be lower than the electric potential of the biasing side power source line 1104. However, since the electric potential operation range of the output terminal 1107 is between the electric potential of the amplifying side power source line 1103 and the electric potential of the biasing side power source line 1104. Even if the electric potential of the electric discharging power source line 1109 is made lower than the electric potential of the biasing side power source line 1104, no improvement is obtained. In the case where the electric potential of the electric discharging power source line 1109 is higher than the electric potential of the biasing side power source line 1104, the state of Vout<Vin−Vb may not be attained if the electric potential of the electric discharging power source line 1109 is made higher than the electric potential of the bias signal line 1106. Thus, from the above explanation, it is necessary that the electric potential of the electric discharging power source line 1109 be set higher than the electric potential of the biasing side power source line 1104 but lower than the electric potential of the bias signal line 1106. Normally, the electric potential of the electric discharging power source line 1109 may be set equivalent to that of the biasing side power source line 1104. Therefore, the electric discharging power source line 1109 and the biasing side power source line 1104 may be connected.

Figure 1A:
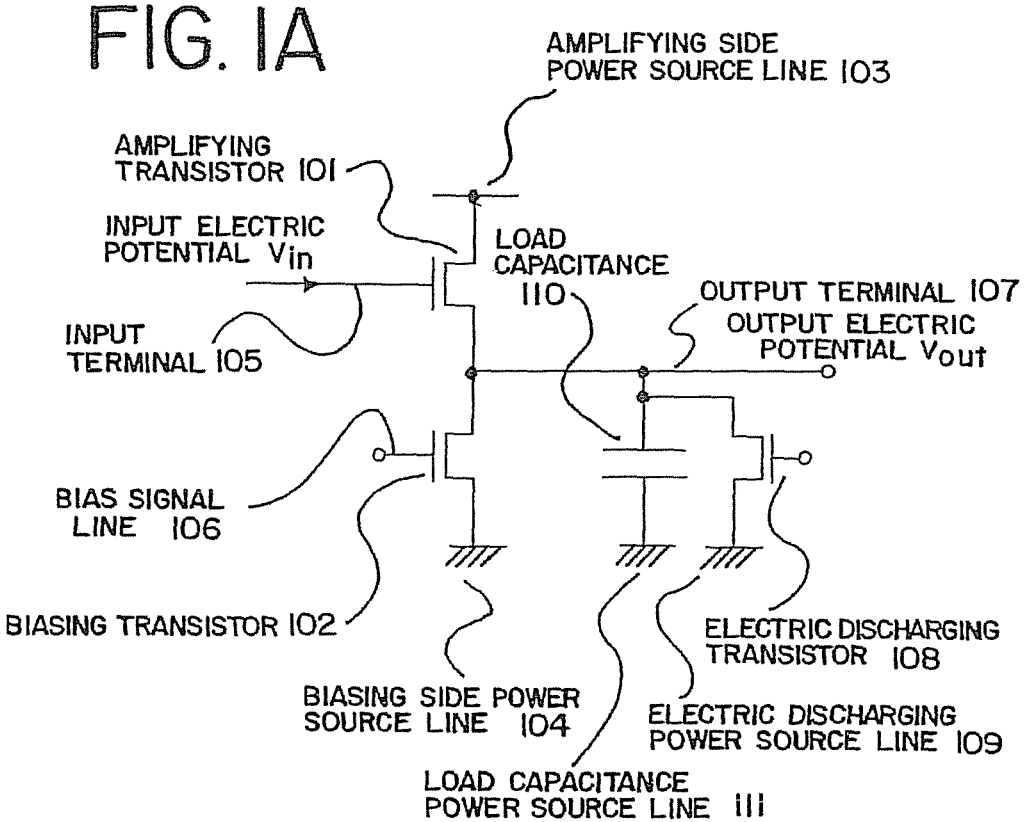
FIGS. 1A and 1B are diagrams showing a circuit configuration and a timing chart, respectively, of a source follower circuit of the present invention.
Figure 1B:
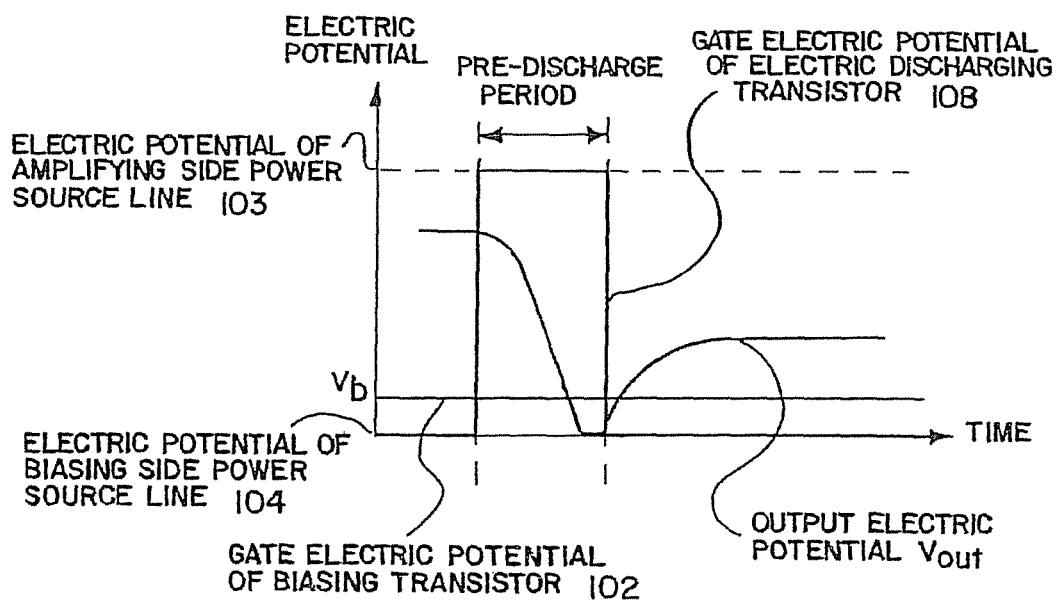
Figure 3:
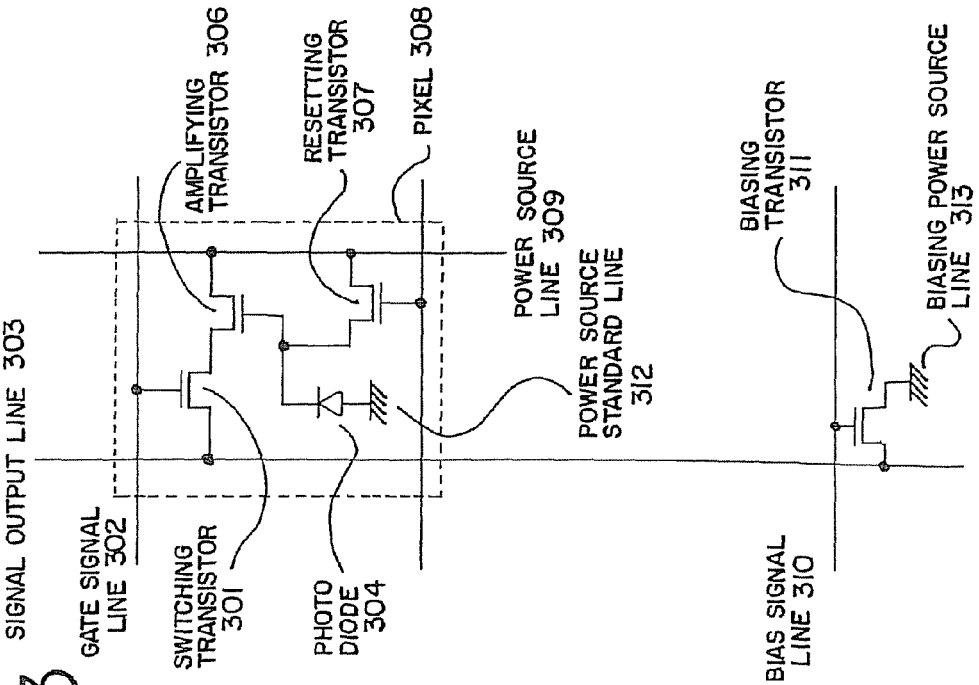
FIG. 3 is a diagram showing a circuit configuration of a pixel of a conventional active sensor.
Figure 2:
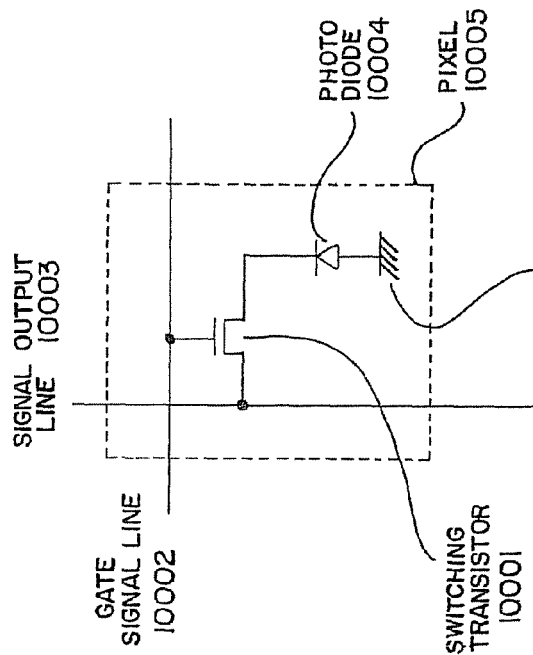
FIG. 2 is a diagram showing a circuit configuration of a pixel of a conventional passive sensor.
Figure 4:
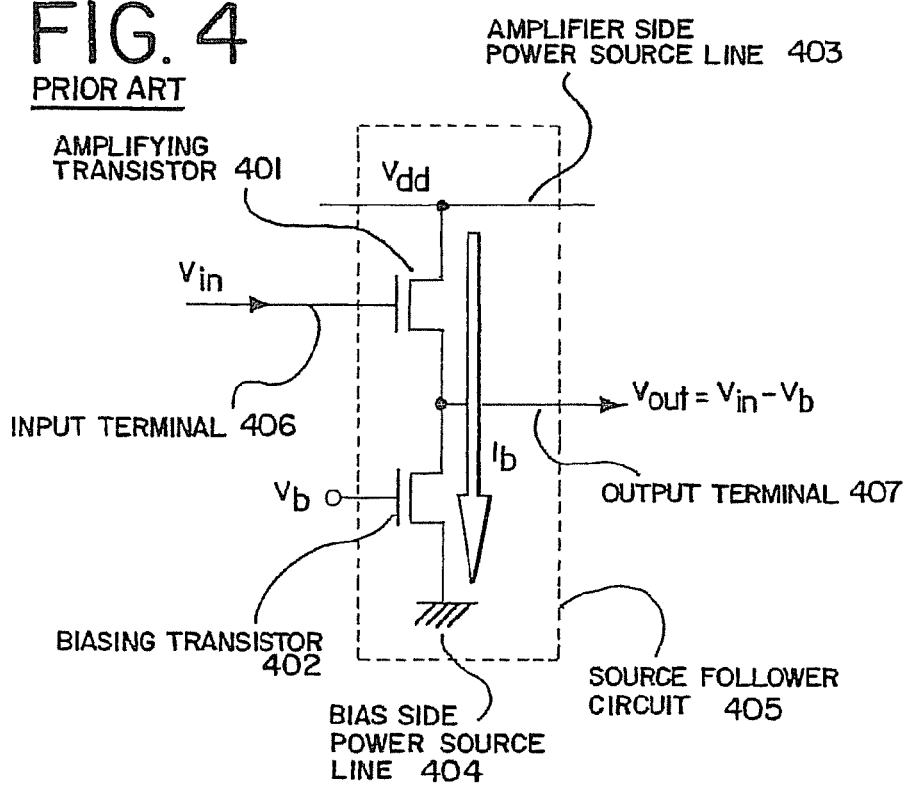
FIG. 4 is a diagram showing a circuit configuration of a conventional source follower circuit.
Figure 5:
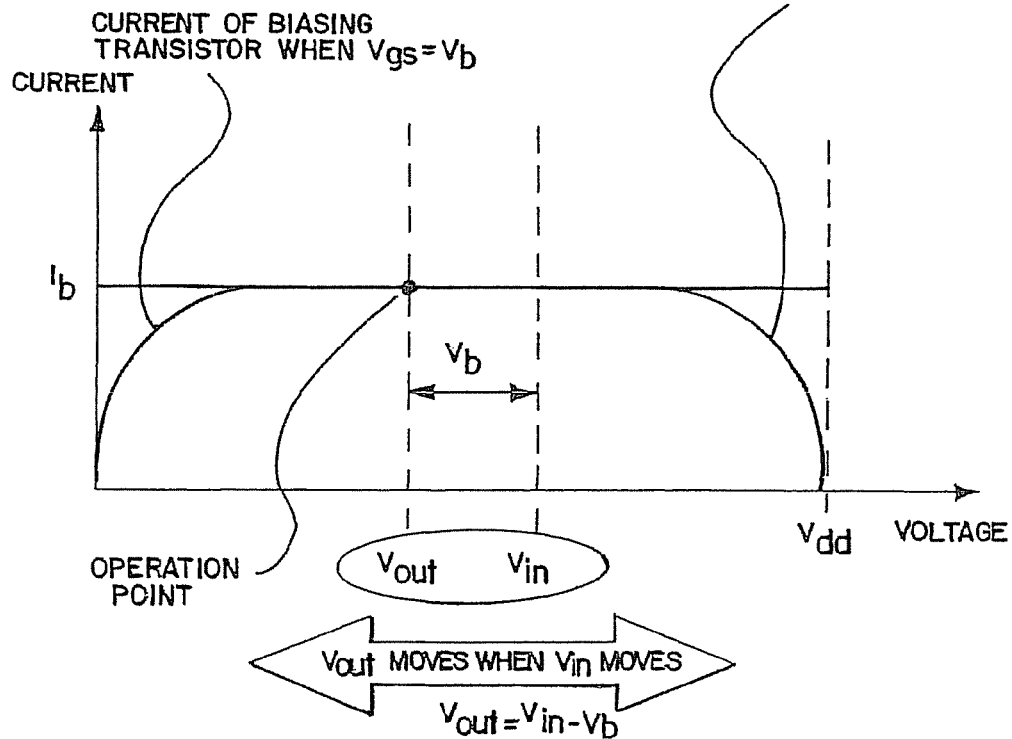
FIG. 5 is a diagram showing an electric current characteristic of a source follower circuit.
Figure 6:
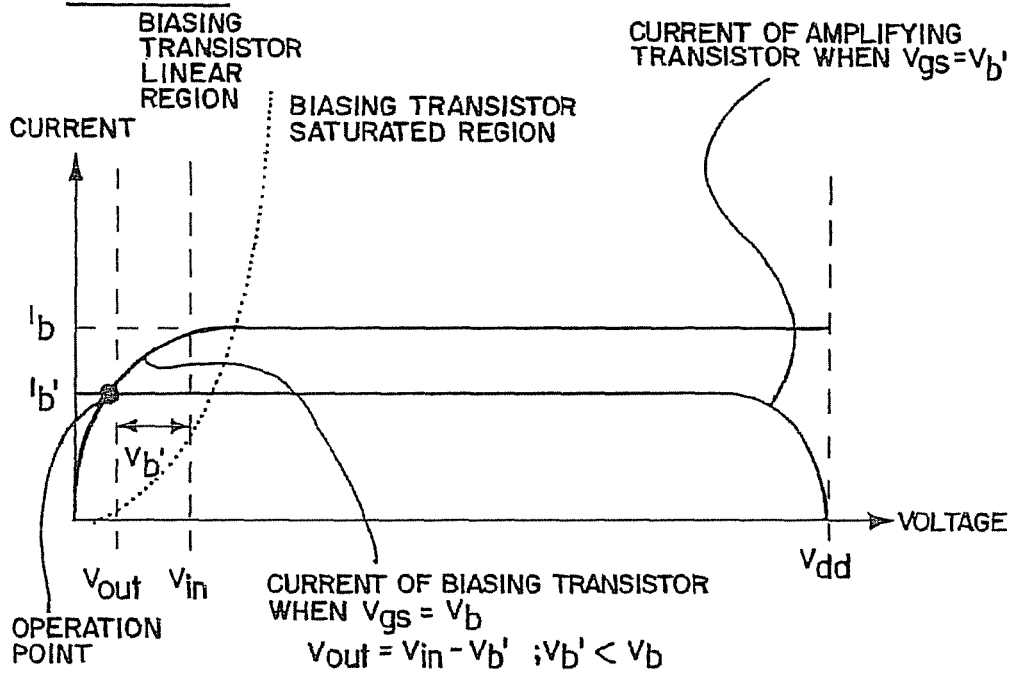
FIG. 6 is a diagram showing an electric current characteristic of a source follower circuit.
Figure 7:
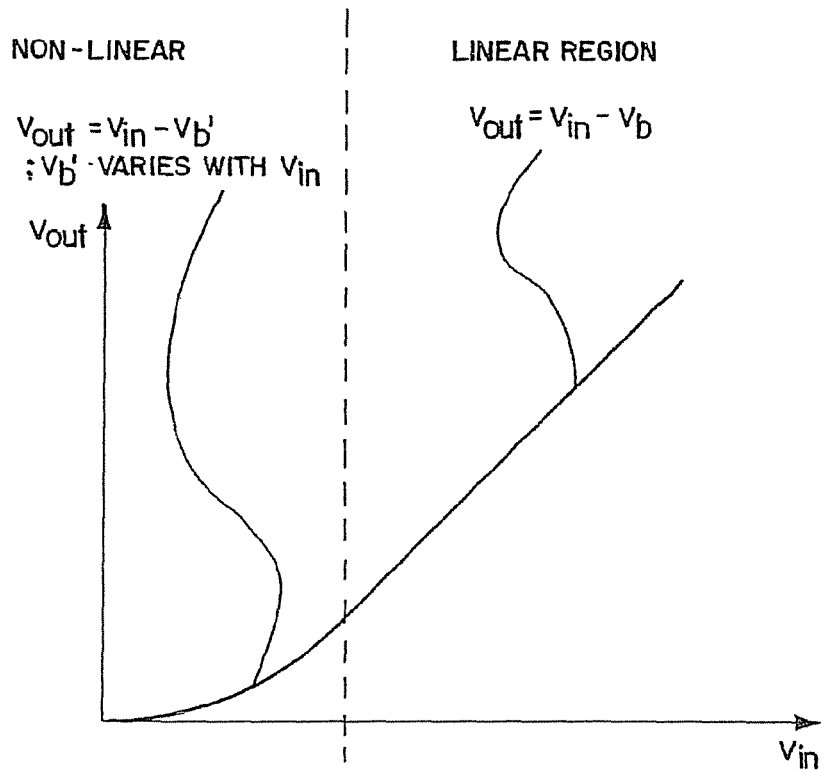
FIG. 7 is a diagram showing an input/output characteristic of a source follower circuit.
Figure 8A:
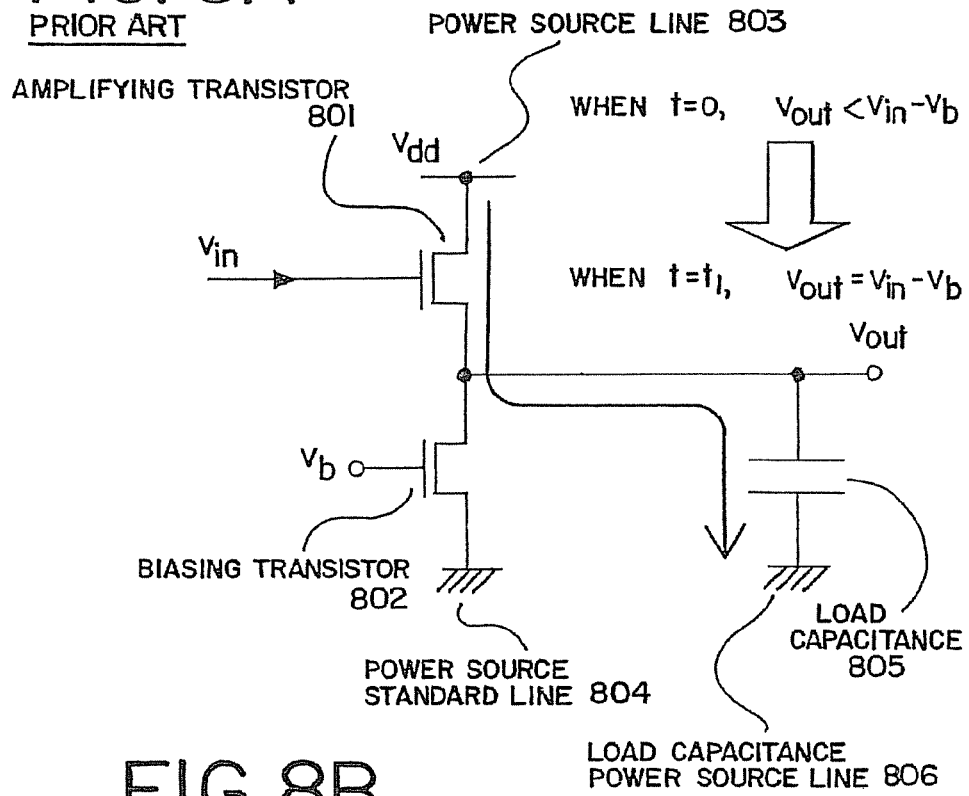
FIGS. 8A and 8B are diagrams showing a circuit configuration and a timing chart, respectively, of a source follower circuit.
Figure 8B:
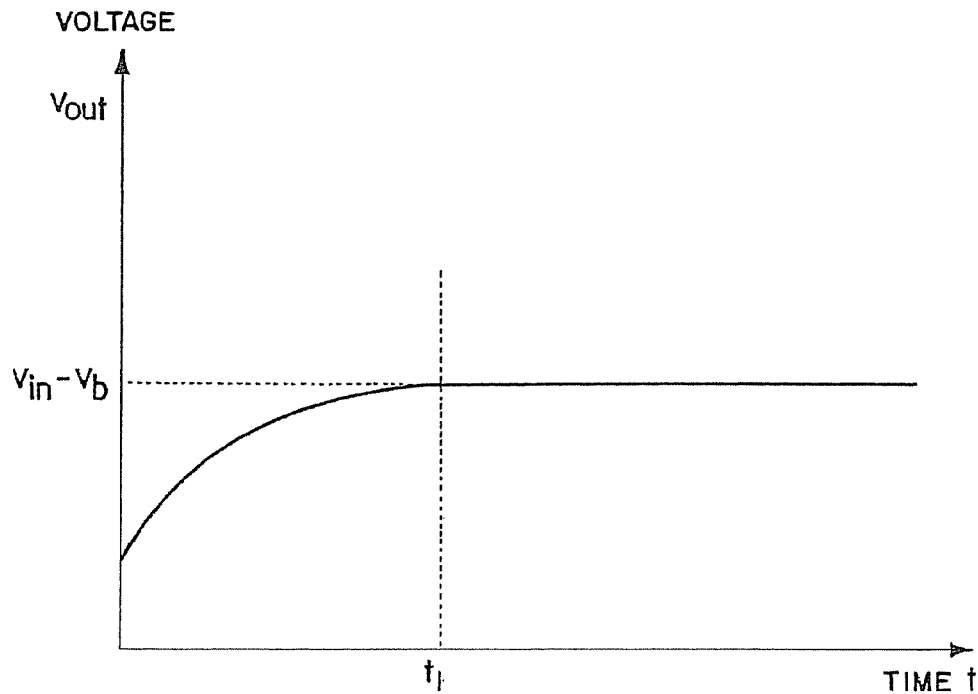
Figure 9A:
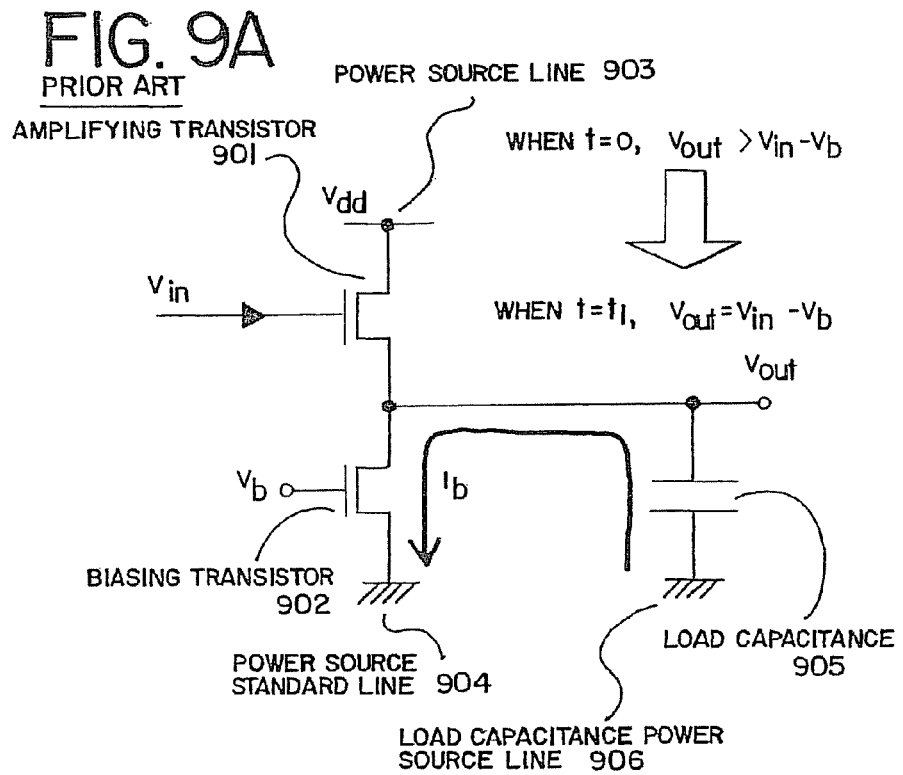
FIGS. 9A and 9B are diagrams showing a circuit configuration and a timing chart, respectively, of a source follower circuit.
Figure 9B:
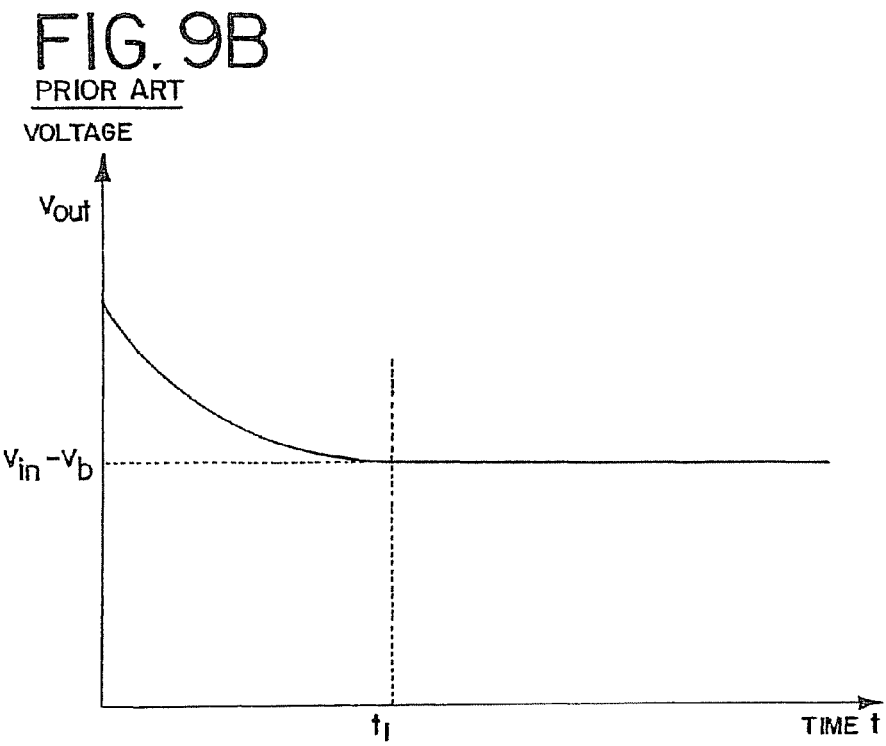
Figure 10:
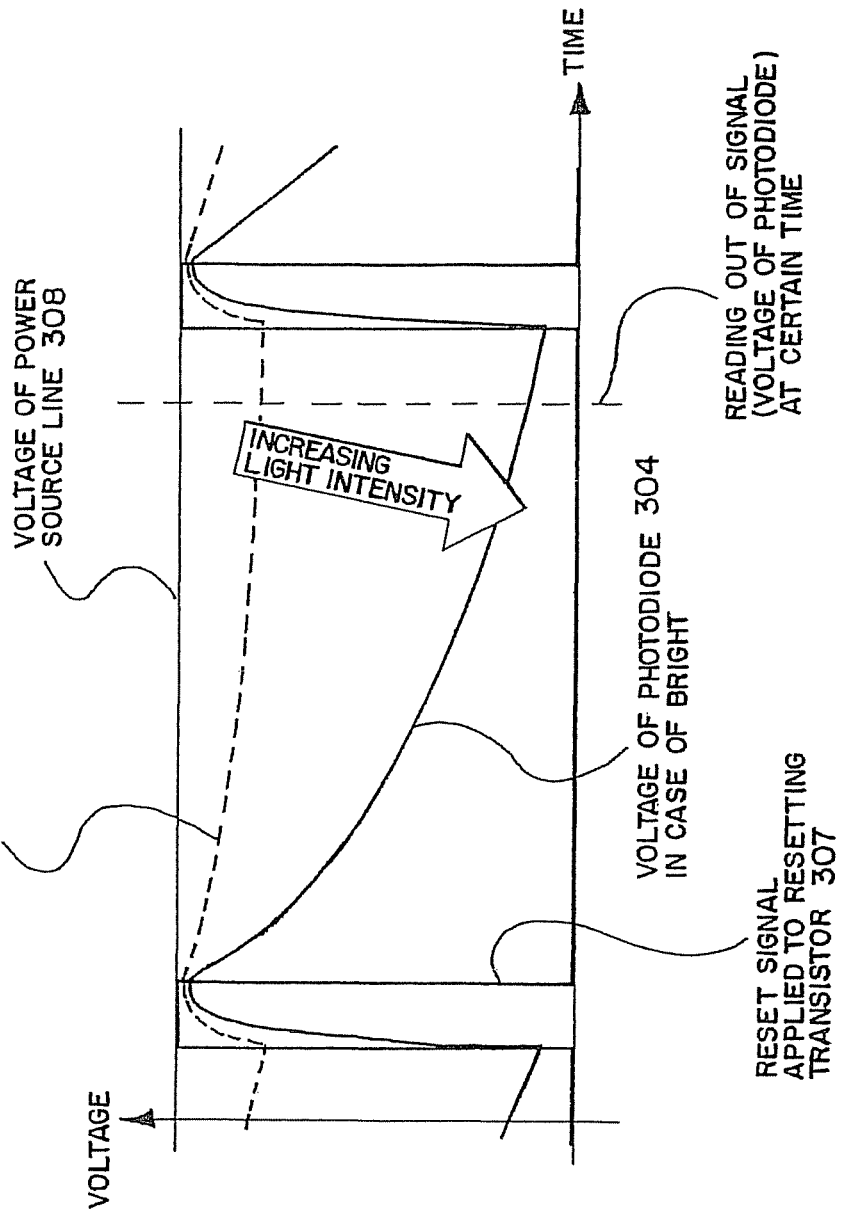
FIG. 10 is a diagram showing a timing chart of an active sensor.
Figure 12A:
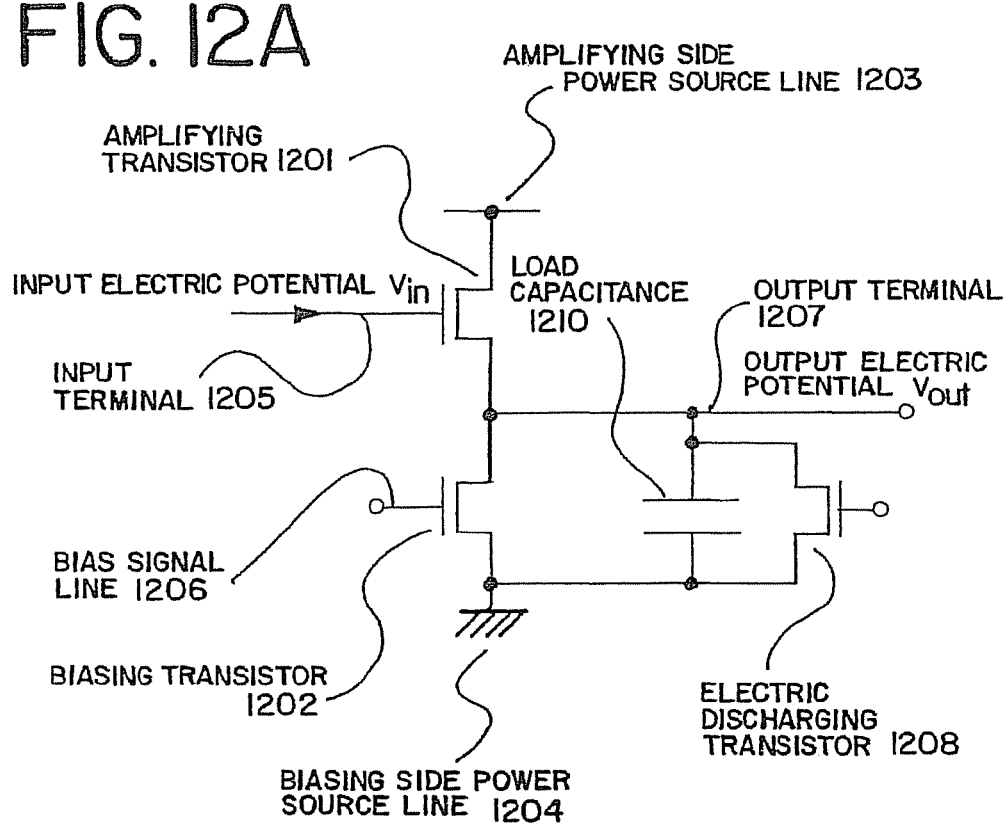
FIGS. 12A and 12B are diagrams showing a circuit configuration and a timing chart, respectively, of a source follower circuit of the present invention.
Figure 12B:
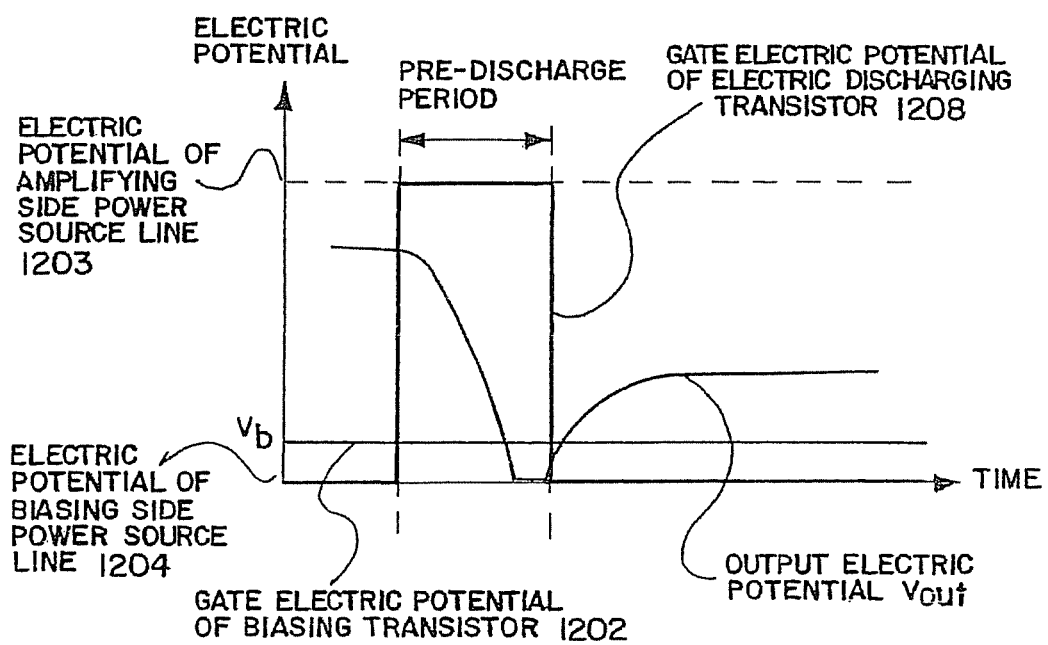

When employing the circuit of FIGS. 11A and 11B in practice, the load capacitance is often connected to the output terminal 1107 to thereby accumulate the signals therein. The diagram of a circuit configuration of a case in which the load capacitance is connected to the circuit illustrated in FIGS. 11A and 11B is shown in FIGS. 1A and 1B. One terminal of a load capacitance 110 is connected to an output terminal 107 whereas the other terminal thereof is connected to a load capacitance power source line 111. The electric potential value of the load capacitance power source line 111 may be an arbitrary value. Normally the electric potential value thereof is often set equivalent to the electric potential of a biasing side power source line 104. Therefore, the load capacitance power source line 111 and the biasing side power source line 104 may be connected. The load capacitance power source line 111 may also be connected with an amplifying side power source line 103. Thus, from the above explanation, 2 lines or more from among the load capacitance power source line 111, the biasing side power source line 104, and the electric discharging power source line 109 may be connected to each other. A circuit configuration and a timing chart of a situation where 3 lines are connected to each other is shown in FIGS. 12A and 12B.

Figure 13A:
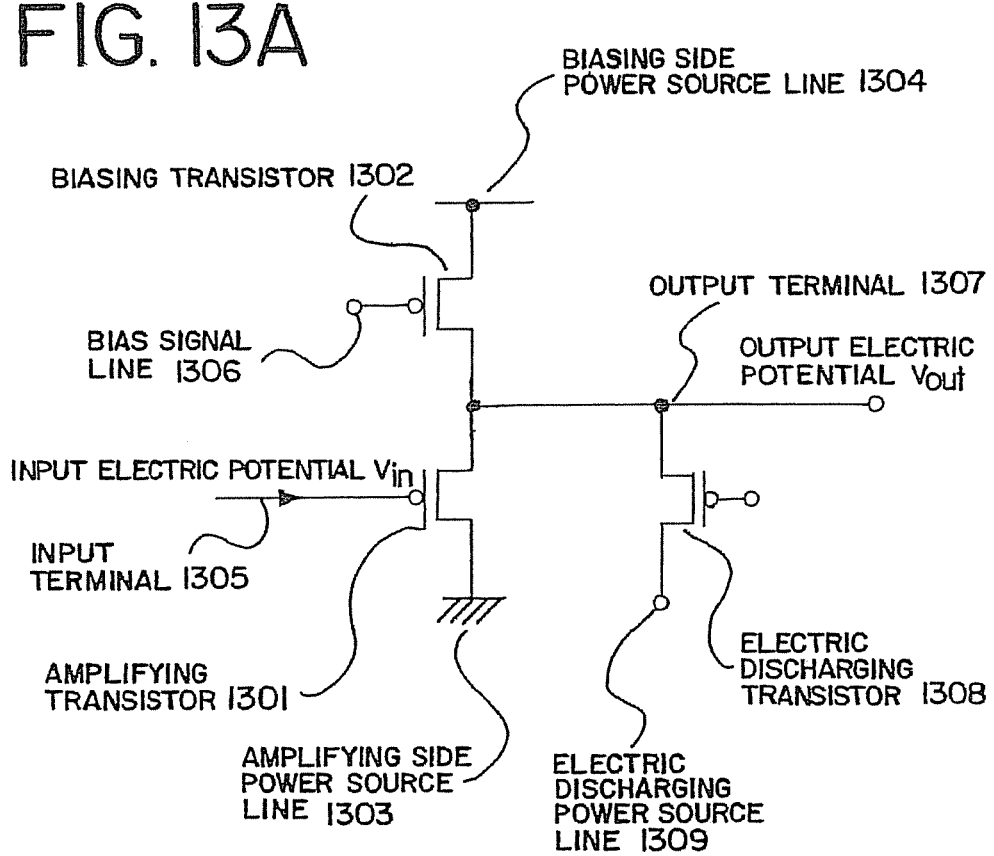
FIGS. 13A and 13B are diagrams showing a circuit configuration and a timing chart, respectively, of a source follower circuit of the present invention.
Figure 13B:
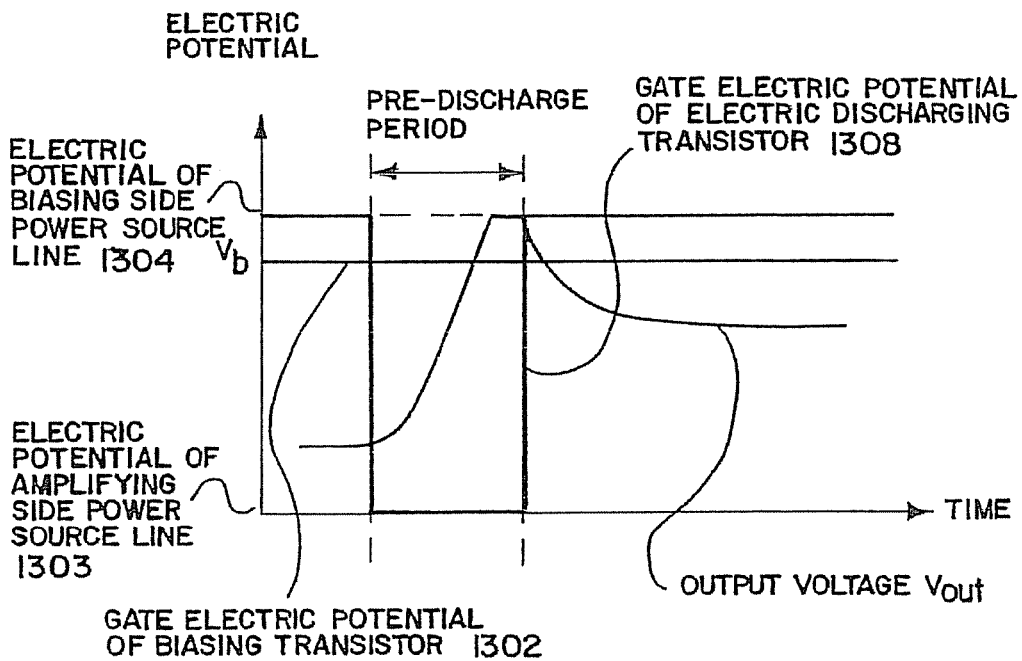
Figure 14A:
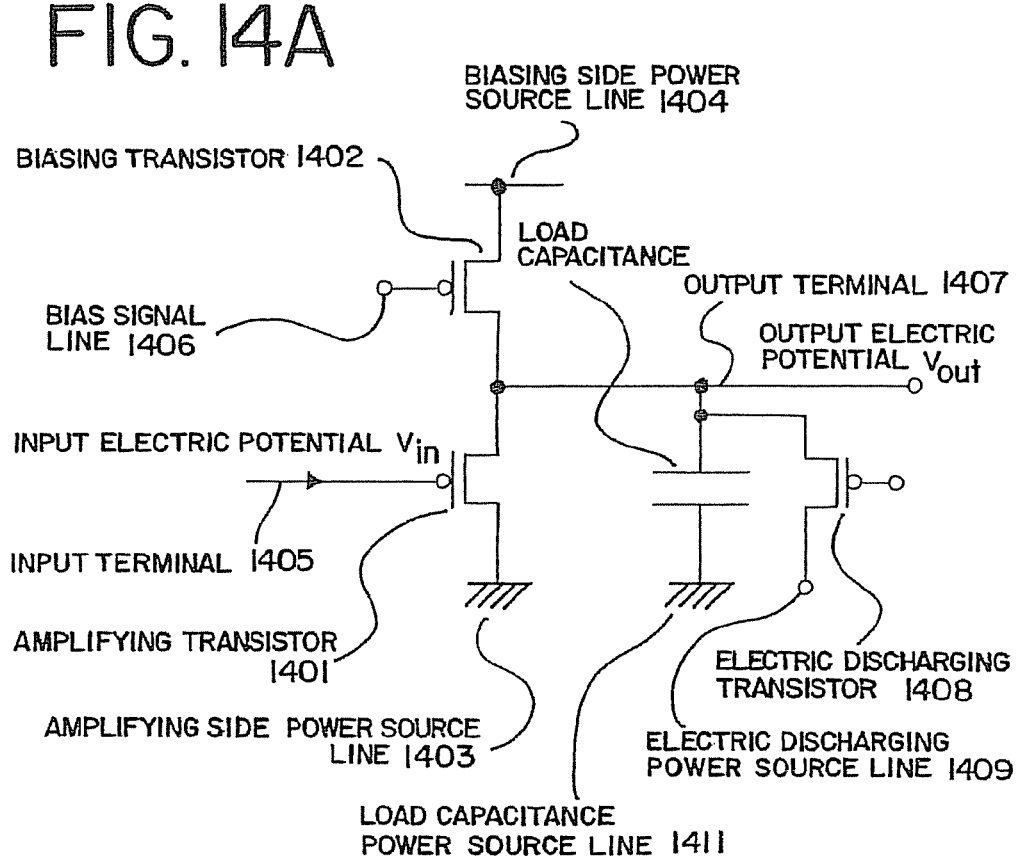
FIGS. 14A and 14B are diagrams showing a circuit configuration and a timing chart, respectively, of a source follower circuit of the present invention.
Figure 14B:
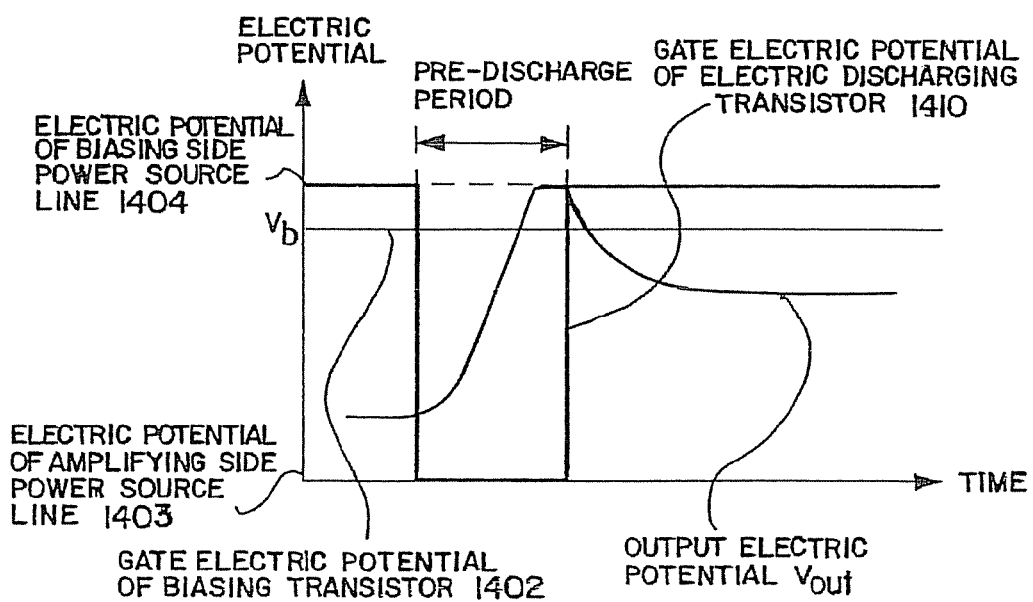
Figure 15A:
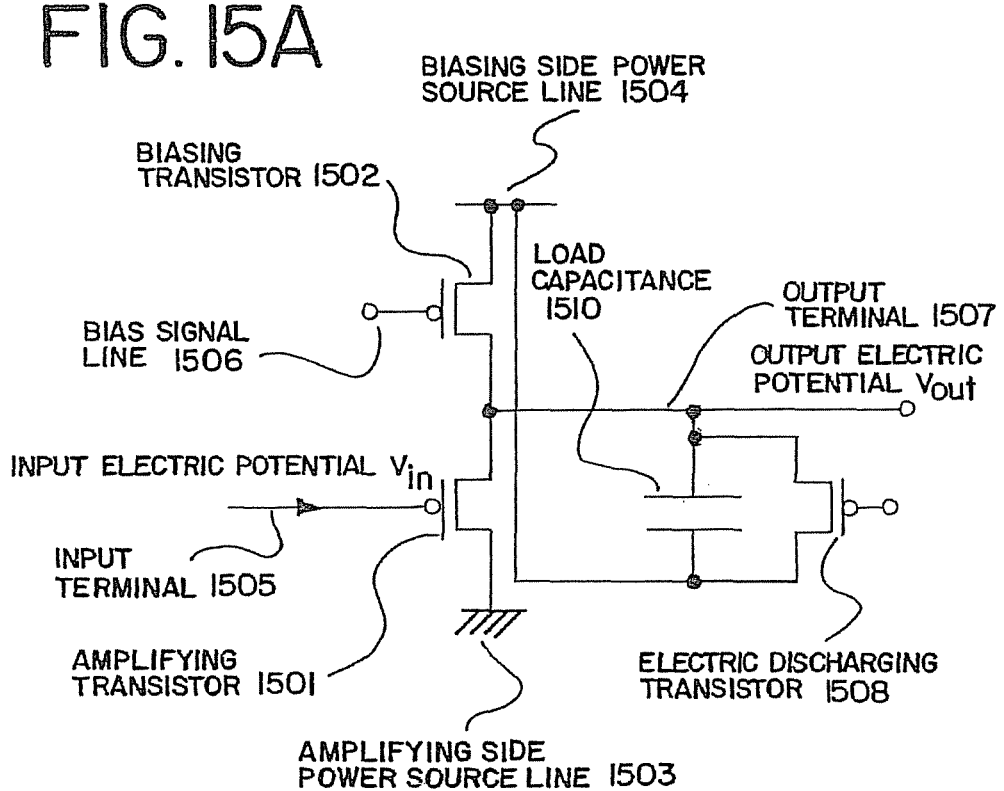
FIGS. 15A and 15B are diagrams showing a circuit configuration and a timing chart, respectively, of a source follower circuit of the present invention.
Figure 15B:
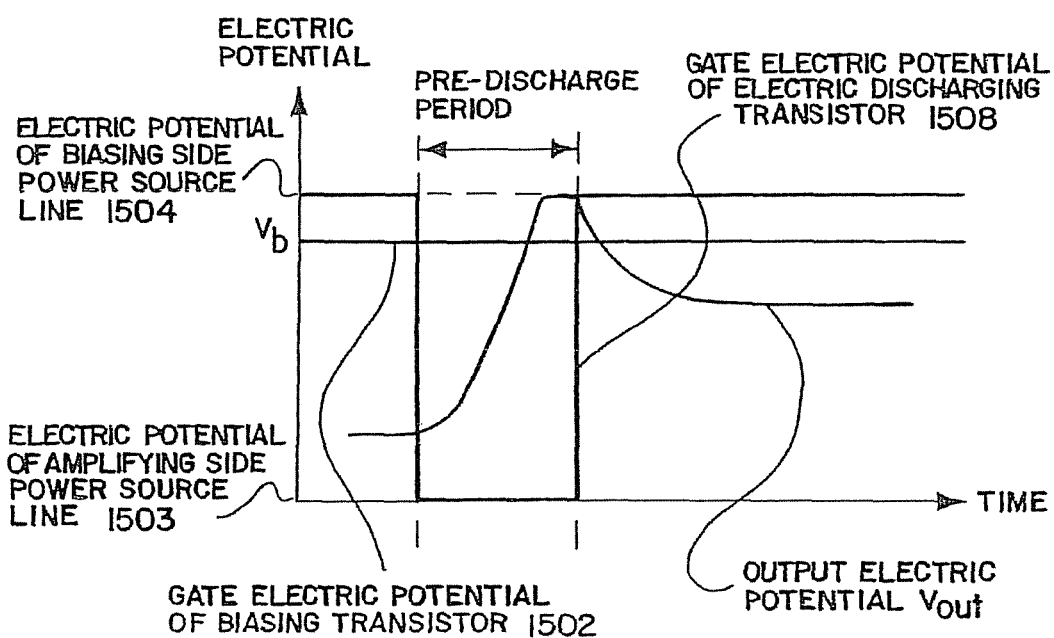

Explanation has been given so far for the case of using an N channel transistor to construct the source follower circuit. However, it is also possible to use a P channel transistor to construct the source follower circuit. Thus, a drawing of circuit configuration using the P channel transistor to construct the source follower circuit will be shown next. The case of using the P channel transistor in the circuit of FIGS. 11A and 11B will be shown in FIGS. 13A and 13B, and a case of using the P channel transistor in the circuit of FIGS. 1A and 1B will be shown in FIGS. 14A and 14B. Shown in FIGS. 15A and 15B is a case of using the P channel transistor in the circuit of FIGS. 12A and 12B. When the N channel transistor is used to construct the source follower circuit, the electric potential of the amplifying side power source line 1103 is higher than the biasing side power source line 1103. However, when the P channel transistor is used to construct the source follower circuit, the electric potential of an amplifying side power source line 1303 is lower than the electric potential of a biasing side power source line 1304.

Figure 16A:
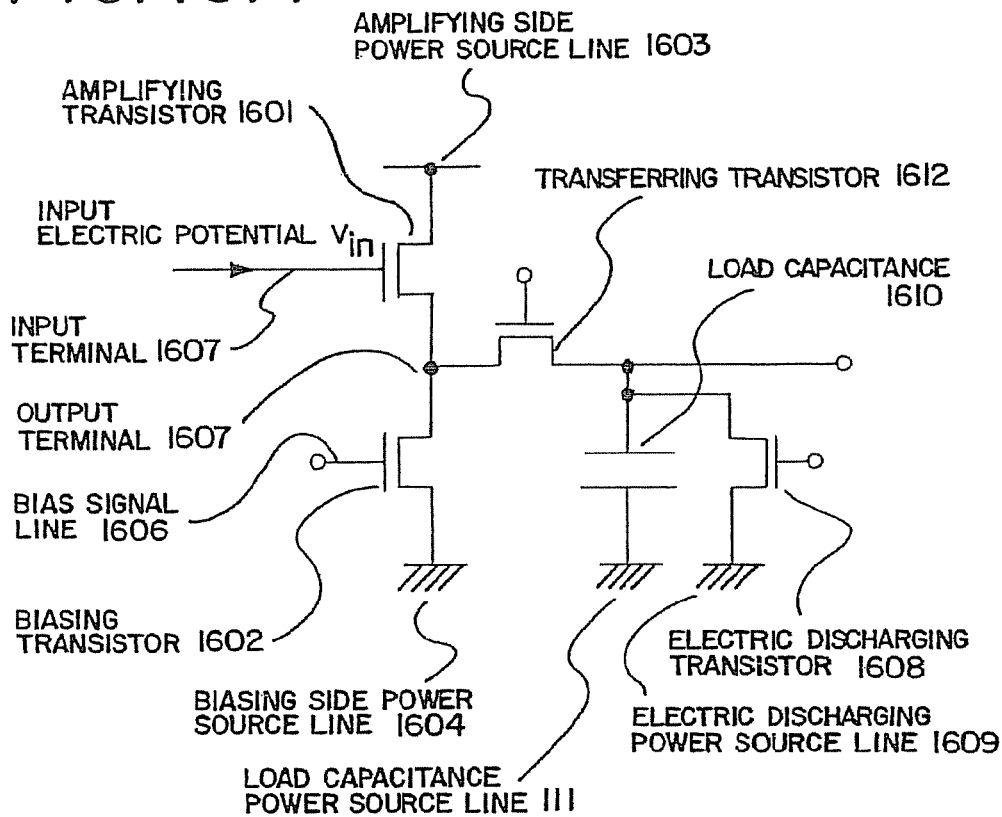
FIGS. 16A and 16B are diagrams showing a circuit configuration and a timing chart, respectively, of a source follower circuit of the present invention.
Figure 16B:
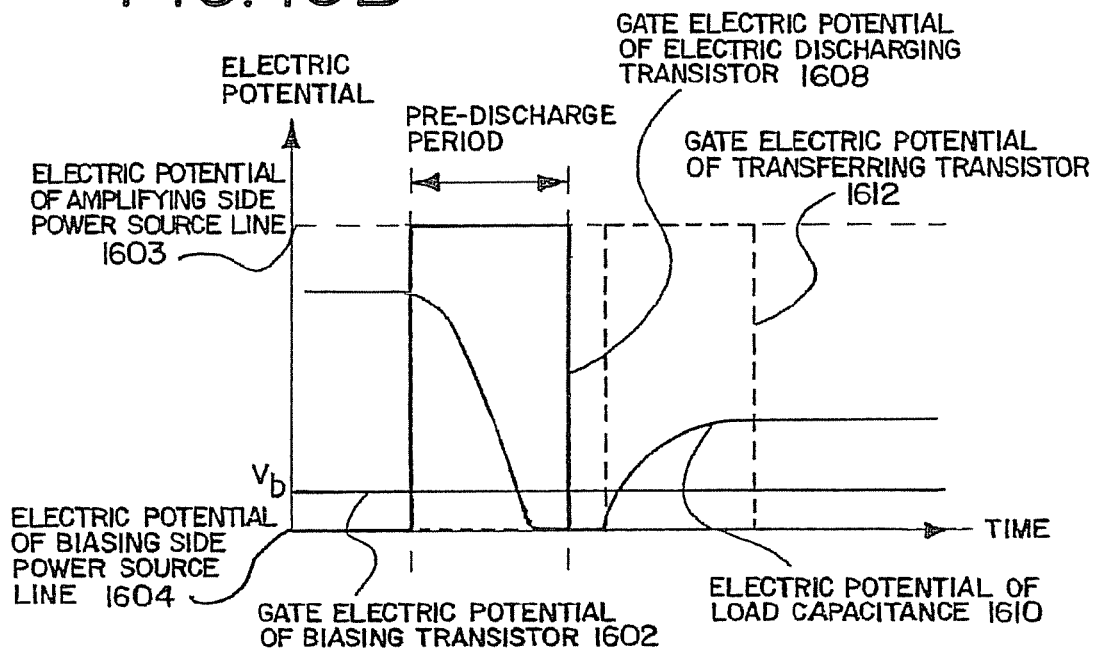
Figure 17A:
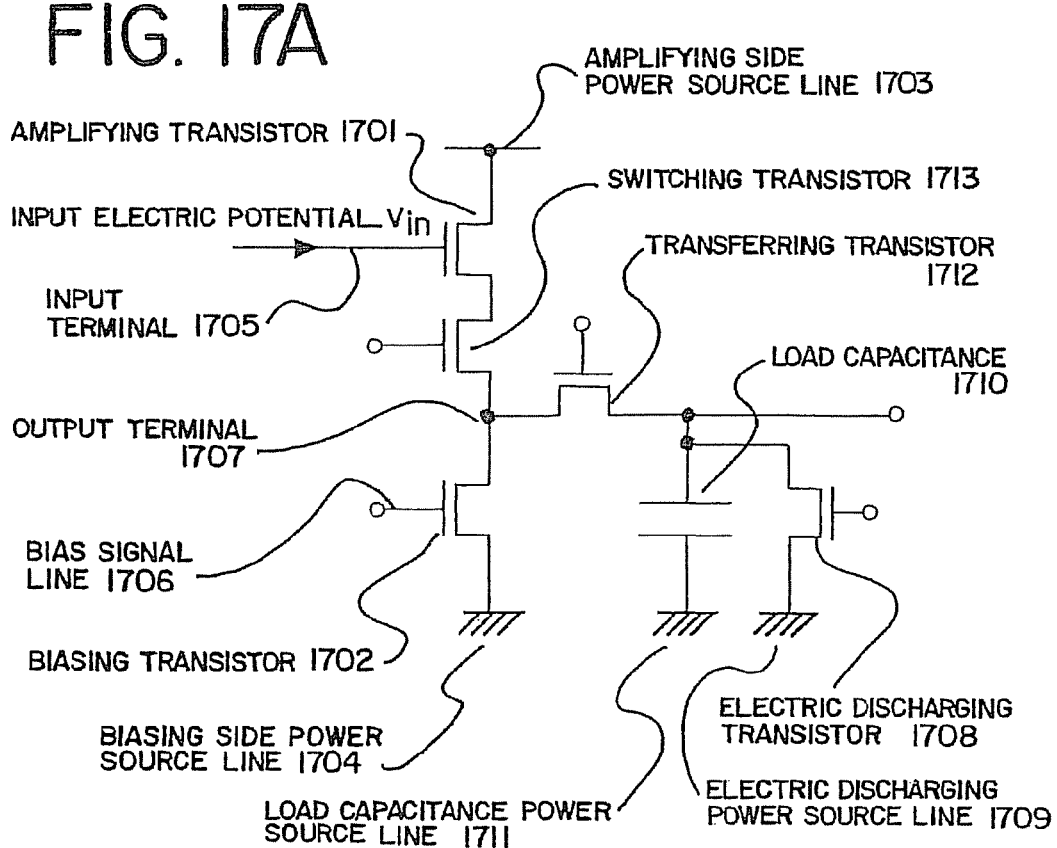
FIGS. 17A and 17B are diagrams showing a circuit configuration and a timing chart, respectively, of a source follower circuit of the present invention.
Figure 17B:
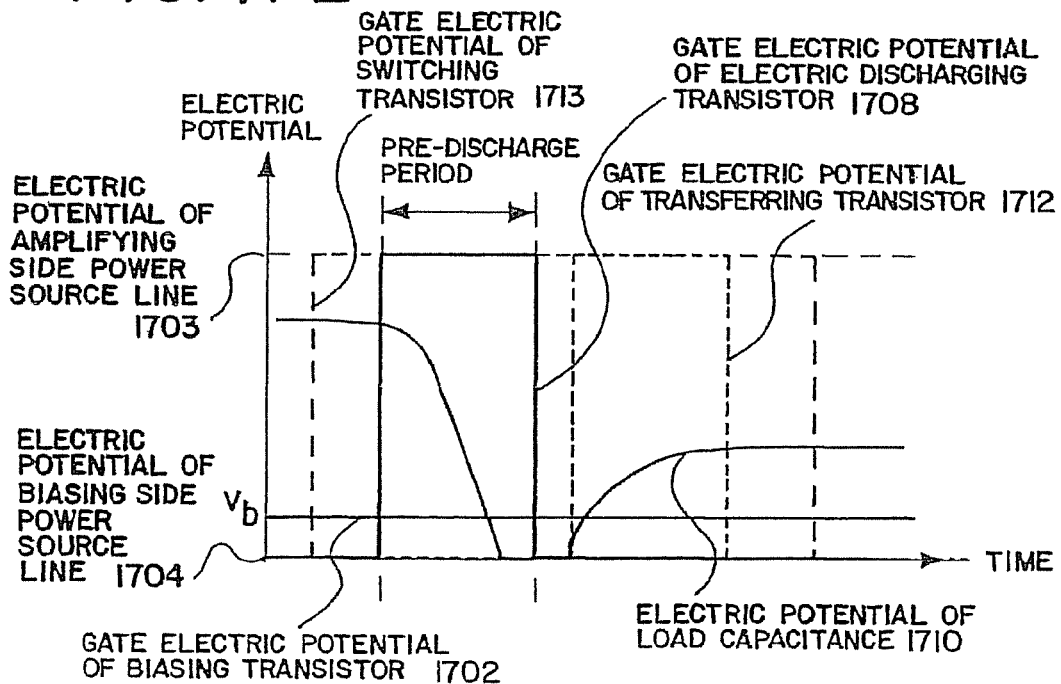

In some cases, a plurality of source follower circuits may be arranged and output terminals may be connected to each other and arranged therein. At that point, there is a necessity to output a signal only from one source follower circuit. Therefore, a switch may be provided to stop the flow of an electric current. The diagrams of a circuit configuration and a timing chart of a case where a transferring transistor 1612 is provided between an output terminal 1607 and a load capacitance 1610 in the circuit of FIGS. 1A and 1B is illustrated in FIGS. 16A and 16B. In the circuit of FIGS. 16A and 16B, a switching transistor 1713 is provided between an output terminal 1707 and an amplifying transistor 1701, and the circuit configuration and timing chart of this case is illustrated in FIGS. 17A and 17B. In FIGS. 16A and 16B or in FIGS. 17A and 17B, at least one element from the amplifying transistor, the biasing transistor, and the selecting switch may be used to construct a unit pixel.

Note that the switch for stopping the flow of an electric current may be formed of either the N channel transistor or the P channel transistor. In addition, a plurality of switches may be provided and the connecting method thereof may be in series or in parallel.

Embodiment Mode 2

Figure 18A:
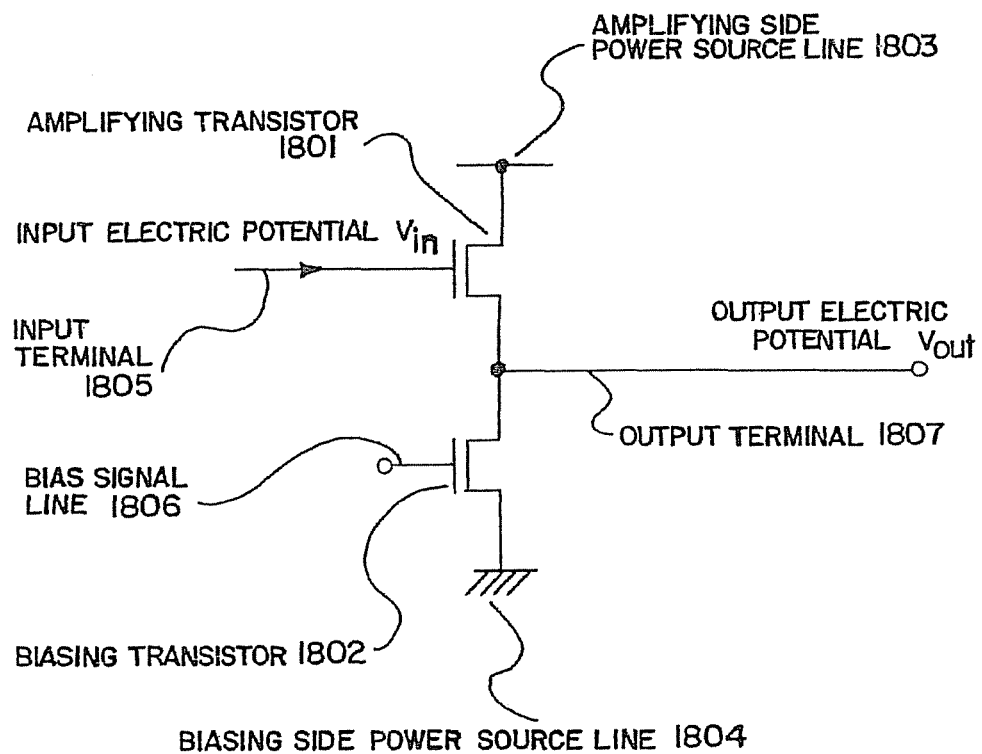
FIGS. 18A and 18B are diagrams showing a circuit configuration and a timing chart, respectively, of a source follower circuit of the present invention.
Figure 18B:
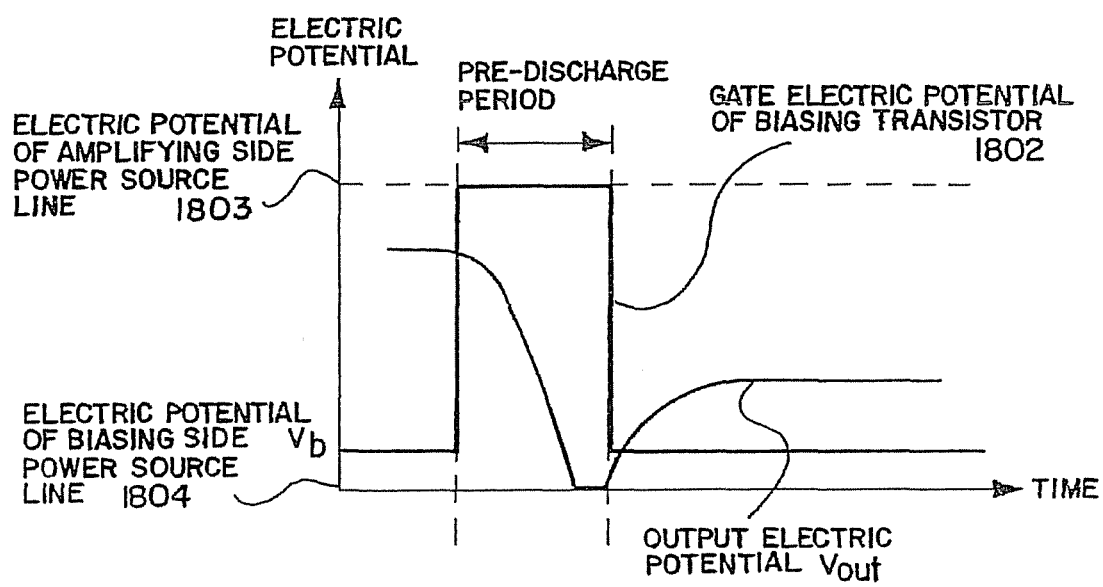

Next, an embodiment mode of a case in which a method of performing the pre-discharge is different from that of Embodiment Mode 1 is shown in FIGS. 18A and 18B. FIG. 18A is a diagram showing a circuit configuration, and FIG. 18B is a diagram showing a signal timing chart. In FIGS. 18A, and 18B, pre-discharge is performed by making the bias electric potential Vb large. Shown in FIGS. 18A and 18B is an example of a case using an N channel transistor to construct the source follower circuit.

An electric potential of a gate terminal of an amplifying transistor 1801 becomes the input electric potential Vin. This input electric potential Vin corresponds to the electric potential of the N channel side terminal of the photo diode. A drain terminal of the amplifying transistor 1801 is connected to an amplifying side power source line 1803, and a source terminal thereof is connected to a drain terminal of a biasing transistor 1802. The source terminal of the amplifying transistor 1801 serves as an output terminal 1807 and an electric potential thereof becomes the output electric potential Vout.

The bias electric potential Vb is applied to a gate terminal of the biasing transistor 1802. A source terminal of the biasing transistor 1802 is connected to a biasing side power source line 1804.

The bias electric potential Vb is increased during the pre-discharge period. As a result, the electric potential of the output terminal 1807 becomes the electric potential of a biasing side power source line 1804 to thereby carry out pre-discharge. During the pre-discharge period, a large electric current can be caused to flow to the biasing transistor 1802 because the gate electric potential of the biasing transistor 1802, that is, the bias electric potential Vb is large. Consequently, the output electric potential Vout can be rapidly lowered, whereby the pre-discharge period is shortened.

An actual signal is output after the pre-discharge. In that case, since the source follower circuit is in the Vout<Vin−Vb state, a large electric current flows to the amplifying transistor 1801 because the electric potential between the gate and the source thereof is large. Consequently, the signal writing-in can be done in a short time.

Taking the input/output relationship of Vout=Vin−Vb into consideration, it is appropriate to make the bias electric potential Vb as low as possible when outputting the output electric potential Vout in order to increase the output electric potential Vout. However, the biasing transistor 1802 must be in conductive. In other words, the biasing transistor 1802 must be operable in the saturated region and set at a value in which a fixed electric current can flow therein. Therefore, other than during the pre-discharge period, an optimum value of an absolute value of a bias signal electric potential (voltage between the gate and the source of the biasing transistor) is an electric potential that is slightly higher than an absolute value of a threshold voltage of the biasing transistor 1802.

Further, when the bias electric potential Vb is low, the operating region in which the input/output relationship is linear can be widened because the biasing transistor 1802 can readily operate in the saturated region.

Thus, from the above consequences, it is possible to prevent the signal writing-in time from becoming long, and enlarging the amplitude of the output electric potential while widening the operating region in which the input/output relationship is linear can be realized at the same time.

Regarding the electric potential value of the bias electric potential Vb during pre-discharge, it is preferable to make the electric potential value thereof as high as possible in order to perform discharge. Therefore, increasing the bias electric potential Vb until it is as high as the highest electric potential in the circuit, for example, the amplifying side power source line 1803, is appropriate.

In the prior art, a fixed electric potential was applied to the bias signal line 1806. In Embodiment Mode 2, the bias electric potential Vb changes during pre-discharge. Therefore, a signal generating device for changing the bias electric potential Vb is connected to the bias signal line 1806.

Figure 19A:
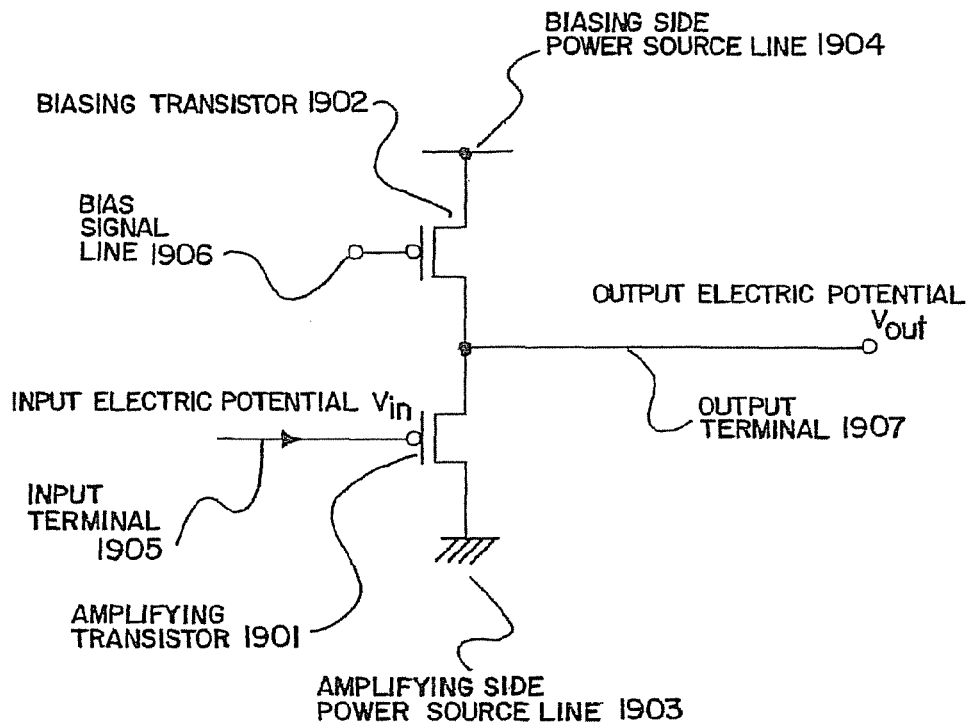
FIGS. 19A and 19B are diagrams showing a circuit configuration and a timing chart, respectively, of a source follower circuit of the present invention.
Figure 19B:
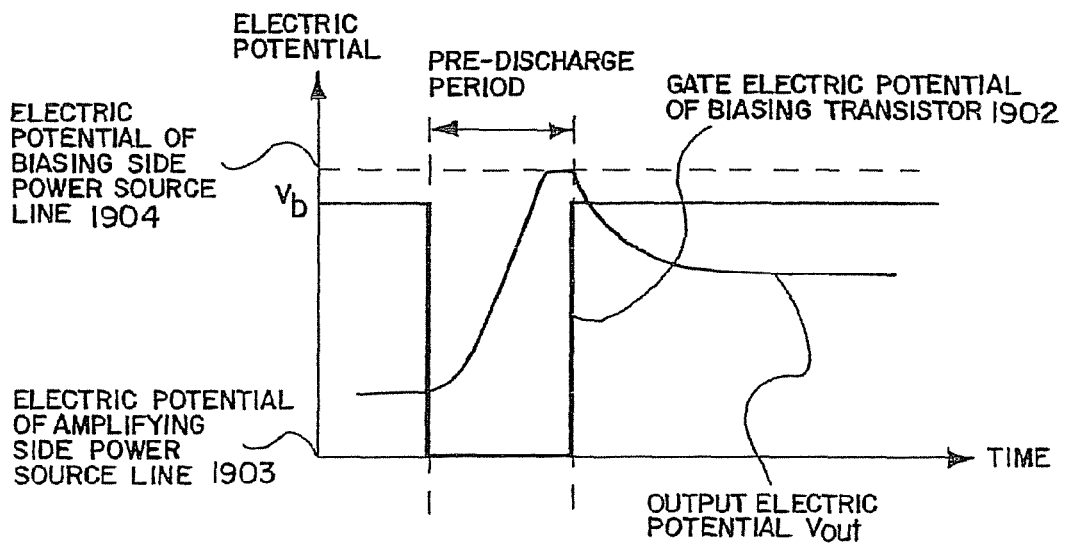

The explanation so far has been about the case of using an N channel transistor to construct the source follower circuit. However, it is also possible to use a P channel transistor to construct the source follower circuit. Thus, a drawing where the P channel transistor is used to construct the source follower circuit is shown in FIGS. 19A and 19B. Similar to Embodiment Mode 1, the relationship concerning the size of the electric potential of the amplifying side power source line and the electric potential of the biasing side power source line is different between the case of using the N channel transistor to construct the source follower circuit and the case of using the P channel transistor to construct the source follower circuit.

Note that similar to Embodiment Mode 1, the provision of a load capacitance and a selecting switch is also possible in Embodiment Mode 2.

Embodiment 1

Figure 20:
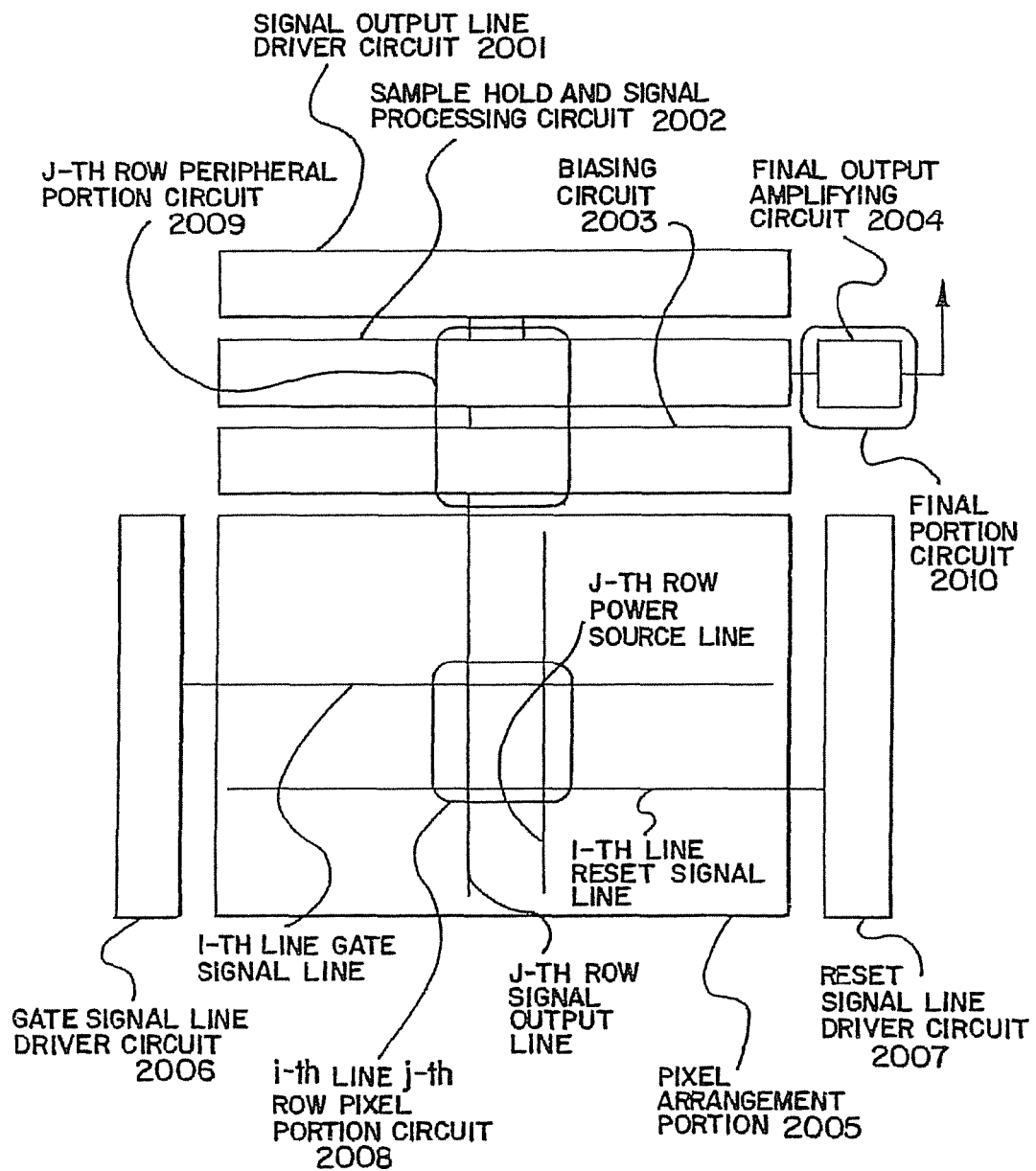
FIG. 20 is a block diagram of an area sensor of the present invention.

An embodiment of a case in which pre-discharge is performed by employing an electric discharging transistor in an area sensor that has pixels arranged two-dimensional therein and incorporated with driver circuits in the periphery thereof will be explained next. The entire circuit configuration is illustrated in FIG. 20. First, there is provided a pixel arrangement portion 2005 having pixels arranged two-dimensional therein. Driver circuits for driving a gate signal line and a reset signal line of each of the pixels is provided on the left and right sides of the pixel arrangement portion 2005. In FIG. 20, a gate signal line driver circuit 2006 is provided on the left side and a reset signal line driver circuit 2007 is provided on the right side. Driver circuits such as a signal processing circuit are arranged above the pixel arrangement portion 2005. A biasing circuit 2003 is arranged above the pixel arrangement portion 2005 in FIG. 20. The biasing circuit 2003 and the amplifying transistors of the respective pixels form the source follower circuit. A sample hold and signal processing circuit 2002 are arranged above the biasing circuit 2003. Circuits for maintaining signals for a time, for performing analog/digital conversion, or for reducing noise are arranged here. A signal output line driver circuit 2001 is arranged above the sample hold and signal processing circuit 2002. The signal output line driver circuit 2001 outputs signals for outputting, in sequence, the signals that have been temporarily preserved. Then, before the signals are output to the outside, a final output amplifying circuit 2004 is arranged thereto. Before the signals, which are sequentially output hereto by the sample hold and the signal processing circuit 2002 and the signal output line driver circuit 2001, are output to the outside, the signals are amplified by the final output amplifying circuit 2004. Therefore, although unnecessary when the signals are not amplified, in practice it is often provided.

Figure 21:
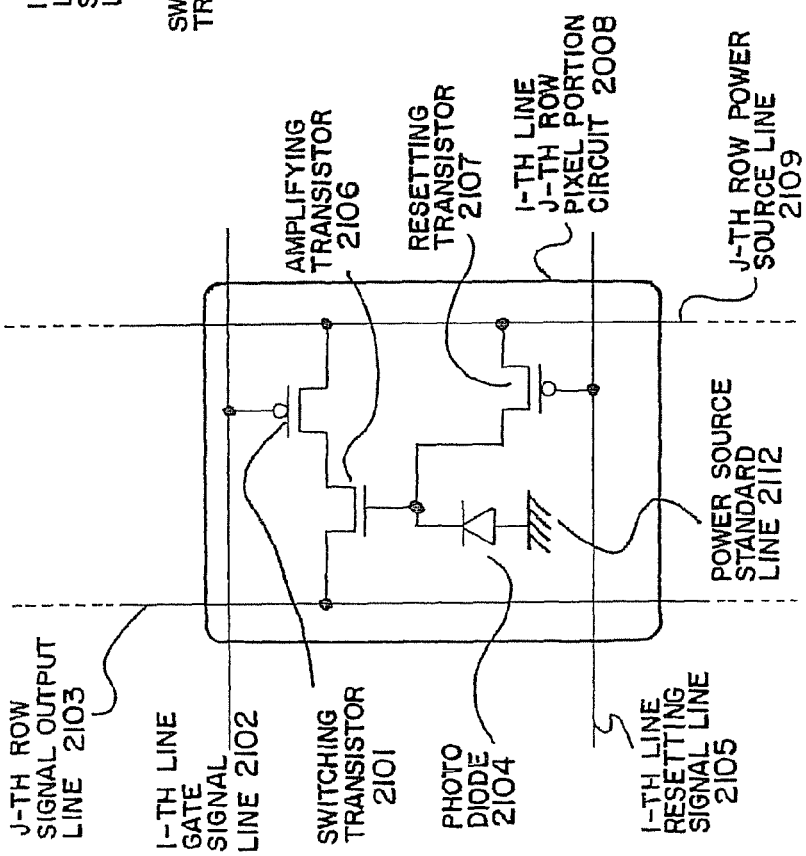
FIG. 21 is a diagram showing a circuit configuration of a pixel of an active sensor of the present invention.

Next, the circuit configuration of the respective portions is illustrated. First, taking an ith line jth row pixel portion circuit 2008 as an example from the interior of the pixel arrangement portion 2005 having pixels arranged in two-dimensional, the circuit configuration thereof is shown in FIG. 21. In FIG. 21, the ith line jth row pixel portion circuit 2008 is composed of a P channel resetting transistor 2107, a P channel switching transistor 2101, an N channel amplifying transistor 2106, and a photoelectric conversion element (here, it is the most typical photo diode 2104). A P channel side terminal of the photo diode 2104 is connected to a power source standard line 2112, and an N channel side terminal thereof is connected to a gate terminal of the amplifying transistor 2106. An ith line resetting signal line 2105 is connected to a gate terminal of the resetting transistor 2107. A source terminal and a drain terminal of the resetting transistor 2107 are connected to a jth row power source line 2109 and to the gate terminal of the amplifying transistor 2106. A gate terminal of the switching transistor 2101 is connected to an ith line gate signal line 2102, and a source terminal and a drain terminal thereof are connected to the jth row power source line 2109 and to the gate terminal of the amplifying transistor 2106. A source terminal and a drain terminal of the amplifying transistor 2106 are connected to a jth row signal output line 2103 and to the switching transistor 2101. As in the prior art, the ith line gate signal line 2102 and the ith line resetting signal line 2105 have their wirings extended in the horizontal direction.

If the wirings of this circuit configuration is made corresponding to the wirings of the source follower circuit, the jth row power source line 2109 corresponds to the amplifying side power source line 1103, the power source standard line 2112 corresponds to the biasing side power source line 1104, and the output terminal 1107 corresponds to the jth row signal output line 2103.

In FIG. 21, the resetting transistor 2107 is formed of the P channel type. However, the resetting transistor 2107 may be formed of the N channel type. Note that, the voltage between the gate and the source of the resetting transistor 2107 cannot be large during the resetting operation in the case the N channel type is used to form the resetting transistor 2107. Accordingly, the resetting transistor will operate in the saturated region, whereby the photo diode 2104 cannot be charged sufficiently. As a result, though the resetting transistor 2107 will operate even if it is formed of the N channel type, it is desirable to use a P channel type.

As for the switching transistor 2101, it is arranged between the ith line power source line 2109 and the amplifying transistor 2106, and is desirably formed of the P channel type as well. However, similar to the prior art, since the switching transistor can operate even if it is formed of N channel type, the N channel type may be used. The switching transistor 2101 may also be provided between the jth row signal output line 2103 and the amplifying transistor 2106. However, because there is difficulty in outputting a signal correctly, the switching transistor 2101 is arranged between the ith line power source line 2109 and the amplifying transistor 2106, and is desirably formed of the P channel type.

As for the amplifying transistor 2106 in FIG. 21, the N channel type is used. Nonetheless, the P channel type may be used. However, in the case of using the P channel type, it is necessary to change the connection method of the circuit in order to combine the amplifying transistor with the biasing transistor to thereby operate as the source follower circuit. That is, in the circuit configuration of FIG. 21, the amplifying transistor 2106 will not operate by simply changing the polarity thereof.

Figure 22:
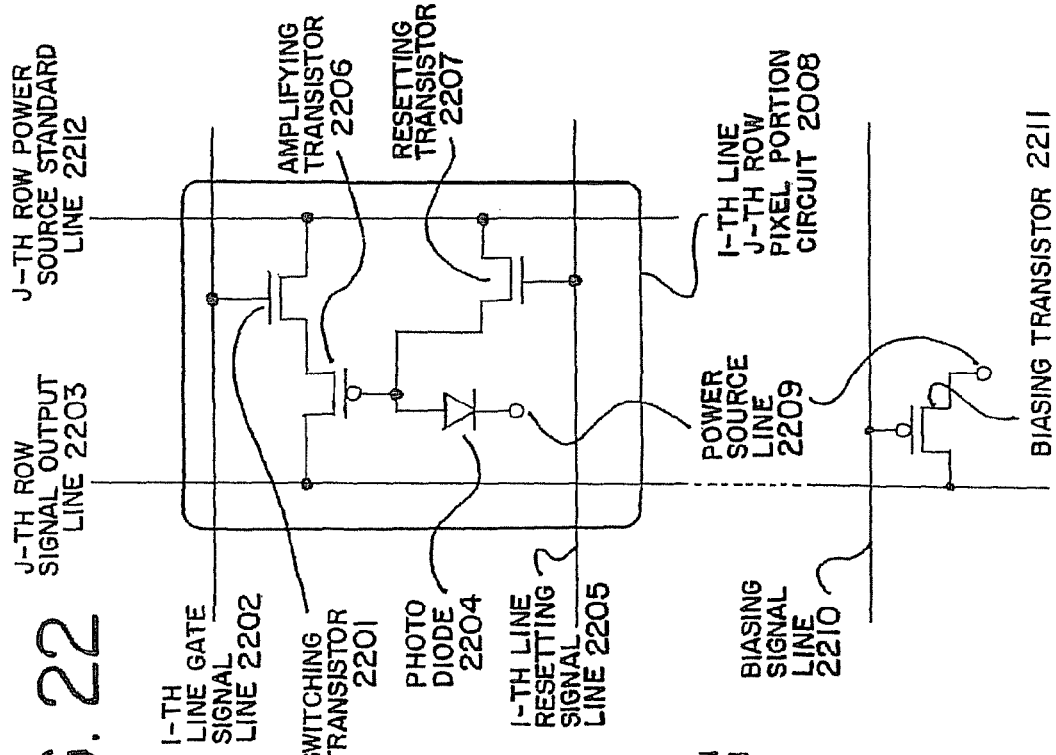
FIG. 22 is a diagram showing a circuit configuration of a pixel of an active sensor of the present invention.

Then, an example of a circuit configuration when a P channel type of amplifying transistor is used is shown in FIG. 22. The differences between this circuit configuration and that of FIG. 21 is that the polarity of an amplifying transistor 2206 is the P channel type, the direction in which the photo diode faces is inverted, and the power source line and the power source standard line are changed. In the case of using the P channel type in the amplifying transistor, it is necessary to use the P channel type in the biasing transistor also. The reason for this resides in that there is a necessity to operate the biasing transistor as a fixed electric current source. Therefore, a description of a biasing transistor 2211 is also made in FIG. 22 for reference. The ith line jth row pixel portion circuit 2008 illustrated in FIG. 22 is composed of an N channel type resetting transistor 2207, an N channel type switching transistor 2201, a P channel type amplifying transistor 2206, and a photoelectric conversion element (here, it is the most typical photo diode 2204). An N channel side terminal of the photo diode 2204 is connected to a power source line 2209, and a P channel side terminal thereof is connected to a gate terminal of an amplifying transistor 2206. An ith line resetting signal line 2205 is connected to a gate terminal of the resetting transistor 2207. A source terminal and a drain terminal of the resetting transistor 2207 are connected to a jth row power source standard line 2212 and to the gate terminal of the amplifying transistor 2206. A gate terminal of the switching transistor 2201 is connected to an ith line gate signal line 2202, and a source terminal and a drain terminal thereof are connected to the jth row power source standard line 2212 and the amplifying transistor 2206. A source terminal and a drain terminal of the amplifying transistor 2206 are connected to a jth row signal output line 2203 and to the switching transistor 2201. A biasing signal line 2210 is connected to a gate terminal of the biasing transistor 2211, and a source terminal and a gate terminal thereof are connected to the jth row signal output line 2203 and to the power source line 2209.

When the wirings of this circuit configuration is made corresponding to the wirings of the source follower circuit, then the jth row power source standard line 2212 corresponds to the amplifying side power source line 1803, the power source line 2109 corresponds to the biasing side power source line 1804, and the output terminal 1807 corresponds to the jth row signal output line 2203.

In FIG. 22, the N channel type is used for the resetting transistor 2207. However, the resetting transistor 2207 may also be formed of the P channel type. However, the voltage between the gate and the source of the resetting transistor 2207 cannot be large during the resetting operation in the case where the P channel type is used to form the resetting transistor 2207. Accordingly, the resetting transistor will operate in the saturated region, whereby the photo diode 2204 cannot be charged sufficiently. As a result, though the resetting transistor 2207 will operate even if the P channel type is used, it is desirable to use the N channel type.

As for the switching transistor 2201 in FIG. 22, it is arranged between the jth row power source standard line 2212 and the amplifying transistor 2206, and desirably is formed of N channel type as well. However, since the switching transistor can operate even if it is formed of the P channel type, the P channel type may also be used. The switching transistor 2201 may also be provided between the jth row signal output line 2203 and the amplifying transistor 2206. However, because there is difficulty in outputting a signal correctly, the switching transistor 2201 is arranged between the jth row power source standard line 2212 and the amplifying transistor 2206, and is desirably formed by using the N channel type.

Thus, as is apparent from the comparison between the circuit configurations of FIGS. 21 and 22, when the polarity of the amplifying transistors is different, the optimal transistor structure also differs.

Figure 23:
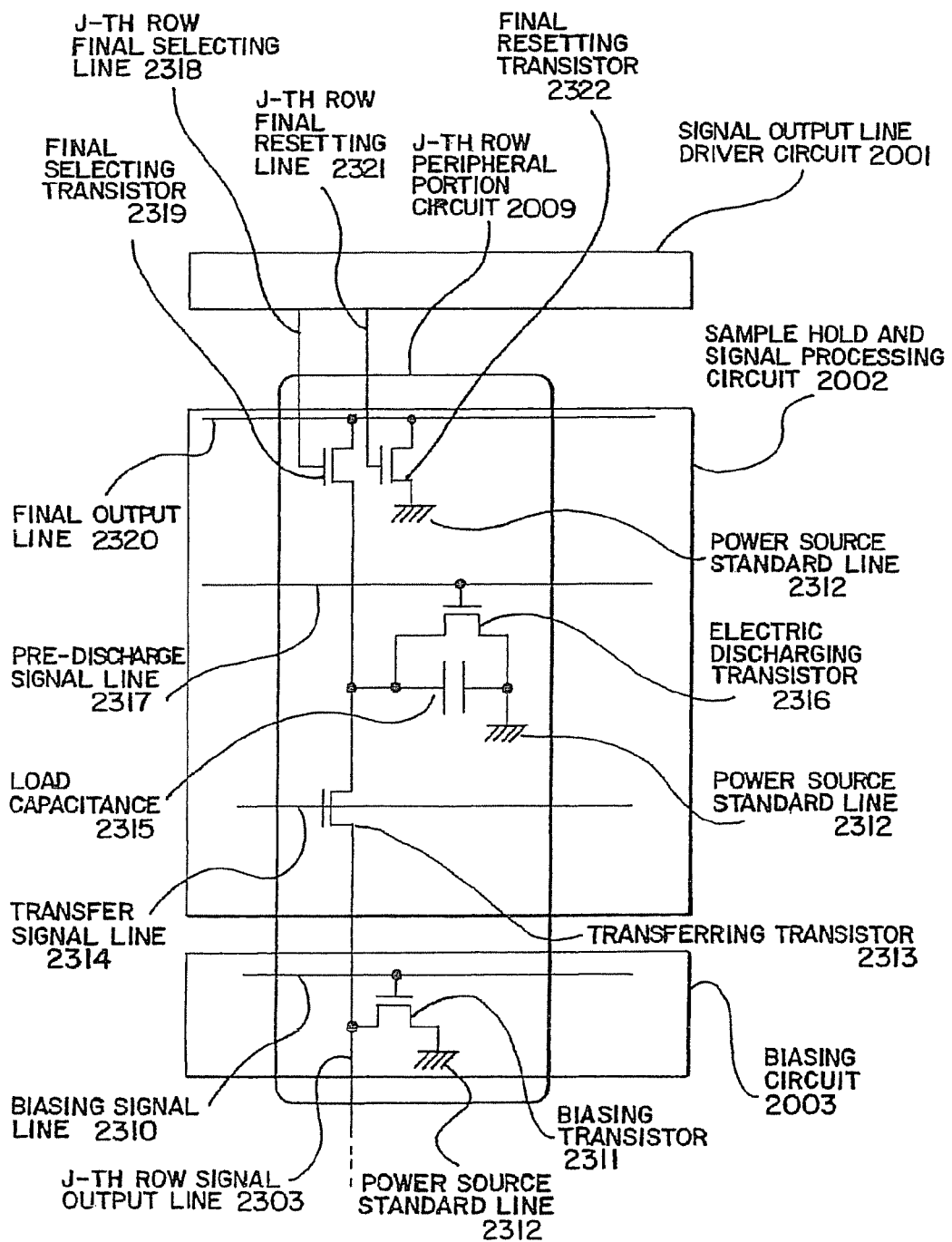
FIG. 23 is a diagram showing a circuit configuration of a signal processing circuit of the present invention.

Next, the circuit configuration of a jth row peripheral portion circuit 2009 taken as an exemplary row of circuits from inside the biasing circuit 2003 and the sample hold and signal processing circuit 2002 is shown in FIG. 23. A biasing transistor 2311 is arranged in the biasing circuit 2003. The polarity thereof is the same as the polarity of the amplifying transistor of the respective pixels. Therefore, if the amplifying transistor of the pixel is the N channel type, the biasing transistor is also the N channel type. In FIG. 23, the biasing transistor 2311 is the N channel type. A gate terminal of the biasing transistor 2311 is connected to a biasing signal line 2310, and a source terminal and a drain terminal thereof are connected to a jth row signal output line 2303 and a power source standard line 2312 (when the biasing transistor is the P channel type, the power source line is used in place of the power source standard line). The biasing transistor 2311 and the amplifying transistors of the respective pixels, operates as the source follower circuit. A gate terminal of a transferring transistor 2313 is connected to a transfer signal line 2314, and a source terminal and a drain terminal thereof are connected to a jth row signal output line 2303 and a load capacitance 2315. The transferring transistor is operated when transferring the electric potential of the signal output line 2303 to the load capacitance 2315. Therefore, a P channel type transferring transistor may be added and connected in a row to an N channel type transferring transistor 2314. The load capacitance 2315 is connected to the transferring transistor 2313 and the power source standard line 2312. The role of the load capacitance 2315 is to temporarily accumulate therein the signals output from the signal output line 2303. A gate terminal of an electric discharging transistor 2316 is connected to a pre-discharge signal line 2317, and a source terminal and a drain terminal thereof are connected to the load capacitance 2315 and the power source standard line 2312. Prior to inputting the electric potential of the signal output line 2303 to the load capacitance 2315, the electric discharging transistor 2316 operates to discharge the electric charges that have temporarily accumulated in the load capacitance 2315.

Note that the analog/digital signal conversion circuit, the noise reduction circuit, etc. may also be arranged therein.

A final selecting transistor 2319 is connected between the load capacitance 2315 and a final output line 2320. A source terminal and a drain terminal of the final selecting transistor 2319 are connected to the load capacitance 2315 and the final output line 2320, and a gate terminal thereof is connected to a jth row final selecting line 2318. The final selecting line will be scanned from the first row in sequence. Then the jth row final selecting line 2318 is selected, and when the final selecting transistor 2319 is turned into conductive, the electric potential of the load capacitance 2315 and that of the final output line 2320 become equivalent. As a result, the signals that have accumulated in the load capacitance 2315 can be output to the final output line 2320. However, if electric charges are accumulated in the final output line 2320 before outputting the signals to the final output line 2320, the electric potential when outputting the signals to the final output line 2320 will be adversely influenced by those electric charges. Therefore, the electric potential of the final output line 2320 must be initialized to a certain electric potential value before the signals are output to the final output line 2320. In FIG. 23, a final resetting transistor 2322 is arranged between the final output line 2320 and the power source standard line 2312. A gate terminal of the final resetting transistor 2322 is connected to a jth row final resetting line 2321. Prior to selecting the jth row final selecting line 2318, the jth row final resetting line 2321 is selected to thereby initialize the electric potential of the final output line 2320 and that of the power source standard line 2312. Thereafter, the jth row final selecting line 2318 is selected, whereby the signals that have accumulated in the load capacitance 2315 are output to the final output line 2320.

Figure 24:
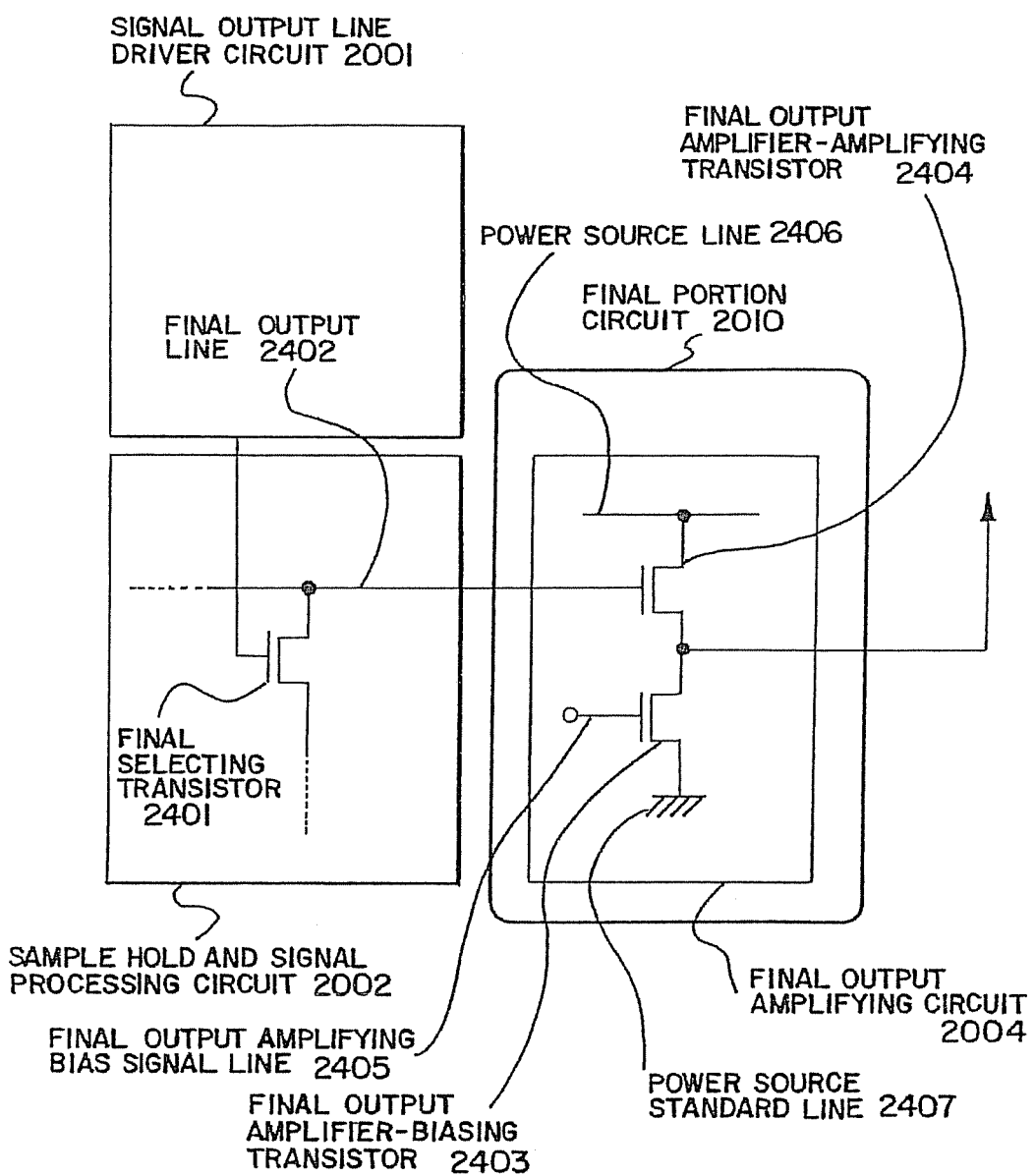
FIG. 24 is a diagram showing a circuit configuration of a final output amplifying circuit signal of the present invention.

The signals that will be output to the final output line 2320 may be withdrawn to the outside. However, because the signals are faint, the signals are frequently amplified before being withdrawn to the outside. As a circuit for carrying out the amplification of the signals, the circuit configuration of the final portion circuit 2010 is shown in FIG. 24. There are various kinds of circuits for amplifying the signals, such as an arithmetic amplifier. Any kind of circuit that can amplify the signals may be used. As the most simple circuit configuration, the source follower circuit is shown here. In FIG. 24, the N channel type is illustrated. Signals that are input to the final output amplifying circuit 2004 will be input to a final output line 2402. Signals are output from the first row in sequence from the final output line 2402. The signals are amplified by the final output amplifying circuit 2004 and then output to the outside. The final output line 2402 is connected to a gate terminal of a final output amplifier-amplifying transistor 2404. A drain terminal of the final output amplifier-amplifying transistor 2404 is connected a power source line 2404, and a source terminal thereof serves as an output terminal. A gate terminal of a final output amplifier-biasing transistor 2403 is connected to a final output amplifying bias signal line 2405, and a source terminal and a drain terminal thereof are connected to a power source standard line 2407 and a source terminal of the final output amplifier-amplifying transistor 2404.

Figure 25:
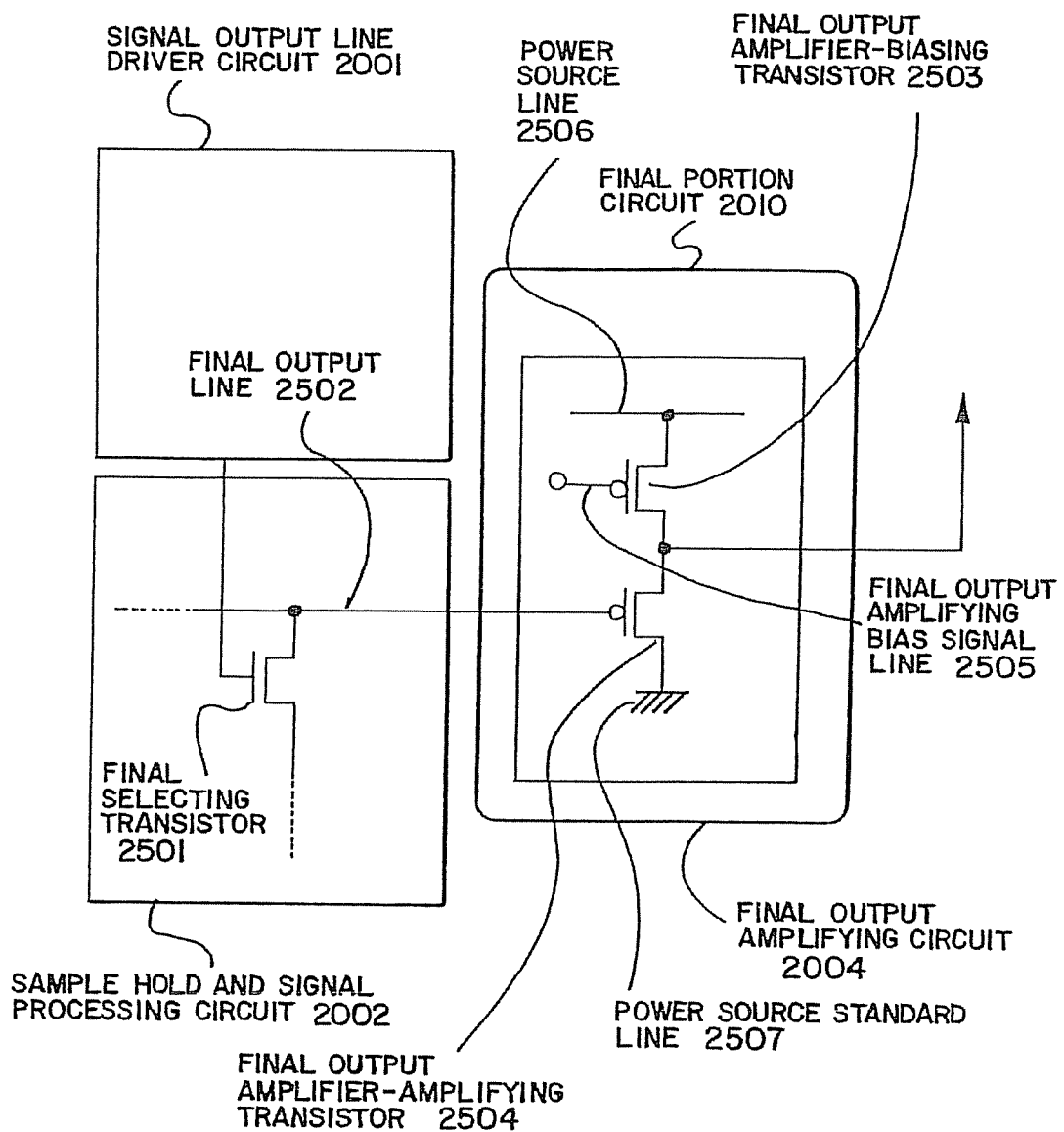
FIG. 25 is a diagram showing a circuit configuration of a final output amplifying circuit signal of the present invention.

Shown in FIG. 25 is a circuit configuration of the source follower circuit when the P channel type is used. The difference from the circuit configuration of FIG. 24 is that the power source line and the power source standard line are reversed. A final output line 2502 is connected to a gate terminal of a final output amplifier-amplifying transistor 2504. A drain terminal of the final output amplifier-amplifying transistor 2504 is connected to a power source standard line 2507, and a source terminal thereof serves as an output terminal. A gate terminal of a final output amplifier-biasing transistor 2503 is connected to a final output amplifying bias signal line 2505. A source terminal and a drain terminal of the final output amplifier-biasing transistor 2503 are connected to a power source line 2506 and a source terminal of the final output amplifier-amplifying transistor 2504. A value of the electric potential of the final output amplifying bias signal line 2505 is different from that of the final output amplifying bias signal line 2405 in the case where the N channel type is used.

In FIGS. 24 and 25, the source follower circuit is constructed of only one level. However, it may also be constructed of plural levels. For example, in the case of constructing the source follower circuit in 2 levels, the output terminal of the first level may be connected to the input terminal of the second level. In addition, in each of the levels, either the N channel type or the P channel type may be used.

The gate signal line and reset signal line driver circuit 2006, the power source line driver circuit 2207, and a signal output line driver circuit AZ01 are circuits which simply output pulse signals. Therefore, implementation thereof can be made by employing a known technique.

Figure 26:
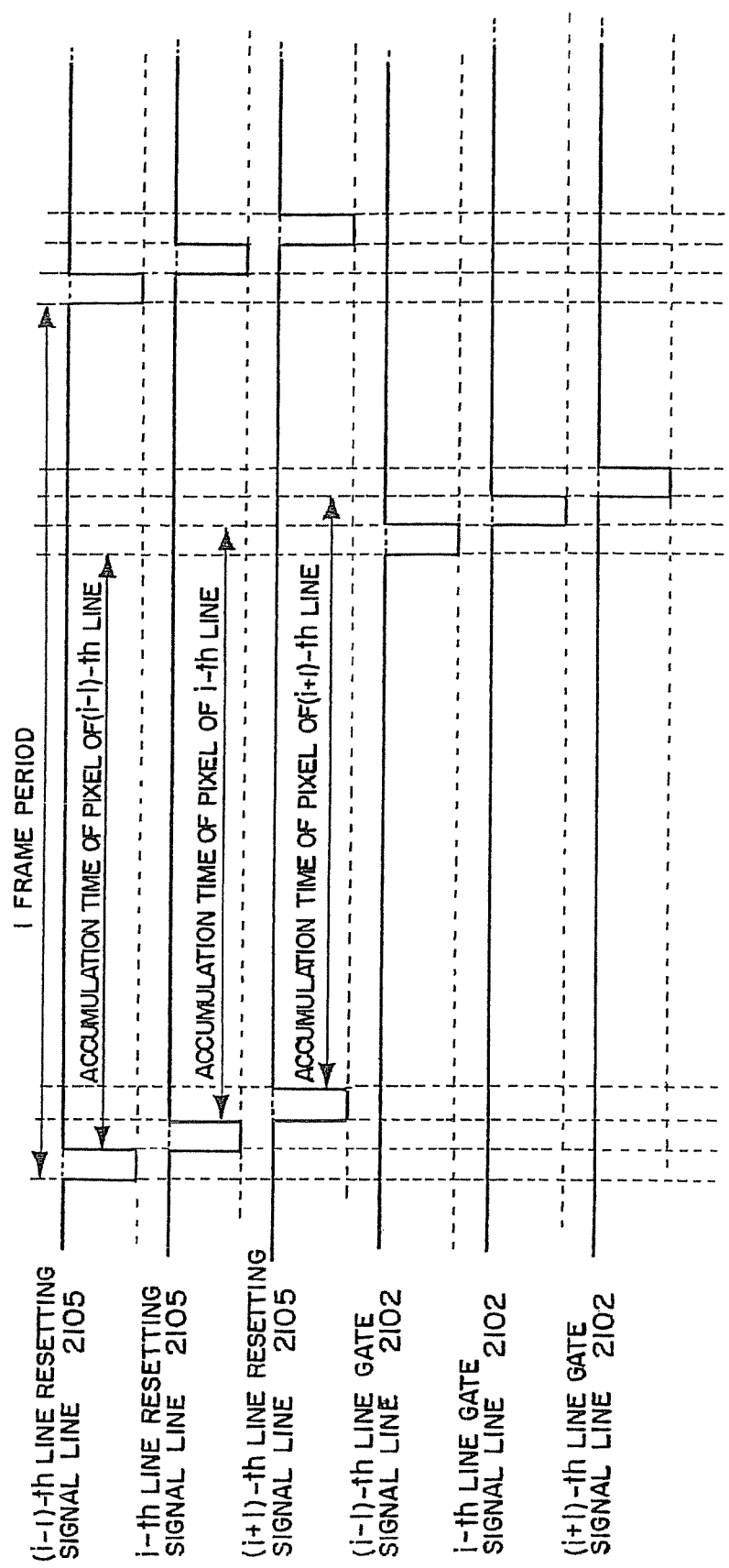
FIG. 26 is a diagram showing a timing chart of an area sensor of the present invention.

A timing chart of a signal will be explained next. The timing chart of the circuit shown in FIG. 20 is illustrated in FIG. 26. The reset signal line is scanned sequentially from the first line. For example, first an (i−1)th line is selected, followed by an ith line, and then an (i+1)th line is selected. A period until the same line is selected again corresponds to a frame period. Similarly, the gate signal line is sequentially scanned from the first line. However, the timing to start scanning the gate signal line is later than the timing to start scanning the reset signal line. For instance, directing the attention to a pixel of the ith line, the ith line reset signal line is selected, and thereafter the ith line gate signal line is selected. When the ith line gate signal line is selected, a signal is output from the pixel of the ith line. A period from the time the pixel is reset until the signal is output becomes an accumulation time. During the accumulation time, electric charges generated by light are being accumulated in the photo diode. The timing to reset and the timing to output a signal are different in each line. Therefore, although the accumulation time of the pixels in all the lines are equivalent, the time that signals are accumulated therein is different.

Figure 27:
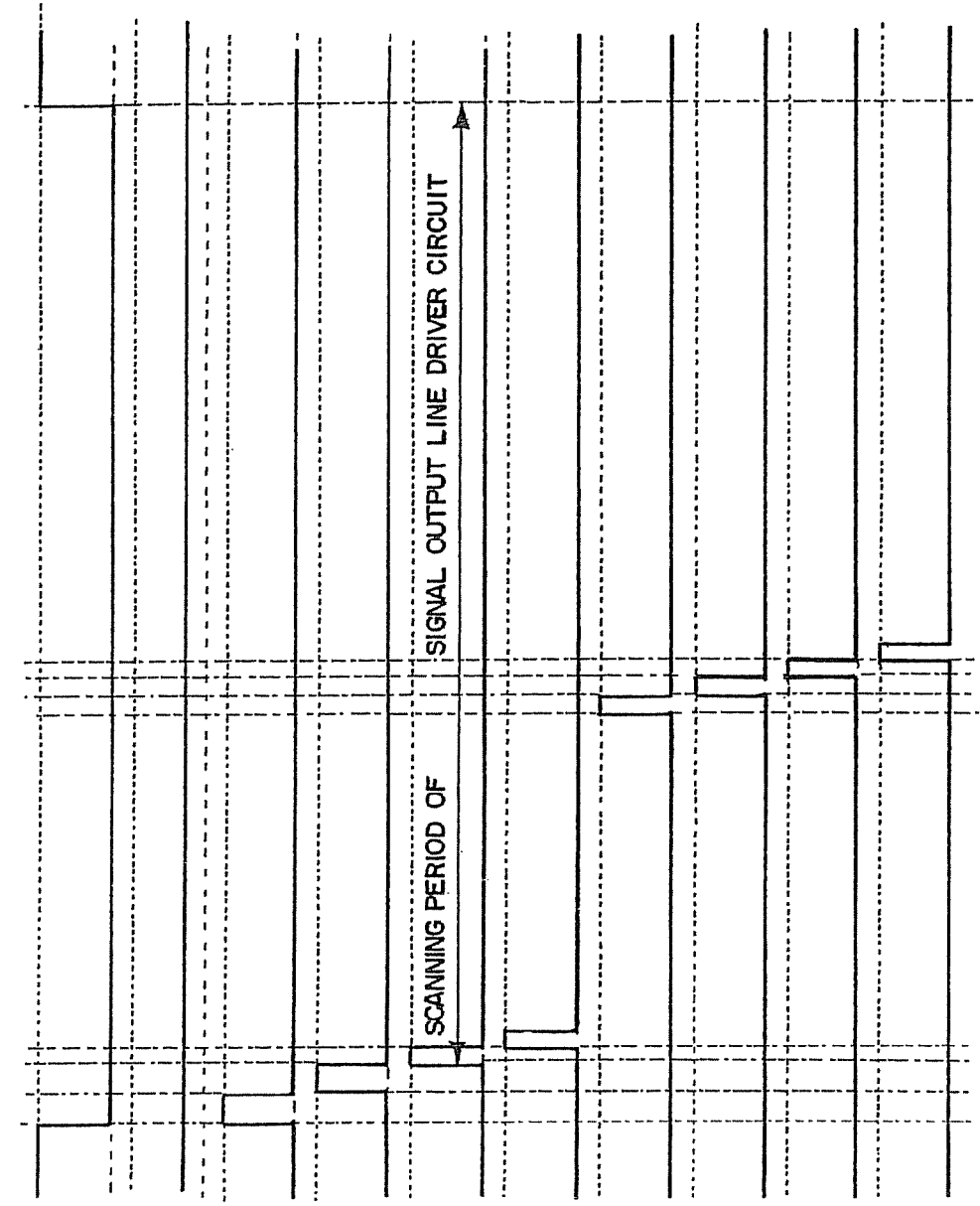
FIG. 27 is a diagram showing a timing chart of an area sensor of the present invention.

Next, the timing chart of a signal of FIG. 23 is shown in FIG. 27. Because the operation is repetitious, the time that the ith line gate signal line is selected will be taken as an example and observed. First, after the ith line gate signal line 2102 is selected, the pre-discharge signal line 2317 is selected to thereby make the electric discharging transistor 2316 in conductive. Subsequently, the transfer signal line 2314 is selected, whereby the signal of each of the rows from the ith line pixel is output to the load capacitance 2315 of every row.

After accumulating the signals of all the pixels of the ith line in the load capacitance 2315 of every row, the signals of every row are sequentially output to the final output line 2320. During the period from the time the transfer signal line 2314 has become non-selective to the time the gate signal line is selected, all the rows are scanned by the signal output line driver circuit 2001. First, the final reset line of the first row is selected to thereby make the final resetting transistor 2322 into conductive, whereby the electric potential of the final output line 2320 is initialized to that of the power source standard line 2312. Thereafter, the final selecting line 2318 of the first row is selected and the final selecting transistor 2319 is turned into conductive to thereby output the signal in the load capacitance 2315 of the first row to the final output line 2320. Next, the final reset line of the second row is selected to thereby make the final resetting transistor 2322 into conductive, whereby the electric potential of the final output line 2320 is initialized to that of the power source standard line 2312. Thereafter, the final selecting line 2318 of the second row is selected and the final selecting transistor 2319 is turned into conductive to thereby output the signal in the load capacitance 2315 of the second row to the final output line 2320. The operation is repeated thereafter. Similarly, in the case of the jth line, the final reset line of the jth row is selected to thereby make the final resetting transistor 2322 into conductive, whereby the electric potential of the final output line 2320 is initialized to that of the power source standard line 2312. Thereafter, the final selecting line 2318 of the jth row is selected and the final selecting transistor 2319 is turned into conductive to thereby output the signal in the load capacitance 2315 of the jth row to the final output line 2320. Next, the final reset line of the (j+1)th row is selected and the final resetting transistor 2322 is turned into conductive, whereby the electric potential of the final output line 2320 is initialized to that of the power source standard line 2312. Thereafter, the final selecting line 2318 of the (j+1)th row is selected and the final selecting transistor 2319 is turned into conductive to thereby output the signal in the load capacitance 2315 of the (j+1)th row to the final output line 2320. The same operation is repeated thereafter to sequentially output all the signals to the final output line. During this operation, the bias signal line 2310 is fixed. The signals output to the final output line 2320 are amplified by the final output amplifying circuit 2004 and then output to the outside.

Next, the (i+1)th line gate signal line is selected. The same operation as performed when the ith line gate signal line was selected will be performed. Then, the gate signal line of the next line will be selected further and the same operation will be repeated.

The electric potential of the bias signal line 2310 will be explained here. In FIG. 23, a plural number of the biasing transistor 2311 is provided. Therefore, even if there is a fluctuation in the threshold voltages of the plural number of the biasing transistor 2311, all the biasing transistors 2311 must be in conductive. As a result, it is necessary to make the absolute value of the voltage between the gate and the source of the biasing transistor equivalent to the minimum value of the absolute value of the voltage between the gate and the source thereof in order to turn all the biasing transistors into conductive.

Note that as for the sensor portion in which photoelectric conversion is performed, other than the usual PN type of photo diode, a PIN type diode, an avalanche diode, an NPN incorporated diode, a Schottky diode, an X-ray photo conductor, and a sensor for infrared rays or the like may be used.

In addition, X-rays may be converted into light by using a fluorescent material or a scintillator and thereafter read the light that has been converted.

As explained so far, the photoelectric conversion element is often connected to the input terminal of the source follower circuit. However, a switch may be sandwiched therebetween like a photo gate type, or the signal, after it has been processed so that it is a logarithmic value of light density, may be input to the input terminal, like a logarithm conversion type.

Although the area sensor having pixels arranged in two-dimensional therein was explained in Embodiment 1, a line sensor having pixels arrange in one-dimensional can also be realized.

Embodiment 2

In Embodiment 2, a case in which pre-discharge is performed by controlling a bias signal line in an area sensor that has pixels arranged in two-dimensional therein and incorporated with driver circuits in the periphery thereof will be explained next. The Embodiment 2 is different from Embodiment 1 only with respect to a portion of the circuit configuration (FIG. 23) and a portion of the signal timing chart (FIG. 27). Therefore, a circuit configuration thereof corresponding to that of FIG. 23 is shown in FIG. 29, and a timing chart of a signal thereof corresponding to that of FIG. 27 is shown in FIG. 28.

Figure 29:
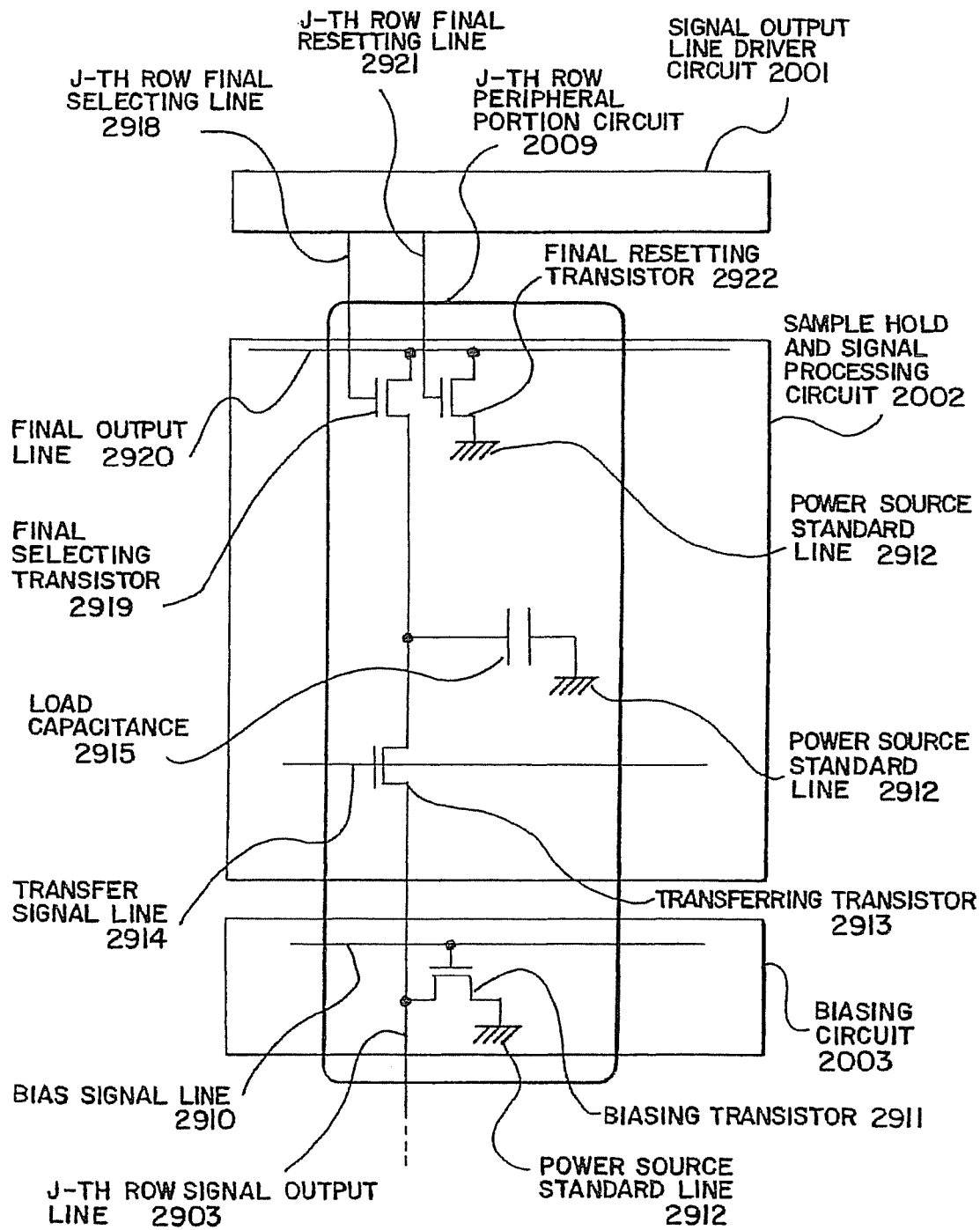
FIG. 29 is a diagram showing a circuit configuration of a signal processing circuit of the present invention.

The circuit configuration of FIG. 29 is one in which the electric discharging transistor 2316 and the pre-discharge signal line 2317 are removed from the circuit configuration of FIG. 23.

Figure 28:
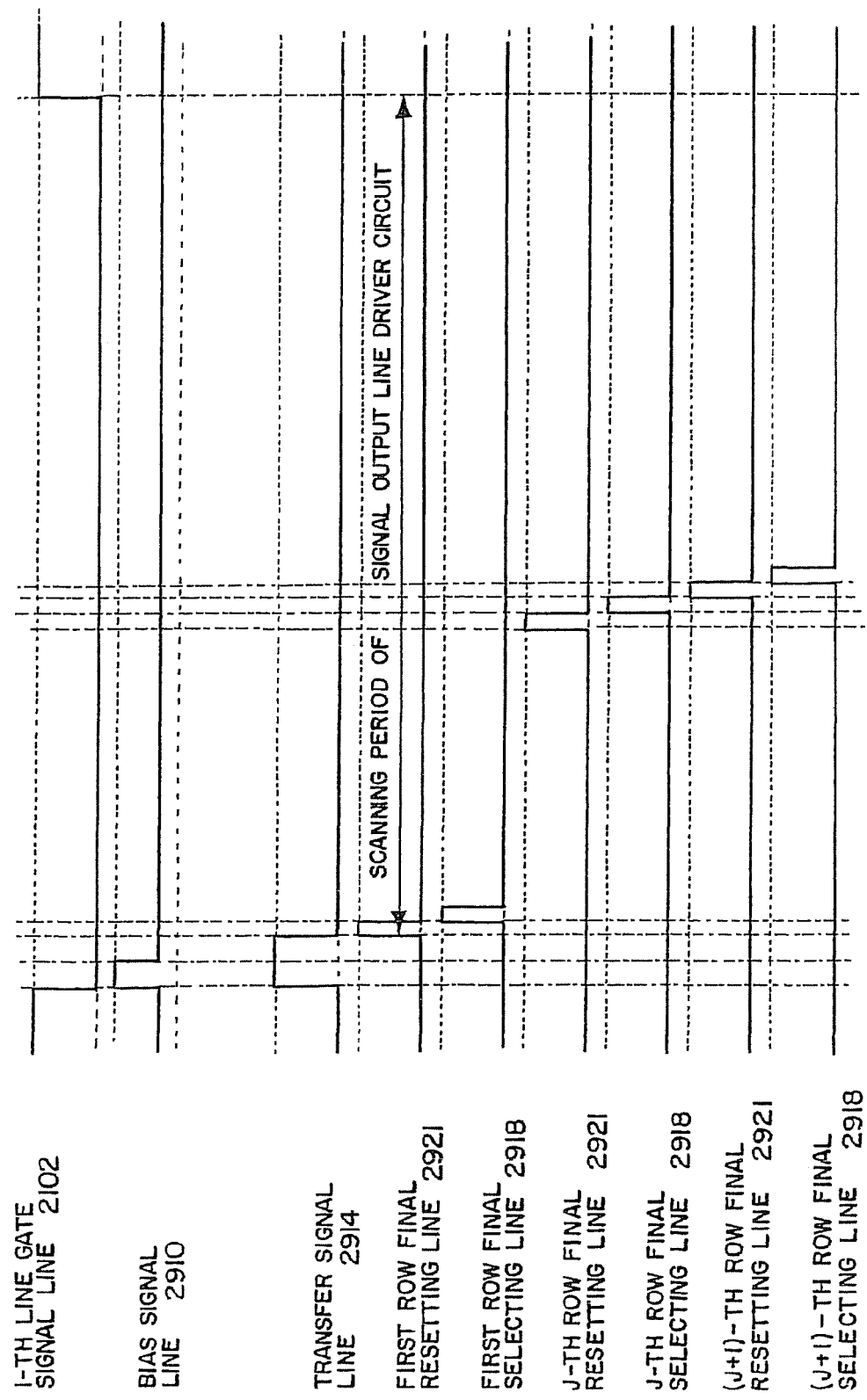
FIG. 28 is a diagram showing a timing chart of an area sensor of the present invention.

Next, the timing chart of a signal in FIG. 29 is shown in FIG. 28. Because the operation is repetitious, the case in which the ith line gate signal line is selected will be taken as an example and observed. First, after the ith line gate signal line 2102 is selected, the electric potential of a bias signal line 2910 and that of a transferring transistor 2913 are raised to thereby perform pre-discharge. Then the electric potential of the bias signal line 2910 is returned to its original value, whereby the signal of each of the rows from the ith line pixels is output to a load capacitance 2915 of every row. The signal of each of the rows is sequentially output to a final output line 2920 after the signals of all the ith line pixels have accumulated in the load capacitance 2915 of every row.

Note that in Embodiment 2, the bias electric potential Vb changes during pre-discharge. Therefore, a signal generating device for changing the bias electric potential Vb may be connected to the bias signal line 2910.

Embodiment 3

A method of manufacturing a sensor portion using TFT on the glass of this invention is explained using FIGS. 30 to 33.

First, as shown in FIG. 30A, a base film 201 is formed to a thickness of 300 nm on a glass substrate 200. A silicon oxinitride film is laminated as the base film 201 in Embodiment 3. At this point, it is appropriate to set the nitrogen concentration to between 10 and 25 wt % in the film contacting the glass substrate 200. In addition, it is effective that the base film 201 has a thermal radiation effect, and a DLC (diamond-like carbon) film may also be provided.

Next, an amorphous silicon film (not shown in the figure) is formed with a thickness of 50 nm on the base film 201 by a known deposition method. Note that it is not necessary to limit to the amorphous silicon film, and a semiconductor film containing an amorphous structure (including a microcrystalline semiconductor film) may be used. In addition, a compound semiconductor film containing an amorphous structure, such as an amorphous silicon germanium film, may also be used. Further, the film thickness may be made from 20 to 100 nm.

The amorphous silicon film is then crystallized by a known technique, forming a crystalline silicon film (also referred to as a polycrystalline silicon film or a polysilicon film) 202. There are thermal crystallization using an electric furnace, laser annealing crystallization using a laser light, and lamp annealing crystallization using an infrared light as known crystallization methods. Crystallization is performed in Embodiment 3 using an excimer laser light, which uses XeCl gas.

Note that pulse emission excimer laser light formed into a linear shape is used in Embodiment 3, but a rectangular shape may also be used. Continuous emission type argon laser light and continuous emission type excimer laser light can also be used.

In this embodiment, although the crystalline silicon film is used as the active layer of the TFT, it is also possible to use an amorphous silicon film as the active layer.

Note that it is effective to form the active layer of the transistor for reset, in which there is a necessity to reduce the off current, by the amorphous silicon film, and to form the active layer of the transistor for amplification by the crystalline silicon film. Electric current flows with difficulty in the amorphous silicon film because the carrier mobility is low, and the off current does not easily flow. In other words, the most can be made of the advantages of both the amorphous silicon film, through which current does not flow easily, and the crystalline silicon film, through which current easily flows.

Next, as shown in FIG. 30B, a protective film 203 is formed on the crystalline silicon film 202 with a silicon oxide film having a thickness of 130 nm. This thickness may be chosen within the range of 100 to 200 nm (preferably between 130 and 170 nm). Furthermore, another films such as insulating films containing silicon may also be used. The protective film 203 is formed so that the crystalline silicon film is not directly exposed to plasma during addition of an impurity, and so that it is possible to have delicate concentration control of the impurity.

Resist masks 204a, 204b, and 204c are then formed on the protective film 203, and an impurity element, which imparts n-type conductivity (hereafter referred to as an n-type impurity element), is added through the protective film 203. Note that elements residing in periodic table group 15 are generally used as the n-type impurity element, and typically phosphorous or arsenic can be used. Note that a plasma doping method is used, in which phosphine ($PH_3$) is plasma-excited without separation of mass, and phosphorous is added at a concentration of $1\times10^{18}$ atoms/cm$^3$ in Embodiment 3. An ion implantation method, in which separation of mass is performed, may also be used, of course.

The dose amount is regulated such that the n-type impurity element is contained in n-type impurity regions (b) 205a, 205b thus formed by this process, at a concentration of $2\times10^{16}$ to $5\times10^{19}$ atoms/cm$^3$ (typically between $5\times10^{17}$ and $5\times10^{18}$ atoms/cm$^3$).

Next, as shown in FIG. 30C, the protective film 203 and the resist masks 204a, 204b, and 204c are removed, and an activation of the added n-type impurity elements is performed. A known technique of activation may be used as the means of activation, but activation is done in Embodiment 3 by irradiation of excimer laser light (laser annealing). Of course, a pulse emission excimer laser and a continuous emission excimer laser may both, be used, and it is not necessary to place any limits on the use of excimer laser light. The goal is the activation of the added impurity element, and it is preferable that irradiation is performed at an energy level at which the crystalline silicon film does not melt. Note that the laser irradiation may also be performed with the protective film 203 in place.

The activation of impurity elements by heat treatment (furnace annealing) may also be performed along with activation of the impurity element by laser light. When activation is performed by heat treatment, considering the heat resistance of the substrate, it is good to perform heat treatment at about 450 to 550° C.

A boundary portion (connecting portion) with end portions of the n-type impurity regions (b) 205a, 205b, namely regions, in which the n-type impurity element is not added, on the periphery of the n-type impurity regions (b) 205a, 205b, is delineated by this process. This means that, at the point when the TFTs are later completed, extremely good connecting portion can be formed between LDD regions and channel forming regions.

Unnecessary portions of the crystalline silicon film are removed next, as shown in FIG. 30D, and island-shape semiconductor films (hereinafter referred to as active layers) 206 to 210 are formed.

Then, as shown in FIG. 31A, a gate insulating film 211 is formed, covering the active layers 206 to 210. An insulating film containing silicon and with a thickness of 10 to 200 nm, preferably between 50 and 150 nm, may be used as the gate insulating film 211. A single layer structure or a lamination structure may be used. A 110 nm thick silicon oxinitride film is used in Embodiment 3.

Thereafter, a conductive film having a thickness of 200 to 400 nm is formed and patterned to form gate electrodes 212 to 216. In Embodiment 3, the gate electrodes and wirings (hereinafter referred to as gate wirings) electrically connected to the gate electrodes for providing conductive paths are formed of the same materials. Of course, the gate electrode and the gate wiring may be formed of different materials from each other. More specifically, the gate wirings are made of a material having a lower resistivity than the gate electrodes. This is because a material enabling fine processing is used for the gate electrodes, while the gate wirings are formed of a material that can provide a smaller wiring resistance but is not suitable for fine processing. The wiring resistance of the gate wiring can be made extremely small by using this type of structure, and therefore a sensor portion having a large surface area can be formed. Namely, the above described pixel structure is extremely effective when an area sensor with a sensor portion having a screen size of a 10 inch diagonal or larger (in addition, a 30 inch or larger diagonal) is realized.

Although the gate electrode can be made of a single-layered conductive film, it is preferable to form a lamination film with two layers or three layers, if necessary. Any known conductive films can be used for the gate electrodes 212 to 216.

Typically, it is possible to use a film made of an element selected from the group consisting of aluminum (Al), tantalum (Ta), titanium (Ti), molybdenum (Mo), tungsten (W), chromium (Cr), and silicon (Si), a film of nitride of the above element (typically a tantalum nitride film, tungsten nitride film, or titanium nitride film), an alloy film of combination of the above elements (typically Mo—W alloy or Mo—Ta alloy), or a silicide film of the above element (typically a tungsten silicide film or titanium silicide film). Of course, the films may be used as a single layer or a laminate layer.

In Embodiment 3, a laminate film of a tungsten nitride (WN) film having a thickness of 30 nm and a tungsten (W)

film having a thickness of 370 nm is used. This may be formed by sputtering. When an inert gas such as Xe or Ne is added as a sputtering gas, film peeling due to stress can be prevented.

The gate electrodes 213 and 216 are respectively formed at this time so as to overlap a portion of the n-type impurity regions (b) 205a and 205b through the gate insulating film 211. This overlapping portion later becomes an LDD region overlapping the gate electrode.

Next, an n-type impurity element (phosphorous is used in Embodiment 3) is added in a self-aligning manner with the gate electrodes 212 to 216 as masks, as shown in FIG. 31B. The addition is regulated such that phosphorous is added to n-type impurity regions (c) 217 to 224 thus formed at a concentration of 1/10 to 1/2 that of the n-type impurity regions (b) 205a and 205b (typically between 1/4 and 1/3). Specifically, a concentration of $1 \times 10^{16}$ to $5 \times 10^{18}$ atoms/cm$^3$ (typically $3 \times 10^{17}$ to $3 \times 10^{18}$ atoms/cm$^3$) is preferable.

Resist masks 225a to 225c are formed next, with a shape covering the gate electrodes 212, 214 and 215, as shown in FIG. 31C, and an n-type impurity element (phosphorous is used in Embodiment 3) is added, forming impurity regions (a) 226 to 233 containing phosphorous at high concentration. Ion doping using phosphine (PH$_3$) is also performed here, and the phosphorous concentration of these regions is regulated so as to be set to from $1 \times 10^{20}$ to $1 \times 10^{21}$ atoms/cm$^3$ (typically between $2 \times 10^{20}$ and $5 \times 10^{21}$ atoms/cm$^3$).

A source region or a drain region of the n-channel TFT is formed by this process, and in the n-channel TFT, a portion of the n-type impurity regions (c) 217, 218, 222, and 223 formed by the process of FIG. 31B is remained. These remaining regions correspond to LDD regions.

Next, as shown in FIG. 31D, the resist masks 225a to 225c are removed, and new resist masks 234a and 234b are formed. A p-type impurity element (boron is used in Embodiment 3) is then added, forming p-type impurity regions 235 and 236 containing boron at high concentration. Boron is added here at a concentration of $3 \times 10^{20}$ to $3 \times 10^{21}$ atoms/cm$^3$ (typically between $5 \times 10^{20}$ and $1 \times 10^{21}$ atoms/cm$^3$) by ion doping using diborane (B$_2$H$_6$).

Note that phosphorous has already been added to the impurity regions 235 and 236 at a concentration of $1 \times 10^{20}$ to $1 \times 10^{21}$ atoms/cm$^3$, but boron is added here at a concentration of at least 3 times or more that of the phosphorous. Therefore, the n-type impurity regions already formed completely invert to p-type, and function as p-type impurity regions.

Next, after removing the resist masks 234a and 234b, the n-type or p-type impurity elements added to the active layer at respective concentrations are activated. Furnace annealing, laser annealing or lamp annealing can be used as a means of activation. In Embodiment 3, heat treatment is performed for 4 hours at 550° C. in a nitrogen atmosphere in an electric furnace.

At this time, it is important to eliminate oxygen from the surrounding atmosphere as much as possible. This is because an exposed surface of the gate electrode is oxidized, which results in an increased resistance if only a small amount of oxygen exists. Accordingly, the oxygen concentration in the surrounding atmosphere for the activation process is set at 1 ppm or less, preferably at 0.1 ppm or less.

Figure 32A:
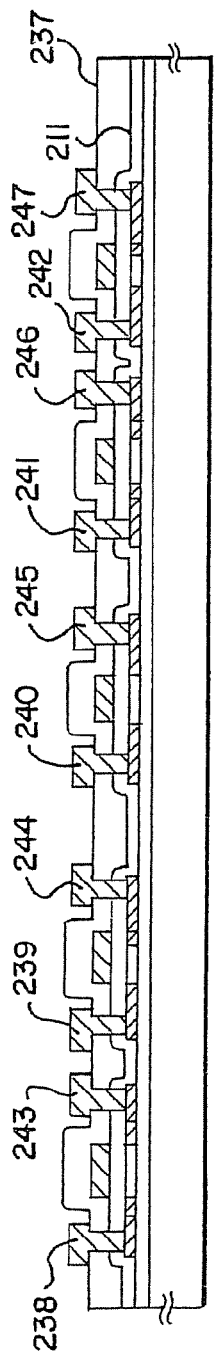
FIGS. 32A to 32C are diagrams showing manufacturing processes of an image sensor of the present invention.

A first interlayer insulating film 237 is formed next, as shown in FIG. 32A. A single layer insulating film containing silicon is used as the first interlayer insulating film 237, or a lamination film may be used. Further, a film thickness of between 400 nm and 1.5 µm may be used. A lamination structure of a silicon oxide film having a thickness of 800 nm on a silicon oxinitride film having a thickness of 200 nm thick is used in Embodiment 3.

In addition, heat treatment is performed for 1 to 12 hours at 300 to 450° C. in an atmosphere containing between 3 and 100% hydrogen, performing hydrogenation. This process is one of hydrogen termination of dangling bonds in the semiconductor film by hydrogen, which is thermally excited. Plasma hydrogenation (using hydrogen excited by plasma) may also be performed as another means of hydrogenation.

Note that the hydrogenation processing may also be inserted during the formation of the first interlayer insulating film 237. Namely, hydrogen processing may be performed as above after forming the 200 nm thick silicon oxinitride film, and then the remaining 800 nm thick silicon oxide film may be formed.

Next, a contact hole is formed in the gate insulating film 211 and the first interlayer insulating film 237, and source wirings 238 to 242 and drain wirings 243 to 247 are formed. In this embodiment, this electrode is made of a laminate film of three-layer structure in which a titanium film having a thickness of 100 nm, an aluminum film containing titanium and having a thickness of 300 nm, and a titanium film having a thickness of 150 nm are continuously formed by sputtering. Of course, other conductive films may be used.

A first passivation film 248 is formed next with a thickness of 50 to 500 nm (typically between 200 and 300 nm). A 300 nm thick silicon oxinitride film is used as the first passivation film 248 in Embodiment 3. This may also be substituted by a silicon nitride film. Note that it is effective to perform plasma processing using a gas containing hydrogen such as H$_2$ or NH$_3$ before the formation of the silicon oxinitride film. Hydrogen activated by this preprocess is supplied to the first interlayer insulating film 237, and the film quality of the first passivation film 248 is improved by performing heat treatment. At the same time, the hydrogen added to the first interlayer insulating film 237 diffuses to the lower side, and the active layers can be hydrogenated effectively.

Figure 32B:
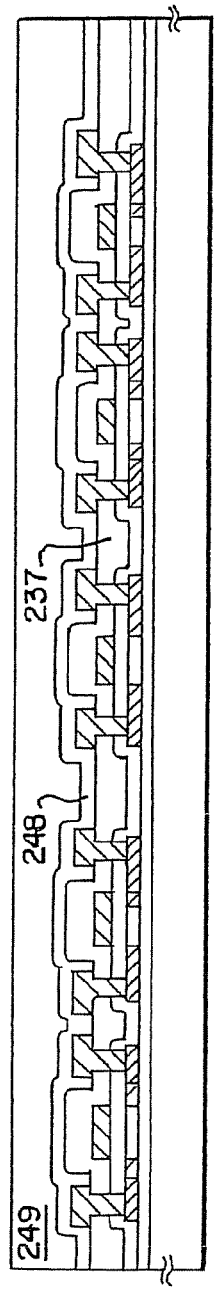

Next, a second interlayer insulating film 249 made of organic resin is formed as shown in FIG. 32B. As the organic resin, it is possible to use polyimide, polyamide, acryl, BCB (benzocyclobutene) or the like. Especially, since the second interlayer insulating film 249 is primarily used for leveling, acryl excellent in leveling properties is preferable. In this embodiment, an acrylic film is formed to a thickness sufficient to level a stepped portion formed by TFTs. It is appropriate that the thickness is made 1 to 5 µm (more preferably, 2 to 4 µm).

Next, a contact hole is formed in the second interlayer insulating film 249 and the first passivation film 248 so as to reach the drain wiring 245, and a cathode electrode 250 of a photodiode is formed so as to contact the drain wiring 245. In embodiment 3, an aluminum film formed by sputtering is used as the cathode electrode 250, but other metals, for example titanium, tantalum, tungsten, and copper can also be used. Further, a lamination film made from titanium, aluminum, and titanium may also be used.

Figure 32C:
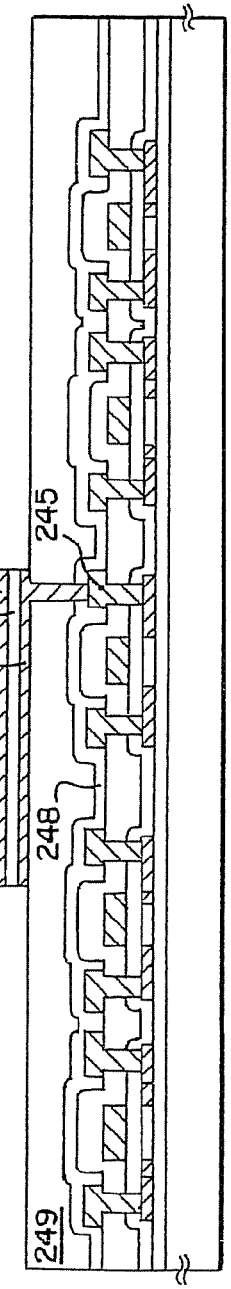

Patterning is next performed after depositing an amorphous silicon film containing hydrogen over the entire surface of the substrate, and a photoelectric conversion layer 251 is formed. Then, a transparent conductive film is formed on the entire surface of the substrate. A 200 nm thick ITO film is deposited by sputtering as the transparent conductive film in Embodiment 3. The transparent conductive film is patterned, forming an anode electrode 252. (FIG. 32C.)

Figure 33A:
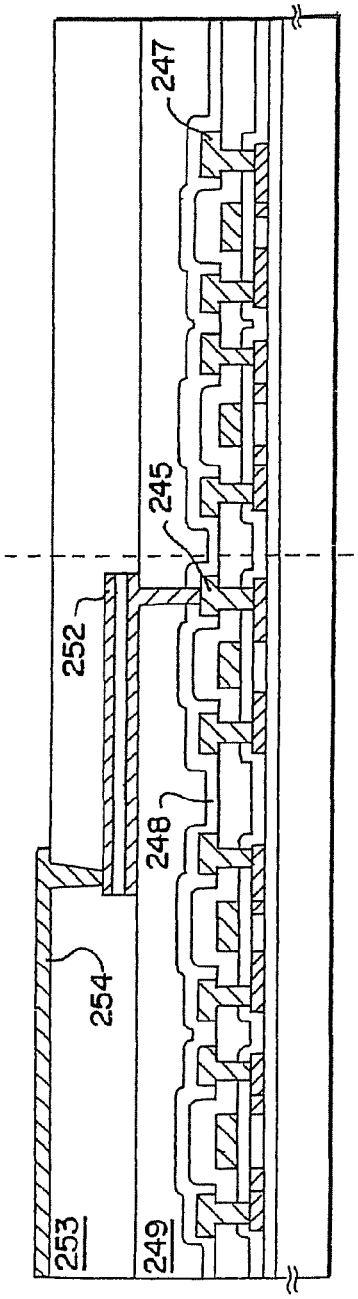
FIGS. 33A and 33B are diagrams showing manufacturing processes of an image sensor of the present invention.

A third interlayer insulating film 253 is then formed, as shown in FIG. 33A. A level surface can be obtained by using a resin such as polyimide, polyamide, polyimide amide, or acrylic as the third interlayer insulating film 253. A polyimide film having a thickness of 0.7 μm is formed over the entire surface of the substrate as the third interlayer insulating film 253 in Embodiment 3.

A contact hole is next formed in the third interlayer insulating film 253 so as to reach the anode electrode 252, and a sensor wiring 254 is formed. A 300 nm thick aluminum alloy film (an aluminum film comprising titanium of 1 wt %) is formed in Embodiment 3.

Figure 33B:
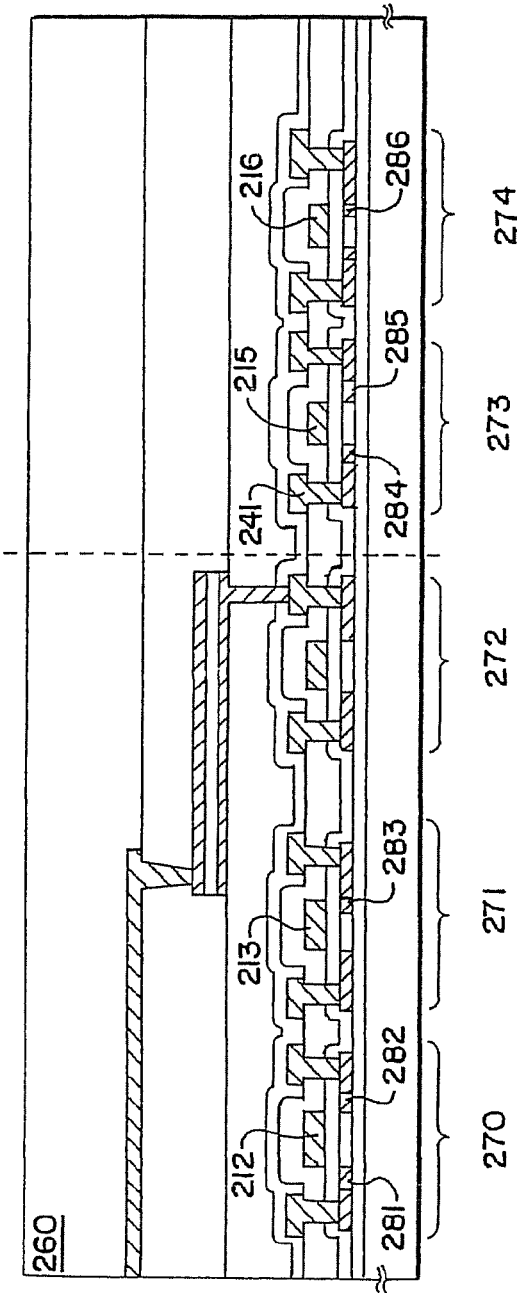

The sensor substrate is formed which has the structure as shown in FIG. 33B.

Reference numeral 270 shows an amplifier TFT, 271 shows a switching TFT, 272 shows reset TFT, 273 shows a bias TFT, and 274 shows discharge TFT.

In embodiment 3, the amplifier TFT 270 and the bias TFT 273 are an n-channel TFT, and both of source region side and drain region side have LDD regions 281-282 and 284-285. Note that the LDD regions 281-282 and 284-285 do not overlap with the gate electrodes 212 and 215 through the gate insulating film 211. The above constitution of the amplifier TFT 270 and the bias TFT 273 can reduce the hot carrier injection as much as possible.

Further in Embodiment 3, the switching TFT 271 and the discharge TFT 274 is a n-channel TFT, each TFTs has LDD regions 283 and 286 on only the drain region side. The LDD region 283 and 286 are overlapped to the gate electrode 213 and 216 interposing the gate insulating film 211.

The formation of the LDD regions 283 and 286 on only the drain region side is in consideration of reducing the hot carrier injection and not causing the operating speed to drop. Further, it is not necessary to be too concerned with the value of the off current for the switching TFT 271 and the discharge TFT 274, and more importance may be placed on the operating speed. It is therefore preferable for the LDD regions 283 and 286 to completely overlap with the gate electrodes 213 and 216, and to reduce resistive components as much as possible. Namely, the so-called offset should be eliminated. In particular, when the source signal line driver circuit or the gate signal line driving circuit is driven at 15V to 20V, the above constitution of the discharge TFT 274 of Embodiment 3 is effective to reduce the hot carrier injection and also not to drop the operation speed.

Furthermore, in Embodiment 3, a reset TFT 272 is p-channel TFT and has no LDD region. Degradation due to hot carrier injection is almost of no concern for the p-channel TFTs, and therefore LDD regions do not have to be formed in particular. It is also possible, of course, to form an LDD region similar to that of an n-channel TFT to take action against hot carriers. Further, the reset TFT 272 may be an n-channel type TFT.

The device is completed as a manufactured product by attaching a connector (flexible printed circuit, FPC) for connecting terminals pulled around from the elements or circuits formed on the substrate with external signal terminals.

The sensor is formed by using a TFT on the glass or the photodiode in this embodiment, the transistor on the single crystalline silicon substrate can also be used.

Embodiment 4

The sensor manufactured by implementing the present invention can be used for various kinds of electronic equipments. The following can be given as such electronic equipment according to the present invention: a scanner; a digital still, camera; an x-ray camera; a portable information terminal (a mobile computer, a portable telephone, and a portable game machine); a notebook type personal computer; a game apparatus; a video telephone, etc.

Figure 34A:
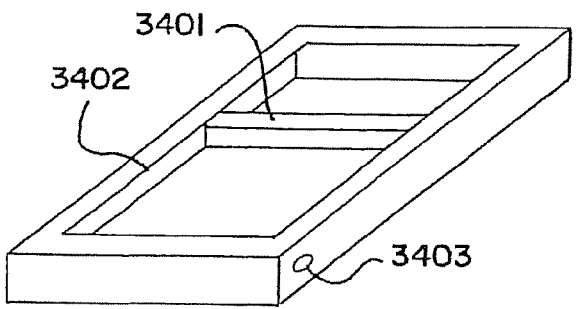
FIGS. 34A and 34B are diagrams showing electronic equipments using the image sensor of the present invention.

FIG. 34A is a scanner, and contains a reading region 3402, a sensor portion 3401, a reading operation start switch 3404 and the like. The present invention can be used as the sensor portion 3401.

Figure 34B:
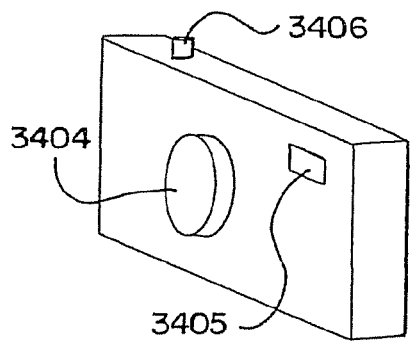

FIG. 34B is a digital still camera, and contains a finder 3405, a sensor portion 3404, a shutter button 3406 and the like. The present invention can be used as the sensor portion 3404.

Figure 35:
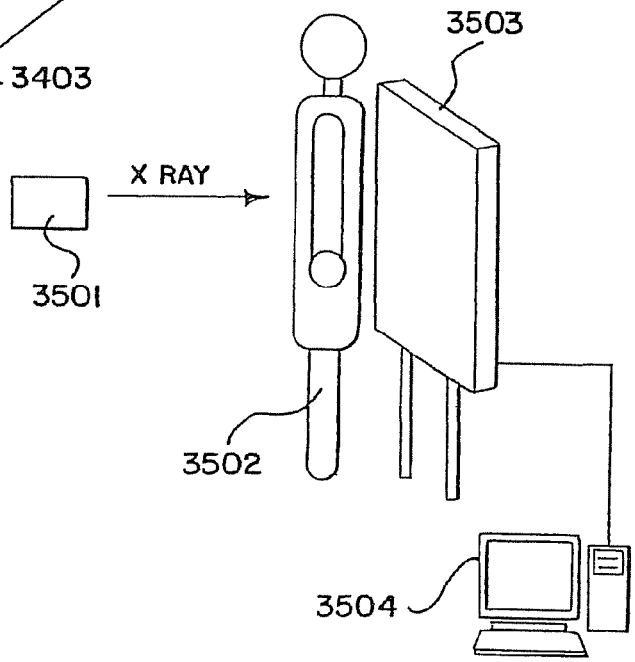
FIG. 35 is a diagram showing an electronic equipment using the image sensor of the present invention.

FIG. 35 is an x-ray camera, and contains an x-ray generator 3501, a sensor portion 3503, a computer 3054 for signal processing and the like. An object 3502 to be examined stands between the x-ray generator 3501 and the sensor portion 3503, and the x-ray photograph is taken. The present invention can be used as the sensor portion 3503.

Figure 36:
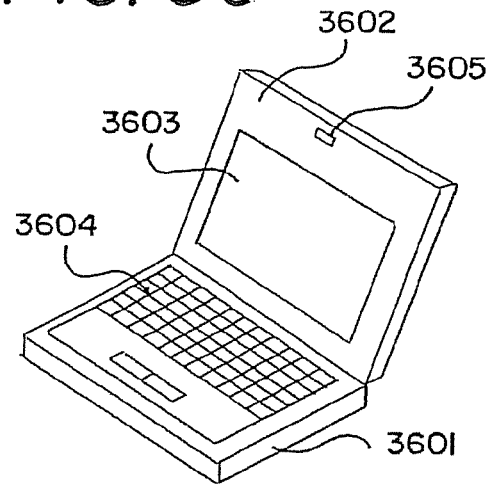
FIG. 36 is a diagram showing an electronic equipment using the image sensor of the present invention.

FIG. 36 is a personal computer, and contains a main body 3601, a casing 3602, a display 3603, a keyboard 3604, a sensor portion 3605 and the like. The present invention can be used as the display 3603 and the sensor portion 3605.

Figure 37:
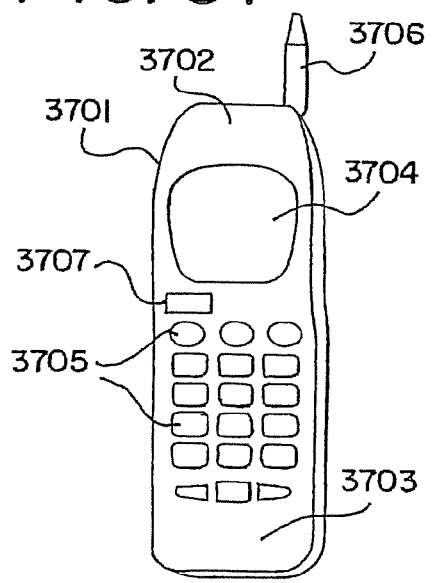
FIG. 37 is a diagram showing an electronic equipment using the image sensor of the present invention.

Here, FIG. 37 shows a portable telephone, and contains a main body 3701, a sound output portion 3702, a sound input portion 3703, a display 3704, operation switches 3705, an antenna 3706 and a sensor portion 3707. The present invention can be used as the sensor portion 3707.

The present invention enables enlarging of the amplitude of the output while preventing the writing-in time of the output electric potential of the source follower circuit from becoming long. Further, at the same time, the present invention can widen the operating region in which the input/output relationship of the source follower circuit is linear. Consequently, an area sensor having a high image quality is realized.

What is claimed is:

1. An X-ray system comprising:
an X-ray generator configured to irradiate an object with an X-ray;
a sensor portion configured to sense light; and
a computer configured to process a signal which is generated in response to the light sensed by the sensor portion,
wherein the sensor portion comprises:
a circuit including a first transistor, a second transistor, a switching transistor, and a photoelectric conversion element;
a third transistor;
a fourth transistor;
a fifth transistor;
a capacitor element;
a first wiring;
a second wiring;
a third wiring; and
a power source line,
wherein one of a source and a drain of the first transistor is electrically connected to the first wiring,
wherein a gate of the first transistor is electrically connected to the photoelectric conversion element,
wherein the gate of the first transistor is electrically connected to one of a source and a drain of the second transistor,
wherein the other of the source and the drain of the second transistor is electrically connected to the second wiring;
wherein one of a source and a drain of the third transistor is electrically connected to the first wiring and the other of the source and the drain of the third transistor is electrically connected to the power source line,
wherein one of a source and a drain of the fourth transistor is electrically connected to the first wiring and the other of the source and the drain of the fourth transistor is electrically connected to the third wiring, wherein one of a source and a drain of the fifth transistor is electrically connected to the third wiring and the other of the source and the drain of the fifth transistor is electrically connected to the power source line, and wherein a first electrode of the capacitor element is electrically connected to the one of the source and the drain of the fifth transistor and a second electrode of the capacitor element is electrically connected to the other of the source and the drain of the fifth transistor.

2. The X-ray system according to claim 1, wherein one of a source and a drain of the switching transistor is electrically connected to the one of the source and the drain of the first transistor.

3. The X-ray system according to claim 1, wherein the second wiring is a first power source line.

4. The X-ray system according to claim 1, wherein the fifth transistor is configured to discharge an electrical charge of the capacitor element.

5. The X-ray system according to claim 1, wherein a conductive type of the first transistor is same as that of the second transistor.

6. The X-ray system according to claim 1, wherein a conductive type of the first transistor differs from that of the second transistor.

7. The X-ray system according to claim 1, wherein the first transistor is a p-channel transistor.

8. The X-ray system according to claim 1, wherein the light is the X-ray through the object.

9. The X-ray system according to claim 1, wherein the X-ray through the object is converted into the light by using a fluorescent material or a scintillator.

10. An X-ray system comprising:
an X-ray generator configured to irradiate an object with an X-ray;
a sensor portion configured to sense light; and
a computer configured to process a signal which is generated in response to the light sensed by the sensor portion,
wherein the sensor portion comprises:
a circuit including a first transistor, a second transistor, a switching transistor, and a photoelectric conversion element;
a third transistor;
a fourth transistor;
a fifth transistor;
a capacitor element;
a first wiring;
a second wiring;
a third wiring;
a first power source line; and
a second power source line,
wherein one of a source and a drain of the first transistor is electrically connected to the first wiring,
wherein a gate of the first transistor is electrically connected to the photoelectric conversion element,
wherein the gate of the first transistor is electrically connected to one of a source and a drain of the second transistor,
wherein the other of the source and the drain of the second transistor is electrically connected to the second wiring;
wherein one of a source and a drain of the third transistor is electrically connected to the first wiring and the other of the source and the drain of the third transistor is electrically connected to the first power source line,
wherein one of a source and a drain of the fourth transistor is electrically connected to the first wiring and the other of the source and the drain of the fourth transistor is electrically connected to the third wiring, wherein one of a source and a drain of the fifth transistor is electrically connected to the third wiring and the other of the source and the drain of the fifth transistor is electrically connected to the second power source line, and wherein a first electrode of the capacitor element is electrically connected to the one of the source and the drain of the fifth transistor and a second electrode of the capacitor element is electrically connected to the other of the source and the drain of the fifth transistor.

11. The X-ray system according to claim 10, wherein one of a source and a drain of the switching transistor is electrically connected to the one of the source and the drain of the first transistor.

12. The X-ray system according to claim 10, wherein the second wiring is a third power source line.

13. The X-ray system according to claim 10, wherein the fifth transistor is configured to discharge an electrical charge of the capacitor element.

14. The X-ray system according to claim 10, wherein a conductive type of the first transistor is same as that of the second transistor.

15. The X-ray system according to claim 10, wherein a conductive type of the first transistor differs from that of the second transistor.

16. The X-ray system according to claim 10, wherein the first transistor is a p-channel transistor.

17. The X-ray system according to claim 10, wherein the light is the X-ray through the object.

18. The X-ray system according to claim 10, wherein the X-ray through the object is converted into the light by using a fluorescent material or a scintillator.

19. An X-ray system comprising:
an X-ray generator configured to irradiate an object with an X-ray;
a sensor portion configured to sense light; and
a computer configured to process a signal which is generated in response to the light sensed by the sensor portion,
wherein the sensor portion comprises:
a circuit including a first transistor, a second transistor, a switching transistor, and a photoelectric conversion element;
a third transistor;
a fourth transistor;
a fifth transistor;
a capacitor element;
a first wiring;
a second wiring;
a third wiring;
a first power source line; and
a second power source line,
wherein one of a source and a drain of the first transistor is electrically connected to the first wiring,
wherein a gate of the first transistor is electrically connected to a first line,
wherein one of a source and a drain of the second transistor is electrically connected to the first line,
wherein the other of the source and the drain of the second transistor is electrically connected to the second wiring;
wherein one of a source and a drain of the third transistor is electrically connected to the first wiring and the other of the source and the drain of the third transistor is electrically connected to the first power source line,
wherein one of a source and a drain of the fourth transistor is electrically connected to the first wiring and the other of the source and the drain of the fourth transistor is electrically connected to the third wiring, wherein one of a source and a drain of the fifth transistor is electrically connected to the third wiring and the other of the source and the drain of the fifth transistor is electrically connected to the second power source line, and wherein a first electrode of the capacitor element is electrically connected to the one of the source and the drain of the fifth transistor and a second electrode of the capacitor element is electrically connected to the other of the source and the drain of the fifth transistor.

20. The X-ray system according to claim 19, wherein one of a source and a drain of the switching transistor is electrically connected to the one of the source and the drain of the first transistor.

21. The X-ray system according to claim 19, wherein the second wiring is a third power source line.

22. The X-ray system according to claim 19, wherein the fifth transistor is configured to discharge an electrical charge of the capacitor element.

23. The X-ray system according to claim 19, wherein a conductive type of the first transistor is same as that of the second transistor.

24. The X-ray system according to claim 19, wherein a conductive type of the first transistor differs from that of the second transistor.

25. The X-ray system according to claim 19, wherein the first transistor is a p-channel transistor.

26. The X-ray system according to claim 19, wherein the light is the X-ray through the object.

27. The X-ray system according to claim 19, wherein the X-ray through the object is converted into the light by using a fluorescent material or a scintillator.

* * * * *